US008999667B2

(12) United States Patent
Otte et al.

(10) Patent No.: US 8,999,667 B2
(45) Date of Patent: *Apr. 7, 2015

(54) SELECTION OF HOST CELLS EXPRESSING PROTEIN AT HIGH LEVELS

(75) Inventors: Arie P. Otte, Amersfoort (NL); Theodorus H. J. Kwaks, Amsterdam (NL); Henricus J. M. van Blokland, Wijdewormer (NL); Richard G. A. B. Sewalt, Arnhem (NL)

(73) Assignee: Chromagenics B.V., Leiden (NL)

(*) Notice: Subject to any disclaimer, the term of this patent is extended or adjusted under 35 U.S.C. 154(b) by 463 days.

This patent is subject to a terminal disclaimer.

(21) Appl. No.: 11/899,505

(22) Filed: Sep. 6, 2007

(65) Prior Publication Data
US 2008/0085537 A1 Apr. 10, 2008

Related U.S. Application Data

(63) Continuation-in-part of application No. 11/269,525, filed on Nov. 7, 2005, and a continuation-in-part of application No. 11/359,953, filed on Feb. 21, 2006, which is a continuation-in-part of application No. 11/269,525, application No. 11/899,505, which is a continuation-in-part of application No. 11/416,490, filed on May 2, 2006, which is a continuation-in-part of application No. 11/269,525, application No. 11/899,505, which is a continuation-in-part of application No. PCT/EP2007/051696, filed on Feb. 21, 2007, which is a continuation-in-part of application No. 11/359,953, filed on Feb. 21, 2006, which is a continuation-in-part of application No. 11/416,490.

(60) Provisional application No. 60/626,301, filed on Nov. 8, 2004, provisional application No. 60/696,610, filed on Jul. 5, 2005.

(30) Foreign Application Priority Data

Nov. 8, 2004 (EP) .................................... 04105593
May 2, 2006 (EP) .................................... 06113354

(51) Int. Cl.
*C12N 15/63* (2006.01)
*C12N 15/65* (2006.01)
*C12N 15/67* (2006.01)
*C12N 15/79* (2006.01)
*C12N 15/85* (2006.01)

(52) U.S. Cl.
CPC ............ *C12N 15/85* (2013.01); *C12N 2830/46* (2013.01); *C12N 2840/203* (2013.01)

(58) Field of Classification Search
USPC ............ 435/69.1, 320.1; 536/23.1, 23.7, 24.1
See application file for complete search history.

(56) References Cited

U.S. PATENT DOCUMENTS

| 4,965,196 A | 10/1990 | Levinson et al. |
| 5,021,344 A | 6/1991 | Armau et al. |
| 5,118,620 A | 6/1992 | Armau et al. |
| 5,527,701 A | 6/1996 | Yamaguchi et al. |
| 5,561,053 A | 10/1996 | Crowley |
| 5,610,053 A | 3/1997 | Chung et al. |
| 5,627,033 A | 5/1997 | Smith et al. |
| 5,648,267 A | 7/1997 | Reff |
| 5,733,779 A | 3/1998 | Reff |
| 5,773,695 A | 6/1998 | Thompson et al. |
| 5,888,809 A | 3/1999 | Allison |
| 5,994,128 A | 11/1999 | Fallaux et al. |
| 6,107,477 A | 8/2000 | Whitney et al. |
| 6,319,707 B1 | 11/2001 | Adam et al. |
| 6,395,549 B1 | 5/2002 | Tuan et al. |
| 6,413,744 B1 | 7/2002 | Morris et al. |
| 6,521,419 B1 | 2/2003 | Koduri et al. |
| 6,558,948 B1 | 5/2003 | Kochanek et al. |

(Continued)

FOREIGN PATENT DOCUMENTS

| EP | 0724639 B1 | 1/2001 |
| EP | 1 273 666 | 1/2003 |

(Continued)

OTHER PUBLICATIONS

Kaufman et al, N.A.R. 19(16):4485-4490, 1991.*
Database EMBL 'Online! Jan. 25, 2001, "QV2-NN0045-081200-535-c10 NN0045 *Homo sapiens* cDNA, mRNA sequence." XP002359993 retrieved from EBI accession No. EM_PRO:BF960930, database accession No. BF960930 for SEQ ID No. 43.
Kozak, M., An analysis of 5'-noncoding sequences from 699 vertebrate messenger RNAs, Nucleic Acids Res., 1987, pp. 8125-8148, vol. 15, No. 20.
Kozak, M., Context Effects and Inefficient Initiation at Non-AUG Codons in Eucaryotic Cell-Free Translation Systems, Molecular and Cellular Biology, Nov. 1989, pp. 5073-5080, vol. 9, No. 11.

(Continued)

*Primary Examiner* — Kevin Hill
(74) *Attorney, Agent, or Firm* — TraskBritt, P.C.

(57) ABSTRACT

The invention provides a DNA molecule comprising a multicistronic transcription unit coding for i) a polypeptide of interest, and for ii) a selectable marker polypeptide functional in a eukaryotic host cell, wherein the polypeptide of interest has a translation initiation sequence separate from that of the selectable marker polypeptide, and wherein the coding sequence for the polypeptide of interest is upstream from the coding sequence for the selectable marker polypeptide in the multicistronic transcription unit, and wherein an internal ribosome entry site is present downstream from the coding sequence for the polypeptide of interest and upstream from the coding sequence for the selectable marker polypeptide, and wherein the nucleic acid sequence coding for the selectable marker polypeptide in the coding strand comprises a GTG or a TTG start codon. Also provided are methods for obtaining host cells expressing a polypeptide of interest, such host cells comprising DNA molecules of the invention. Further provided is the production of polypeptides of interest, comprising culturing host cells comprising the DNA molecules of the invention.

3 Claims, 11 Drawing Sheets

(56) References Cited

U.S. PATENT DOCUMENTS

| | | | |
|---|---|---|---|
| 6,586,205 | B1 | 7/2003 | Glucksmann et al. |
| 6,800,457 | B2 | 10/2004 | Koduri et al. |
| 6,872,524 | B1 | 3/2005 | Otte |
| 7,001,772 | B2 | 2/2006 | Roessler et al. |
| 7,192,741 | B2 | 3/2007 | Otte et al. |
| 7,244,609 | B2 | 7/2007 | Drocourt et al. |
| 7,267,965 | B2 | 9/2007 | Otte et al. |
| 7,364,878 | B2 | 4/2008 | Otte et al. |
| 7,655,441 | B2 | 2/2010 | Otte et al. |
| 7,659,094 | B2 | 2/2010 | Otte et al. |
| 7,662,591 | B2 | 2/2010 | Otte et al. |
| 7,736,868 | B2 | 6/2010 | Otte et al. |
| 7,736,869 | B2 | 6/2010 | Otte et al. |
| 7,736,870 | B2 | 6/2010 | Otte et al. |
| 7,749,733 | B2 | 7/2010 | Otte et al. |
| 8,771,984 | B2 * | 7/2014 | Otte et al. .................. 435/69.1 |
| 2002/0155540 | A1 | 10/2002 | Padidam |
| 2003/0138908 | A1 | 7/2003 | Koduri et al. |
| 2003/0166042 | A1 | 9/2003 | Glucksmann et al. |
| 2003/0199468 | A1 | 10/2003 | Otte et al. |
| 2004/0219677 | A1 | 11/2004 | Drocourt et al. |
| 2005/0106609 | A1 | 5/2005 | Otte |
| 2005/0181428 | A1 | 8/2005 | Antoniou et al. |
| 2005/0191723 | A1 | 9/2005 | Otte et al. |
| 2006/0003416 | A1 | 1/2006 | Otte et al. |
| 2006/0010506 | A1 | 1/2006 | Otte et al. |
| 2006/0141577 | A1 | 6/2006 | Otte et al. |
| 2006/0172382 | A1 | 8/2006 | Otte et al. |
| 2006/0195935 | A1 | 8/2006 | Otte et al. |
| 2007/0031933 | A1 | 2/2007 | Otte et al. |
| 2007/0128717 | A1 | 6/2007 | Otte et al. |
| 2007/0212755 | A1 | 9/2007 | Otte et al. |
| 2008/0085537 | A1 | 4/2008 | Otte et al. |
| 2008/0131930 | A1 | 6/2008 | Otte et al. |
| 2008/0206813 | A1 | 8/2008 | Otte et al. |
| 2009/0011468 | A1 | 1/2009 | Otte et al. |
| 2009/0098601 | A1 | 4/2009 | Otte et al. |
| 2010/0136616 | A1 * | 6/2010 | Otte et al. .................. 435/69.1 |
| 2010/0190207 | A1 | 7/2010 | Otte et al. |

FOREIGN PATENT DOCUMENTS

| | | | |
|---|---|---|---|
| WO | WO 91/01374 | | 2/1991 |
| WO | WO 96/04390 | | 2/1996 |
| WO | WO 96/12008 | | 4/1996 |
| WO | WO 97/27207 | | 7/1997 |
| WO | WO 98/11207 | | 3/1998 |
| WO | WO 98/39411 | | 9/1998 |
| WO | WO 98/49289 | | 11/1998 |
| WO | WO 00/05393 | | 2/2000 |
| WO | WO 00/09749 | | 2/2000 |
| WO | WO 00/17337 | | 3/2000 |
| WO | WO 00/23606 | | 4/2000 |
| WO | WO 01/02553 | | 1/2001 |
| WO | WO 01/32901 | A1 | 5/2001 |
| WO | WO 01/57188 | A2 | 8/2001 |
| WO | WO 01/59117 | | 8/2001 |
| WO | WO 01/59118 | | 8/2001 |
| WO | WO 02/24930 | A2 | 3/2002 |
| WO | WO 02/072846 | | 9/2002 |
| WO | WO 02/074969 | | 9/2002 |
| WO | WO 02/099070 | | 12/2002 |
| WO | WO 02/099089 | | 12/2002 |
| WO | WO 03/004704 | | 1/2003 |
| WO | WO 03/083077 | A2 | 10/2003 |
| WO | WO 03/106684 | | 12/2003 |
| WO | WO 2004/027072 | | 4/2004 |
| WO | WO 2004/055215 | A1 | 7/2004 |
| WO | WO 2004/056986 | A2 | 7/2004 |
| WO | WO 94/23046 | | 10/2004 |
| WO | WO 2005/040377 | | 5/2005 |
| WO | WO 2006/005718 | | 1/2006 |
| WO | WO 2006/048459 | | 5/2006 |
| WO | WO 2007/096399 | A2 | 8/2007 |

OTHER PUBLICATIONS

Kozak, M., Point Mutations Define a Sequence Flanking the AUG Initiator Codon that Modulates Translation by Eukaryotic Ribosomes, Cell, Jan. 31, 1986, pp. 283-292, vol. 44.

Kozak, M., Recognition of AUG and alternative initiator codons in augmented by G in position +4 but is not generally affected by the nucleotides in positions +5 and +6, The EMBO Journal, 1997, pp. 2482-2492, vol. 16, No. 9.

Rhazin, CpG methylation, chromatin structure and gene silencing—a three-way connection, The EMBO Journal, 1998, pp. 4905-4908, vol. 17, No. 17.

Bird et al., Methylation-Induced Repression—Belts, Braces and Chromatin, Cell, Nov. 24, 1999, pp. 451-454, vol. 99.

Williams et al., CpG-island fragments from the HNRPA2BI/CBX3 genomics locus reduce sliencing and enhance transgene expression from the hCMV promotor/enhancer in mammalian cells, published Jun. 3, 2005, <http://www.biomedcentral.com/1472-6750/5/17>.

Van Blokland et al., A novel, high stringency selection system allos screening of few clones for high protein expression, Journal of Biotechnology, Sep. 22, 2006, pp. 237-245, vol. 128.

Kwaks et al., Targeting of histone acetyltranscerase domain to a promoter enhances protein expression levels in mammalian cells, Journal of Biotechnology, 2005, pp. 35-46, vol. 115.

Kwaks et al., Employing epigenetics to augment the expression of therapeutic proteins in mammalian cells, Trends in Biotechnology, Mar. 2006, pp. 137-142, vol. 24, No. 3.

Otte et al., Various Expression-Augmenting DNA Elements Benefit from STAR-Select, a Novel High Stringency Selection System from Protein Expression, Biotechnol. Prog., 2007, pp. 801-807, vol. 23.

Aranda et al., Definition of Transcriptional Pause Elements in Fission Yeast, Molecular and Cellular Biology, Feb. 1999, pp. 1251-1261, vol. 19, No. 2.

Auten et al., "Effect of Scaffold Attachment Region on Transgene Expression in Retrovirus Vector-Transduced Primary T cells and Macrophages," Human Gene Therapy, May 20, 1999, pp. 1389-1399, vol. 10, No. 8.

Burgess-Beusse et al., The insulation of genes from external enhancers and silencing chromatin, PNAS, Dec. 10, 2002, pp. 16433-16437, vol. 99, Suppl. 4.

Chan et al., p300-CBP proteins: HATs for transcriptional bridges and scaffolds, Journal of Cell Science, 2001, pp. 2363-2373, vol. 114.

Chung et al., A 5' Element of the Chicken Beta-Globin Domain Serves as an Insulator in Human Erythroid Cells and Protects against Position Effect in *Drosophila*, Aug. 13, 1993, Cell, pp. 505-514, vol. 74.

Database EMBL 'Online! Dec. 15, 1999, "*Homo sapiens* BAC clone RP11-572N21 from 2, complete sequence," XP002359988 retrieved from EBI accession No. EM_PRO:AC018470, database accession No. AC018470, for SEQ ID No. 17.

Database EMBL 'Online! Mar. 15, 1999, "*Homo sapiens* chromosome UNK clone CTA-435J10, working draft sequence, 1 unordered pieces," XP002359997 retrieved from EBI accession No. EM_PRO:AC007044, database accession No. AC007044 for SEQ ID No. 61.

Database EMBL 'Online! Mar. 19, 1998, CIT-HSP-2172C8.TF CIT-HSP *Homo sapiens* genomic clone 2172C8, genomic survey sequence, XP002359995 retrieved from EBI accession No. EM_PRO:B92131, database accession No. B92131 for SEQ ID No. 44.

Database EMBL 'Online! Dec. 23, 1999, "Human DNA sequence from clone RP11-54H19 on chromosome 1 Contains the 3' end of the LMNA gene for lamin A/C, the gene for a novel protein similar to semaphorins (FLJ12287), a novel gene (KIAA0446), the PMF1 gene for polyamine-modulated factor 1, the BGLAP gene for bone gamma-carboxyglutamate (gla) p," XP002359989, retrived from EBI accession No. EM_PRO:AL135927, database accession No. AL135927 for SEQ ID No. 27.

Database EMBL 'Online! Sep. 24, 2000, "*Homo sapiens* chromosome 4 clone RP11-680118, working draft sequence, 25 unordered pieces," XP002359987 retrieved from EBI accession No. EM_PRO:AC080087, database accession No. AC080087 for SEQ ID No. 9.

(56) References Cited

OTHER PUBLICATIONS

Database EMBL 'Online! Apr. 26, 2001, "RST28606 Athersys RAGE Library *Homo sapiens* cDNA, mRNA sequence," XP002359990 retrieved from EBI accession No. EM_PRO:BG209092, database accession No. BG209092 for SEQ ID No. 40.
Database EMBL 'Online! Oct. 28, 1998, "*Homo sapiens* neurexin III-alpha gene, partial cds," XP002359992, retrieved from EBI accession No. EM_PRO:AF099810, database accession No. AF099810 for SEQ ID No. 43.
Database EMBL 'Online! Sep. 29, 1999, "*Homo sapiens* genomic DNA, chromosome 22q11.2, Cat Eye Syndrome region, clone:N64E9," XP002359991, retrieved from EBI accession No. EM_PRO:AP000526, database accession No. AP000526 for SEQ ID No. 40.
Database EMBL 'Online! Sep. 29, 1999, *Homo sapiens* genomic DNA, chromosome 22q11.2, Cat Eye Syndrome region, clone:N14H11, XP002359994 retrieved from EBI accession No. EM_PRO:AP000525, database accession No. AP000525 for SEQ ID No. 44.
Database EMBL 'Online! Sep. 29, 1999, "*Homo sapiens* genomic DNA, chromosome 22q11.2, Cat Eye Syndrome region, clone:c91G6," XP002359996 retrieved from EBI accession No. EM_PRO:AP000528, database accession No. AP000528 for SEQ ID No. 45.
Database EMBL 'Online! Feb. 3, 2004, "Sequence 33099 from Patent W002068579," XP002359986 retrieved from EBI accession No. EM_PRO:CQ747165, database accession No. CQ747165 for SEQ ID No. 9.
Database EMBL 'Online! Aug. 4, 1999, "*Homo sapiens* chromosome 19 clone CTD-2540B15, complete sequence," XP002359985 retrieved from EBI accession No. EM_PRO:AC008738, database accession No. AC008738 for SEQ ID No. 7.
Database EMBL 'Online!, Jul. 8, 1992, *H. sapiens* HOX4B gene upstream sequence XP002348163 retrieved from EBI, Database accession No. X67079, Abstract.
De Boer et al., Portable Shine-Dalgarno regions; nucleotides between the Shine-Dalgarno sequence and the start codon affect the translation efficiency, Gene Amplification and Analysis, 1983, pp. 103-116, vol. 3.
Dummitt et al., "N-Terminal Methionine Removal and Methionine Metabolism in *Saccharomyces cerevisiae*," Journal of Cellular Biochemistry, 2003, pp. 964-974, vol. 89.
Eggermont et al., Poly(A) signals and transcriptional pause sites combine to prevent interference between RNA polymerase II promoters, The EMBO Journal, 1993, pp. 2539-2548, vol. 12, No. 6.
Emery et al., "A chromatin insulator protects retrovirus vectors from chromosomal position effects," Proceedings of the National Academy of Sciences of USA, Aug. 1, 2000, pp. 9150-9155, vol. 97, No. 16.
Farrell et al., Conserved CTCF Insulator Elements Flank the Mouse and Human Beta-Globin Loci, Molecular and Cellular Biology, Jun. 2002, pp. 3820-3831, vol. 22. No. 11.
Han et al., "Matrix attachment regions (MARs) enhance transformation frequency and transgene expression in poplar," Transgenic Research, 1997, pp. 415-420, vol. 6.
Hellen et al., Internal ribosome entry sites in eukaryotic mRNA molecules, Genes and Development, 2001, pp. 1593-1612, vol. 15, No. 13, Cold Spring Harbor Laboratory Press.
Johnson et al., Requirements for utilization of CREB binding protein by hypersensitive site two of the Beta-globin locus control region, Nucleic Acids Research 2002, pp. 1522-1530, vol. 30, No. 7.
Kellum et al., A Group of scs Elements Function as Domain Boundaries in an Enhancer-Blocking Assay, Molecular and Cellular Biology, May 1992, pp. 2424-2431, vol. 12, No. 5.
Kozak, Initiation of translation in prokaryotes and eukaryotes, Gene, 1999, pp. 187-208, vol. 234.
Kozak, Pushing the limits of the scanning mechanism for initiation of translation, Gene, 2002, pp. 1-34, vol. 299.

Kuhn et al., Functional Analysis of the Internal Translation Initiation Site of Foot-and-Mouth Disease Virus, Journal of Virology, Oct. 1990, pp. 4625-4631, vol. 64, No. 10.
Kwaks et al., "Indentification of anti-repressor elements that confer high stable protein in production in mammalian cells," Nature Biotechnology, May 20, 2003, pp. 553-558, vol. 21, No. 5.
Lopez De Quinto et al., Parameters influencing translational efficiency in aphthovirus IRES-based bicistronic expression vectors, Gene, 1998, pp. 51-56, vol. 217.
Maniatis et al., Recognition Sequences of Repressor and Polymerase in the Operators of Bacteriophage Lambda, Cell, Jun. 1975, pp. 109-113, vol. 5.
Martinez-Balbas et al., The acetyltransferase activity of CBP stimulates transcription, The EMBO Journal, 1998, pp. 2886-2893, vol. 17, No. 10.
Mielke et al., "Stabilized, long-term expression of heterodimeric proteins from tricistronic mRNA," Gene, 22 Aug. 2000, pp. 1-8, vol. 254, No. 1-2.
Migliaccio et al., "Stable and unstable transgene integration sites in the human genome: extinction of the Green Fluorescent Protein transgene in K562 cells," Gene, Oct. 3, 2000, pp. 197-214, vol. 256, No. 1-2.
Pile et al., "GAGA Factor-dependent Transcription and Establishment of DNase Hypersensitivity are Independent and Unrelated Events In Vivo," J. of Biological Chemistry, Jan. 14, 2000, pp. 1398-1404, vol. 275, No. 2.
Reik et al., Biotechnologies and therapeutics: Chromatin as a target, Current Opinion in Genetics & Development, 2002, pp. 233-242, vol. 12.
Seum et al., A GAL4-HP1 fusion protein targeted near heterochromatin promotes gene silencing, Chromosoma, 2000, pp. 453-459, vol. 109.
Sigrist et al., "Chromatin Insulator Elements Black the Silencing of a Target Gene by the *Drosophila* Polycomb Response Element (PRE) but Allow trans Interactions Between PREs on Different Chromosomes," Genetics, Sep. 1997, pp. 209-211, vol. 147, No. 1.
Van Der Vlag et al., Transcription Repression Mediated by Polycomb Group Proteins and Other Chromatin-associated Repressors is Selectively Blocked by Insulators, Journal of Biological Chemistry, Jan. 7, 2000, pp. 697-704, vol. 275, No. 1.
West et al., "Insulators: many functions, many mechanisms," Genes and Development, Feb. 1, 2002, pp. 271-288, vol. 16, No. 3.
Bell et al., Insulators and Boundaries: Versatile Regulatory Elements in the Eukaryotic Genome, Science, Jan. 19, 2001, pp. 447-450, vol. 291, No. 5503.
Carroll et al., Translation of Equine Infectious Anemia Virus Bicistronic tat-rev mRNA Requires Leaky Ribosome Scanning of the tat CTG Initiation Codon, J. Virol., 1993. pp. 1433-1440, vol. 67 No. 3, American Society for Microbiology.
Hennecke et al., Composition and arrangement of genes define the strength of IRES-driven translation in bicistronic mRNAs, Nucleic Acids Res., 2001, pp. 3327-3334, vol. 29, No. 16, Oxford University Press.
Kozak, Downstream secondary structure facilitates recognition of initiator codons by eukaryotic ribosomes, PNAS, 1990, pp. 8301-8305, vol. 87, No. 21.
Moser et al., An Update of pTRIDENT Multicistronic Expression Vectors: pTRIDENTs Containing Novel Streptogramin-Responsive Promoters, Biotechnol. Prog., 2000, pp. 724-735, vol. 16, Zurich, Switzerland.
Ress et al., Bicistronic Vector for the Creation of Stable Mammalian Cell Lines that Predisposes All Antibiotic-Resistant Cells to Express Recombinant Protein, Biotechniques, 1996, pp. 102-110, vol. 20, No. 1, Middlesex, UK.
Tang et al., A transformation system for the nonuniversal CUGSer codon usage species *Candida rugosa*, J. Microbiol. Methods, 2003, pp. 231-238, vol. 52.

(56) References Cited

OTHER PUBLICATIONS

Yew et al., CpG-Depleted Plasmid DNA Vectors with Enhanced Safety and Long-Term Gene Expression in Vivo, Molecular Therapy, 2002, pp. 731-773, vol. 5, The American Society of Gene Therapy.
Partial European Search Report, EP 05 07 6209, dated Oct. 7, 2005.
Izumi, et al., Homogeneous Tetracycline-Regulatable Gene Expression in Mammalian Fibroblasts; Journal of Cellular Biochemistry 76; 1999; pp. 280-289.
Kim, et al., Poly(A)-dependent Transcription Termination; The Journal of Biological Chemistry; vol. 278, No. 43; Oct. 24, 2003; pp. 41691-41701.
Lee et al., Engineering Chinese hamster ovary (CHO) cells to achieve an inverse growth-associated production of a foreign protein, β-galactosidase, Cytotechnology, 1998, pp. 73-80, vol. 28.
Liu, et al.; Construction of Discistronic expression vector in mammalian cell with IRES and dhfr; Bull Acad Mil Med Sci, Mar. 2000; vol. 24, No. 1; pp. 9-11, Abstract in English.
PCT International Preliminary Report of Patentability, PCT/EP2007/053984, dated Jul. 25, 2008.
PCT Written Opinion, PCT/EP2007/051696 dated Mar. 5, 2008.
Zeocin™, Instruction Manual, Version J, Aug. 22, 2002.

* cited by examiner

SEQUENCE LISTING

<160> NUMBER OF SEQ ID NOS: 82

<210> SEQ ID NO 1
<211> LENGTH: 749
<212> TYPE: DNA
<213> ORGANISM: Homo sapiens

```
<220> FEATURE:
<221> NAME/KEY: misc_feature
<223> OTHER INFORMATION: sequence of STAR1

<400> SEQUENCE: 1
atgcggtggg ggcgcgccag agactcgtgg gatccttggc ttggatgttt ggatctttct      60
gagttgcctg tgccgcgaaa gacaggtaca tttctgatta ggcctgtgaa gcctcctgga     120
ggaccatctc attaagacga tggtattgga gggagagtca cagaaagaac tgtggcccct     180
ccctcactgc aaaacggaag tgattttatt ttaatgggag ttggaatatg tgagggctgc     240
aggaaccagt ctccctcctt cttggttgga aaagctgggg ctggcctcag agacaggttt     300
tttggccccg ctgggctggg cagtctagtc gaccctttgt agactgtgca caccectaga     360 agagcaacta ccectataca ccaggctggc tcaagtgaaa ggggctctgg ctccagtct      420 ggaaaatctg gtgtcctggg gacctctggt cttgcttctc tcctccoctg cactggctct     480 gggtgcttat ctctgcagaa gcttctcgct agcaaaccca cattcagcgc cctgtagctg     540
aacacagcac aaaaagccct agagatcaaa agcattagta tgggcagttg agcgggaggt     600
gaatatttaa cgcttttgtt catcaataac tcgttggctt tgacctgtct gaacaagtcg     660
agcaataagg tgaaatgcag gtcacagcgt ctaacaaata tgaaaatgtg tatattcacc     720
ccggtctcca gccggcgcgc caggctccc                                       749

<210> SEQ ID NO 2
<211> LENGTH: 883
<212> TYPE: DNA
<213> ORGANISM: Homo sapiens
<220> FEATURE:
<221> NAME/KEY: misc_feature
<223> OTHER INFORMATION: sequence of STAR2

<400> SEQUENCE: 2
gggtgcttcc tgaattcttc cctgagaagg atggtggccg gtaaggtccg tgtaggtggg      60
gtgcggctcc ccaggccccg gcccgtggtg gtggccgctg cccagcggcc cggcaccccc     120
atagtccatg gcgcccgagg cagcgtgggg gaggtgagtt agaccaaaga gggctggccc     180
ggagttgctc atgggctcca catagctgcc ccccacgaag acgggcttc cctgtatgtg      240 tggggtccca tagctgccgt tgccctgcag gccatgagcg tgcgggtcat agtcggggt      300 gcccoctgcg cccgccoctg ccgccgtgta gcgcttctgt gggggtggcg ggggtgcgca     360
gctgggcagg gacgcagggt aggaggcggg gggcagcccg taggtacct ggggggggctt      420 ggagaagggc gggggcgact ggggctcata cgggacgctg ttgaccagcg aatgcataga     480
gttcagatag ccaccggctc cggggggcac ggggctgcga cttggagact ggccccccga     540
tgacgttagc atgcccttgc ccttctgatc ctttttgtac ttcatgcggc gattctggaa     600
ccagatcttg atctggcgct cagtgaggtt cagcagattg ccatctcca cccggcgcgg      660 ccggcacagg tagcggttga agtggaactc tttctccagc tccaccagct gcgcgctcgt     720
gtaggccgtg cgcgcgcgct tggacgaagc ctgccccggc gggctcttgt cgccagcgca     780
gctttcgcct gcgaggacag agagaggaag agcggcgtca ggggctgccg cggccccgcc     840
cagcccctga cccagcccgg cccctccttc caccaggccc caa                       883

<210> SEQ ID NO 3
<211> LENGTH: 2126
<212> TYPE: DNA
<213> ORGANISM: Homo sapiens
<220> FEATURE:
```

<221> NAME/KEY: misc_feature
<223> OTHER INFORMATION: sequence of STAR3

<400> SEQUENCE: 3

| | | | | | |
|---|---|---|---|---|---|
| atctcgagta | ctgaaatagg | agtaaatctg | aagagcaaat | aagatgagcc | agaaaaccat | 60 |
| gaaaagaaca | gggactacca | gttgattcca | caaggacatt | cccaaggtga | gaaggccata | 120 |
| tacctccact | acctgaacca | attctctgta | tgcagattta | gcaaggttat | aaggtagcaa | 180 |
| aagattagac | ccaagaaaat | agagaacttc | caatccagta | aaaatcatag | caaatttatt | 240 |
| gatgataaca | attgtctcca | aaggaacaag | gcagagtcgt | gctagcagag | gaagcacgtg | 300 |
| agctgaaaac | agccaaatct | gctttgtttt | catgacacag | gagcataaag | tacacaccac | 360 |
| caactgacct | attaaggctg | tggtaaaccg | attcatagag | agaggttcta | aatacattgg | 420 |
| tccctcacag | gcaaactgca | gttcgctccg | aacgtagtcc | ctggaaattt | gatgtccagt | 480 |
| atagaaaagc | agagcagtca | aaaaatatag | ataaagctga | accagatgtt | gcctgggcaa | 540 |
| tgttagcagc | accacactta | agatataacc | tcaggctgtg | gactccctcc | ctggggagcg | 600 |
| gtgctgccgg | cggcgggcgg | gctccgcaac | tccccggctc | tctcgcccgc | cctcccgttc | 660 |
| tcctcgggcg | gcggcggggg | ccgggactgc | gccgctcaca | gcggcggctc | ttctgcgccc | 720 |
| ggcctcggag | gcagtggcgg | tggcggccat | ggcctcctgc | gttcgccgat | gtcagcattt | 780 |
| cgaactgagg | gtcatctcct | tgggactggt | tagacagtgg | gtgcagccca | cggagggcga | 840 |
| gttgaagcag | ggtggggtgt | cacctccccc | aggaagtcca | gtgggtcagg | gaactccctc | 900 |
| ccctagccaa | gggaggccgt | gagggactgt | gcccggtgag | agactgtgcc | ctgaggaaag | 960 |
| gtgcactctg | gcccagatac | tacactttc | ccacggtctt | caaaacccgc | agaccaggag | 1020 |
| attccctcgg | gttcctacac | caccaggacc | ctgggtttca | accacaaaac | cgggccattt | 1080 |
| gggcagacac | ccagctagct | gcaagagttg | ttttttttt | tatactcctg | tggcacctgg | 1140 |
| aacgccagcg | agagcacc | tttcactccc | ctggaaaggg | ggctgaaggc | agggaccttt | 1200 |
| agctgcgggc | tagggggttt | ggggttgagt | ggggagggg | agagggaaaa | ggcctcgtca | 1260 |
| ttggcgtcgt | ctgcagccaa | taaggctacg | ctcctctgct | gcgagtagac | ccaatccttt | 1320 |
| cctagaggtg | gaggggggcgg | gtaggtggaa | gtagaggtgg | cgcggtatct | aggagagaga | 1380 |
| aaaagggctg | gaccaatagg | tgcccggaag | aggcggaccc | agcggtctgt | tgattggtat | 1440 |
| tggcagtgga | ccctcccccg | gggtggtgcc | ggagggggg | atgatgggtc | gaggggtgtg | 1500 |
| tttatgtgga | agcgagatga | ccggcaggaa | cctgccccaa | tgggctgcag | agtggttagt | 1560 |
| gagtgggtga | cagacagacc | cgtaggccaa | cgggtggcct | taagtgtctt | tggtctcctc | 1620 |
| caatggagca | gcggcggggc | gggaccgcga | ctcgggttta | atgagactcc | attgggctgt | 1680 |
| aatcagtgtc | atgtcggatt | catgtcaacg | acaacaacag | ggggacacaa | aatggcggcg | 1740 |
| gcttagtcct | accccctggcg | gcggcggcag | cggtggcgga | ggcgacggca | ctcctccagg | 1800 |
| cggcagccgc | agtttctcag | gcagcggcag | cgccccccgc | aggcgcggtg | gcggtggcgc | 1860 |
| gcagccaggt | ctgtcaccca | ccccgcgcgt | tcccaggggg | aggagactgg | gcgggagggg | 1920 |
| ggaacagacg | gggggggatt | caggggcttg | cgacgcccct | cccacaggcc | tctgcgcgag | 1980 |
| ggtcaccgcg | gggccgctcg | gggtcaggct | gcccctgagc | gtgacggtag | ggggcggggg | 2040 |
| aaagggagg | agggacaggc | cccgcccctc | ggcagggcct | ctagggcaag | ggggcggggc | 2100 |
| tcgaggagcg | gaggggggcg | gggcgg | | | | 2126 |

<210> SEQ ID NO 4

<211> LENGTH: 1625
<212> TYPE: DNA
<213> ORGANISM: Homo sapiens
<220> FEATURE:
<221> NAME/KEY: misc_feature
<223> OTHER INFORMATION: sequence of STAR4

<400> SEQUENCE: 4

```
gatctgagtc atgttttaag gggaggattc ttttggctgc tgagttgaga ttaggttgag      60
ggtagtgaag gtaaaggcag tgagaccacg tagggggtcat tgcagtaatc caggctggag    120
atgatggtgg ttcagttgga atagcagtgc atgtgctgta acaacctcag ctgggaagca    180
gtatatgtgg cgttatgacc tcagctggaa cagcaatgca tgtggtggtg taatgacccc    240
agctgggtag ggtgcatgtg gtgtaacgac ctcagctggg tagcagtgtg tgtgatgtaa    300
caacctcagc tgggtagcag tgtacttgat aaaatgttgg catactctag atttgttatg    360
agggtagtgc cattaaattt ctccacaaat tggttgtcac gtatgagtga aagaggaag     420
tgatggaaga cttcagtgct tttggcctga ataaatagaa gacgtcattt ccagttaatg    480
gagacaggga agactaaagg tagggtggga ttcagtagag caggtgttca gttttgaata    540
tgatgaactc tgagagagga aaaacttttt ctacctctta gttttgtga ctggacttaa     600
gaattaaagt gacataagac agagtaacaa gacaaaaata tgcgaggtta tttaatattt    660
ttacttgcag aggggaatct tcaaaagaaa aatgaagacc caagaagcc attagggtca     720
aaagctcata tgccttttta agtagaaaat gataaatttt aacaatgtga aagacaaag     780
gtgtttgagc tgagggcaat aaattgtggg acagtgatta agaaatatat gggggaaatg    840
aaatgataag ttattttagt agatttattc ttcatatcta ttttggcttc aacttccagt    900
ctctagtgat aagaatgttc ttctcttcct ggtacagaga gagcaccttt ctcatgggaa    960
atttatgac cttgctgtaa gtagaaaggg gaagatcgat ctcctgtttc ccagcatcag    1020
gatgcaaaca tttcccctcca ttccagttct caacccatg gctgggcctc atggcattcc    1080
agcatcgcta tgagtgcacc tttcctgcag gctgcctcgg gtagctggtg cactgctagg   1140
tcagtctatg tgaccaggag ctgggcctct gggcaatgcc agttggcagc ccccatccct   1200
ccactgctgg gggcctccta tccagaaggg cttggtgtgc agaacgatgg tgcaccatca   1260
tcattcccca cttgccatct ttcagggac agccagctgc tttgggcgcg gcaaaaaaca    1320
cccaactcac tcctcttcag gggcctctgg tctgatgcca ccacaggaca tccttgagtg   1380
ctgggcagtc tgaggacagg gaaggagtga tgaccacaaa acaggaatgg cagcagcagt   1440
gacaggagga agtcaaaggc ttgtgtgtcc tggccctgct gagggctggc gagggccctg   1500
ggatggcgct cagtgcctgg tcggctgcaa gaggccagcc ctctgcccat gaggggagct   1560
ggcagtgacc aagctgcact gccctggtgg tgcatttcct gccccactct ttccttctaa   1620
gatcc                                                               1625
```

<210> SEQ ID NO 5
<211> LENGTH: 1571
<212> TYPE: DNA
<213> ORGANISM: Homo sapiens
<220> FEATURE:
<221> NAME/KEY: misc_feature
<223> OTHER INFORMATION: sequence of STAR5

<400> SEQUENCE: 5

```
cacctgattt aaatgatctg tctggtgagc tcactgggtc tttactcgca tgctgggtcc      60
acagctccac tgtcctgcag ggtccgtgag tgtgggcccc ttatctattt catcatcata    120
```

```
accctgcgtg tcctcaactc ctggcacata ttgggtggcc ccatccacac acggttgttg      180
agtgaatcca tgagatgaca aaggctatga tgtagactat atcatgagcc agaaccaggc      240
tttcctacct ccagacaatc aagggccttg atttgggatt gagggagaaa ggagtagaag      300
ccaggaagga gaagagattg aggtttacca agggtgcaaa gtcctggccc ctgactgtag      360
gctgaaaact atagaaatga tagaacaatt ttgcaatgaa atgcagaaga ccctgcatca      420
actttaggtg ggacttcggg tattttatg gccacagaac atcctcccat ttacctgcat       480
ggcccagaca cagacttcaa aacagttgag gccagcaggc tccaggtaag tggtaggatt      540
ccagaatgcc ctcagagtgt tgtgggaggc agcaggcgat tttcctggac ttctgagttt      600
atgagaaccc caaaccccaa ttggcattaa cattgaggtc tcaatgtatc atggcaggaa      660
gcttccgagt ggtgaaaagg aaagtgaaca tcaaagctcg gaagacaaga gggtggagtg      720
atggcaacca agagcaagac ccttccctct cctgtgatgg ggtggctcta tgtgaagccc      780
ccaaactgga cacaggtctg gcagaatgag gaacccactg agatttagcg ccaacatcca      840
gcataaaagg gagactgaca tagaatttga gttagttaaa aataaggcac aatgcttttc       900
atgtattcct gagttttgtg gactggtgtt caatttgcag cattcttagt tgattaaatc      960
tgagatgaag aaagagtgtc caacactttc accttggaaa gctctggaaa agcaaaaggg     1020
agagacaatt agcttcatcc attaactcac ttagtcatta tgcattcatt catgtaacta     1080
ccaaacacgt actgagtgcc taacactcct gagacactga gaagtttctt gggaatacaa     1140
agatgaataa aaaccacgcc aggcaggagt tggaggaagg ttctggatgc caccacgctc     1200
tacctcctgg ctggacacca ggcaatgttg gtaaccttct gcctccaatt tctgcaaata     1260
cataattaat aaacacaagg ttatcttcta aacagttctt aaaatgagtc aactttgttt     1320
aaacttgttc tttttagaga aaaatgtatt tttgaaagag ttggttagtg ctaggggaaa     1380
tgtctgggca cagctcagtc tggtgtgaga gcaggaagca gctctgtgtg tctggggtgg     1440
gtacgtatgt aggacctgtg ggagaccagg ttggggggaag gcccctcctc atcaagggct     1500
cctttgcttt ggtttgcttt ggcgtgggag gtgctgtgcc acaagggaat acgggaaata     1560
agatctctgc t                                                          1571

<210> SEQ ID NO 6
<211> LENGTH: 1173
<212> TYPE: DNA
<213> ORGANISM: Homo sapiens
<220> FEATURE:
<221> NAME/KEY: misc_feature
<223> OTHER INFORMATION: sequence of STAR6

<400> SEQUENCE: 6
tgacccacca cagacatccc ctctggcctc ctgagtggtt tcttcagcac agcttccaga       60
gccaaattaa acgttcactc tatgtctata gacaaaaagg gttttgacta aactctgtgt      120
tttagagagg gagttaaatg ctgttaactt tttaggggtg ggcgagaggg atgacaaata     180
acaacttgtc tgaatgtttt acatttctcc ccactgcctc aagaaggttc acaacgaggt     240
catccatgat aaggagtaag acctcccagc cggactgtcc ctcggccccc agaggacact     300
ccacagagat atgctaactg gacttggaga ctggctcaca ctccagagaa aagcatggag     360
cacgagcgca cagagcaggg ccaaggtccc agggacagaa tgtctaggag ggagattggg     420
gtgagggtaa tctgatgcaa ttactgtggc agctcaacat tcaagggagg gggaagaaag     480
aaacagtccc tgtcaagtaa gttgtgcagc agagatggta agctccaaaa tttgaaactt     540
```

| | |
|---|---|
| tggctgctgg aaagttttag ggggcagaga taagaagaca taagagactt tgagggttta | 600 |
| ctacacacta gacgctctat gcatttattt atttattatc tcttatttat tactttgtat | 660 |
| aactcttata ataatcttat gaaaacggaa accctcatat acccatttta cagatgagaa | 720 |
| aagtgacaat tttgagagca tagctaagaa tagctagtaa gtaaaggagc tgggacctaa | 780 |
| accaaaccct atctcaccag agtacacact cttttttttt ttccagtgta attttttta | 840 |
| attttttattt tactttaagt tctgggatac atgtgcagaa ggtatggttt gttacatagg | 900 |
| tatatgtgtg ccatagtgga ttgctgcacc tatcaacccg tcatctaggt ttaagcccca | 960 |
| catgcattag ctatttgtcc tgatgctctc cctcccctcc ccacaccaga caggccttgg | 1020 |
| tgtgtgatgt tcccctccct gtgtccatgt gttctcactg ttcagctccc acttatgagt | 1080 |
| gagaacgtgt ggtatttggt tttctgttcc tgtgttagtt tgctgaggat gatggcttcc | 1140 |
| agcttcatcc atgtccctgc aaaggacacg atc | 1173 |

<210> SEQ ID NO 7
<211> LENGTH: 2101
<212> TYPE: DNA
<213> ORGANISM: Homo sapiens
<220> FEATURE:
<221> NAME/KEY: misc_feature
<223> OTHER INFORMATION: sequence of STAR7

<400> SEQUENCE: 7

| | |
|---|---|
| aggtgggtgg atcacccgag gtcaggagtt caagaccagc ctggccaaca tggtaaaacc | 60 |
| tcgtctctac taaaaatac gaaaaattag ctggttgtgg tggtgcgtgc ttgtaatccc | 120 |
| agctactcgg gaggctgagg caggagaatc acttgaatct gggaggcaga ggttgcagtg | 180 |
| agctgagata gtgccattgc actccagcct gggcaacaga cggagactct gtctccaaaa | 240 |
| aaaaaaaaaa aaatcttaga ggacaagaat ggctctctca aacttttgaa gaaagaataa | 300 |
| ataaattatg cagttctaga agaagtaatg gggatatagg tgcagctcat gatgaggaag | 360 |
| acttagctta acttttcataa tgcatctgtc tggcctaaga cgtggtgagc ttttatgtc | 420 |
| tgaaaacatt ccaatataga atgataataa taatcacttc tgaccccct tttttttcct | 480 |
| ctccctagac tgtgaagcag aaaccccata ttttttcttag ggaagtggct acgcactttg | 540 |
| tatttatatt aacaactacc ttatcaggaa attcatattg ttgcccttttt atggatgggg | 600 |
| aaactggaca agtgacagag caaaatccaa acacagctgg ggatttccct cttttagatg | 660 |
| atgattttaa aagaatgctg ccagagagat tcttgcagtg ttggaggaca tatatgacct | 720 |
| ttaagatatt ttccagctca gagatgctat gaatgtatcc tgagtgcatg gatggacctc | 780 |
| agttttgcag attctgtagc ttatacaatt tggtggtttt ctttagaaga aaataacaca | 840 |
| tttataaata ttaaaatagg cccaagacct tacaagggca ttcatacaaa tgagaggctc | 900 |
| tgaagtttga gtttgttcac tttctagtta attatctcct gcctgtttgt cataaatgcg | 960 |
| tttagtaggg agctgctaat gacaggttcc tccaacagag tgtggaagaa ggagatgaca | 1020 |
| gctggcttcc cctctgggac agcctcagag ctagtgggga aactatgtta gcagagtgat | 1080 |
| gcagtgacca agaaaatagc actaggagaa agctggtcca tgagcagctg gtgagaaaag | 1140 |
| gggtggtaat catgtatgcc ctttcctgtt ttatttttta ttgggtttcc ttttgcctct | 1200 |
| caattccttc tgacaataca aaatgttggt tggaacatgg agcacctgga agtctggttc | 1260 |
| attttctctc agtctcttga tgttctctcg ggttcactgc ctattgttct cagttctaca | 1320 |
| cttgagcaat ctcctcaata gctaaagctt ccacaatgca gattttgtga tgacaaattc | 1380 |

| | |
|---|---|
| agcatcaccc agcagaactt aggtttttt ctgtcctccg tttcctgacc tttttcttct | 1440 |
| gagtgcttta tgtcacctcg tgaaccatcc tttccttagt catctaccta gcagtcctga | 1500 |
| ttcttttgac ttgtctccct acaccacaat aaatcactaa ttactatgga ttcaatccct | 1560 |
| aaaatttgca caaacttgca aatagattac gggttgaaac ttagagattt caaacttgag | 1620 |
| aaaaaagttt aaatcaagaa aaatgacctt taccttgaga gtagaggcaa tgtcatttcc | 1680 |
| aggataatt ataataatat tgtgtttaat atttgtatgt aacatttgaa taccttcaat | 1740 |
| gttcttattt gtgttatttt aatctcttga tgttactaac tcatttggta gggaagaaaa | 1800 |
| catgctaaaa taggcatgag tgtcttatta aatgtgacaa gtgaatagat ggcagaaggt | 1860 |
| ggattcatat tcagttttcc atcaccctgg aaatcatgcg gagatgattt ctgcttgcaa | 1920 |
| ataaaactaa cccaatgagg ggaacagctg ttcttaggtg aaaacaaaac aaacacgcca | 1980 |
| aaaacctta ttctctttat tatgaatcaa attttcctc tcagataatt gttttattta | 2040 |
| tttattttta ttattattgt tattatgtcc agtctcactc tgtcgcctaa gctggcatga | 2100 |
| t | 2101 |

<210> SEQ ID NO 8
<211> LENGTH: 1821
<212> TYPE: DNA
<213> ORGANISM: Homo sapiens
<220> FEATURE:
<221> NAME/KEY: misc_feature
<223> OTHER INFORMATION: sequence of STAR8

<400> SEQUENCE: 8

| | |
|---|---|
| gagatcacct cgaagagagt ctaacgtccg taggaacgct ctcgggttca caaggattga | 60 |
| ccgaacccca ggtacgtcg ctctccatct gaggcttgct ccaaatggcc ctccactatt | 120 |
| ccaggcacgt gggtgtctcc cctaactctc cctgctctcc tgagcccatg ctgcctatca | 180 |
| cccatcggtg caggtccttt ctgaagagct cgggtggatt ctctccatcc cacttccttt | 240 |
| cccaagaaag aagccaccgt tccaagacac ccaatgggac attccccttc cacctccttc | 300 |
| tccaaagttg cccaggtgtt catcacaggt tagggagaga agcccccagg tttcagttac | 360 |
| aaggcatagg acgctggcat gaacacacac acacacacac acacacacac acacacacac | 420 |
| acacgactcg aagaggtagc cacaagggtc attaaacact tgacgactgt tttccaaaaa | 480 |
| cgtggatgca gttcatccac gccaaagcca agggtgcaaa gcaaacacgg aatggtggag | 540 |
| agattccaga ggctcaccaa accctctcag gaatattttc ctgaccctgg ggcagaggt | 600 |
| tggaaacatt gaggacattt cttgggacac acggagaagc tgaccgacca ggcatttcc | 660 |
| tttccactgc aaatgaccta tggcgggggc atttcacttt ccctgcaaa tcacctatgg | 720 |
| cgaggtacct ccccaagccc ccacccccac ttccgcgaat cggcatggct cggcctctat | 780 |
| ccgggtgtca ctccaggtag gcttctcaac gctctcggct caaagaagga caatcacagg | 840 |
| tccaagccca aagcccacac ctcttccttt tgttataccc acagaagtta gagaaaacgc | 900 |
| cacactttga gacaaattaa gagtcccttta tttaagccgg cggccaaaga gatggctaac | 960 |
| gctcaaaatt ctctgggccc cgaggaaggg gcttgactaa cttctatacc ttggtttagg | 1020 |
| aaggggaggg gaactcaaat gcggtaattc tacagaagta aaaacatgca ggaatcaaaa | 1080 |
| gaagcaaatg gttatagaga gataaacagt tttaaaggc aaatggttac aaaaggcaac | 1140 |
| ggtaccaggt gcggggctct aaatccttca tgacacttag atataggtgc tatgctggac | 1200 |
| acgaactcaa ggctttatgt tgttatctct tcgagaaaaa tcctgggaac ttcatgcact | 1260 |

```
gtttgtgcca gtatcttatc agttgattgg gctcccttga aatgctgagt atctgcttac    1320
acaggtcaac tccttgcgga aggggttgg gtaaggagcc cttcgtgtct cgtaaattaa     1380
ggggtcgatt ggagtttgtc cagcattccc agctacagag agccttattt acatgagaag   1440
caaggctagg tgattaaaga gaccaacagg gaagattcaa agtagcgact tagagtaaaa   1500
acaaggttag gcatttcact ttcccagaga acgcgcaaac attcaatggg agagaggtcc   1560
cgagtcgtca aagtcccaga tgtggcgagc ccccgggagg aaaaaccgtg tcttccttag   1620
gatgcccgga acaagagcta ggcttccgga gctaggcagc catctatgtc cgtgagccgg   1680
cgggagggag accgcgggaa ggcgaagtgg ggcggggcca tccttctttc tgctctgctg   1740
ctgccgggga gctcctggct ggcgtccaag cggcaggagg ccgccgtcct gcagggcgcc   1800
gtagagtttg cggtgcagag t                                              1821

<210> SEQ ID NO 9
<211> LENGTH: 1929
<212> TYPE: DNA
<213> ORGANISM: Homo sapiens
<220> FEATURE:
<221> NAME/KEY: misc_feature
<223> OTHER INFORMATION: sequence of STAR9

<400> SEQUENCE: 9
cacttcctgg gagtggagca gaggctctgc gtggagcatc catgtgcagt actcttaggt     60
acggaaggga ttgggctaaa ccatggatgg gagctgggaa gggaagggac caacttcagg    120
ccccactggg acactggagc tgccacccct tagagccctc ctaaccctac accagaggct    180 gaggggggacc tcagacatca cacacatgct ttcccatgtt ttcagaaatc tggaaacgta   240
gaacttcagg ggtgagagtg cctagatatt gaatacaagg ctagattggg cttctgtaat    300
atcccaaagg accctccagc ttttcacca gcacctaatg cccatcagat accaaagaca     360
cagcttagga gaggttcacc ctgaagctga ggaggaggca gccggattag agttgactga    420
gcaaggatga ctgccttctc cacctgacga tttcagctgc tgccctttc ttttcctggg     480 aatgcctgtc gccatggcct tctgtgtcca caggagagtt tgacccagat actcatggac    540
caggcaaagg tgctgttcct cccagcccag ggcccaccat gaagcatgcc tgggagcctg    600
gtaaggaccc agccactcct gggctgttga cattggcttc tcttgcccag cattgtagcc    660
acgccactgc attgtactgt gagataagtc aaggtgggct caccaggacc tgcactaaat   720
tgtgaaattc agctccaaag aactttggaa attacccatg catttaagca aaatgaatga   780
tacctgagca aacccttca cattggcaca agttacaatc ctgtctcatc ctcttgatta    840
caaattccat ccaggcaaga gctgtatcac cctgaggtct ccccattcat gttttggtca   900
ataatattta gtttcctttt gaaaatagat ttttgtgtta ctccattatg atgggcagag   960
gccagatgct tatattctat ttaaatgact atgtttttct atctgtaact gggtttgtgt   1020
tcaggtggta aatgcttttt ttttgcagtc agaagattcc tggaaggcga ccagaaatta   1080
gctggccgct gtcagacctg aagttacttc taaagggcct ttagaaatga attctttttt   1140
atgccttctc tgaattctga gaagtaggct tgacttcccc taagtgtgga gttgggagtc   1200
aactcttctg aaaagaaagt ttcagagcat tttccaaagc catggtcagc tgtgggaagg   1260
gaagacgatg gatagtacag ttgccggaaa acactgatgg aggcggatgc tccagctcag   1320
ccaaagacct ttgttctgcc caccccagaa atgcccttc ctcaatcgca gaaacgttgc    1380
cccatggctc ctgatactca gaatgcagcc tctgaccagg accatctgca tcctccagga   1440
```

```
gctcgtaaga aatgcagcat cgtgggacct gctggcacct ggtgaaccca aacctgcagg    1500
gctcctgggt gtgcttgggg cggctgcagg ggaagaggga gtcagcagcc tcctcctgac    1560
cttcccgggg gctgcttttc tgaggggcca gaatgcaccg gttgaccttg ttgcatcact    1620
ggcccatgac tggctgcttt ggtcaggtgt aaaaaggtgt ttccagaggg tctgctcctc    1680
tcactatcgg accaggtttc catggagagc tcagcctccc agcaaggata gagaacttca    1740
aatggctcaa agaactgaga ggccacacat gtgtgacctg aatagtctct gctgcaaaac    1800
aaagggtttc ttaatgtaaa acgttctctt cctcacagag gggttcccag ctgctagtgg    1860
gcatgttgca ggcatttcct gggctgcatc aggttgtcat aagccagagg atcattttg    1920 ggggctcat                                                            1929

<210> SEQ ID NO 10
<211> LENGTH: 1167
<212> TYPE: DNA
<213> ORGANISM: Homo sapiens
<220> FEATURE:
<221> NAME/KEY: misc_feature
<223> OTHER INFORMATION: sequence of STAR10
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t

<400> SEQUENCE: 10
aggtcaggag ttcaagacca gcctggccaa catggtgaaa ccctgtccct acaaaaaata    60
caaaaattag ccgggcgtgg tgggggcgc ctataatccc agctactcag gatgctgaga    120
caggagaatt gtttgaaccc gggaggtgga ggttgcagtg aactgagatc gcgccactgc    180
actccagcct ggtgacagag agagactccg tctcaacaac agacaaacaa acaaacaaac    240
aacaacaaaa atgtttactg acagctttat tgagataaaa ttcacatgcc ataaaggtca    300
ccttctacag tatacaattc agtggattta gtatgttcac aaagttgtac gttgttcacc    360
atctactcca gaacatttac atcaccccta aaagaagctc tttagcagtc acttctcatt    420
ctccccagcc cctgccaacc acgaatctac tntctgtctc tattctgaat atttcatata    480
aaggagtcct atcatatggg cctttacgt ctaccttctt tcacttagca tcatgttttt    540
aagattcatc cacagtgtag cacgtgtcag ttaattcatt tcatcttatg ctggataat    600 gctctattgt atgcatatcc ctcactttgc ttatccattc atcaactgat tgacatttgg    660
gttatttcta cttttgact attatgagta atgctgctat gaacattcct gtaccaatcg    720
ttacgtggac atatgctttc aattctcctg agtatgtaac tagggttgga gttgctgggt    780
catatgttaa ctcagtgttt catttttttg aagaactacc aaatggtttt ccaaagtgga    840
tgcaacactt tacattccca ccagcaagat atgaaggttc caatgtctct acattttgc    900 caacacttgt gattttcttt tatttattta tttatttatt tattttgag atggagtctc    960 actctgtcac ccaggctgga gtgcagtggc acaatttcag ctcactgcaa tctccacctc    1020
tcgggctcaa gcgatactcc tgcctcaacc tcccgagtaa ctgggattac aggcgcccac    1080
caccacacca gctaatttt ttgtatttt agtagagacg gggtttcatc atgtcggcca    1140
ggntgtactc gaactctgac ctcaagt                                        1167
```

<210> SEQ ID NO 11
<211> LENGTH: 1377
<212> TYPE: DNA
<213> ORGANISM: Homo sapiens
<220> FEATURE:
<221> NAME/KEY: misc_feature
<223> OTHER INFORMATION: sequence of STAR11

<400> SEQUENCE: 11

| | | | | | |
|---|---|---|---|---|---|
| aggatcactt | gagcccagga | gttcaagacc | agcctgggca | acatagcgag | aacatgtctc | 60 |
| aaaaaggaaa | aaaatggggg | aaaaaaccct | cccagggaca | gatatccaca | gccagtcttg | 120 |
| ataagctcca | tcattttaaa | gtgcaaggcg | gtgcctccca | tgtggatgat | tatttaatcc | 180 |
| tcttgtactt | tgtttagtcc | tttgtggaaa | tgcccatctt | ataaattaat | agaattctag | 240 |
| aatctaatta | aaatggttca | actctacatt | ttactttagg | ataatatcag | gaccatcaca | 300 |
| gaatgtctga | gatgtggatt | taccctatct | gtagctcact | tcttcaacca | ttcttttagc | 360 |
| aaggctagtt | atcttcagtg | acaaccccatt | gctgccctct | actatctcct | ccctcagatg | 420 |
| gactactctg | attaagcttg | agctagaata | agcatgttat | cccgggattt | catatggaat | 480 |
| attttataca | tgagtgagcc | attatgagtt | gtttgaaaat | ttattatgtt | gagggagggt | 540 |
| aaccgctgta | acaaccatca | ccaaatctaa | tcgactgaat | acatttgacg | tttatttctt | 600 |
| gttcacctga | cagttcagtg | ttacctaaat | ttacatgaag | acccagaggc | ccacgctcct | 660 |
| tcattttggg | ctccaccgac | ctccaaggtt | tcagggccct | ctgccccgcc | ttctgcaccc | 720 |
| acagggaag | agagtggagg | atgcacacgc | ccaggcctgg | aagtgacgca | tgtggcttcc | 780 |
| ccgtccacag | acttcaccca | cagtccattg | gccttcttaa | gtcatggact | cctgctgagc | 840 |
| tgccagggtg | catgggaaat | ccatgtgact | gtgtgccctg | gaggaagggg | agcgtttcgg | 900 |
| tgagcacaca | ggagtctttg | ccactagacg | ctgatgagga | ttccccacag | gcgatgaagc | 960 |
| atggagactc | atcttgtaac | aaacagatga | gttgttgaca | tctcttaagt | ttactttgtg | 1020 |
| tgcagttttt | attcagatag | gaaaggctgt | taaaatctta | acacctaact | ggaagaaggg | 1080 |
| ttttagagaa | gtgtggtttt | cagtaagcca | gttctttcca | caatccaaga | aacgaaataa | 1140 |
| atttccagca | tggagcagtt | ggcaggtaag | gttttgttg | tggtctcgcc | caggcttgag | 1200 |
| tgtaaccggt | gtggtcatag | ctcactacat | tctcaaactc | ctggccttaa | gtcatcctcc | 1260 |
| tgcctcagcc | tcccaaaggc | aagtaaggtt | aagaataggg | gaaaggtgaa | gtttcacagc | 1320 |
| ttttctagaa | ttctttttat | tcaagggact | ctcagatcat | caaacccacc | cagaatc | 1377 |

<210> SEQ ID NO 12
<211> LENGTH: 1051
<212> TYPE: DNA
<213> ORGANISM: Homo sapiens
<220> FEATURE:
<221> NAME/KEY: misc_feature
<223> OTHER INFORMATION: sequence of STAR12

<400> SEQUENCE: 12

| | | | | | |
|---|---|---|---|---|---|
| atcctgcttc | tgggaagaga | gtggcctccc | ttgtgcaggt | gactttggca | ggaccagcag | 60 |
| aaacccaggt | ttcctgtcag | gaggaagtgc | tcagcttatc | tctgtgaagg | gtcgtgataa | 120 |
| ggcacgagga | ggcagggggct | tgccaggatg | ttgccttct | gtgccatatg | ggacatctca | 180 |
| gcttacgttg | ttaagaaata | tttggcaaga | agatgcacac | agaatttctg | taacgaatag | 240 |
| gatggagttt | taagggttac | tacgaaaaaa | agaaaactac | tggagaagag | ggaagccaaa | 300 |
| caccaccaag | tttgaaatcg | attttattgg | acgaatgtct | cactttaaat | ttaaatggag | 360 |

```
tccaacttcc tttttctcacc cagacgtcga gaaggtggca ttcaaaatgt ttacacttgt    420
ttcatctgcc tttttgctaa gtcctggtcc cctacctcct ttccctcact tcacatttgt    480
cgtttcatcg cacacatatg ctcatcttta tatttacata tatataattt ttatatatgg    540
cttgtgaaat atgccagacg agggatgaaa tagtcctgaa aacagctgga aaattatgca    600
acagtgggga gattgggcac atgtacattc tgtactgcaa agttgcacaa cagaccaagt    660
ttgttataag tgaggctggg tggtttttat tttttctcta ggacaacagc ttgcctggtg    720
gagtaggcct cctgcagaag gcatttctt aggagcctca acttccccaa gaagaggaga    780
gggcgagact ggagttgtgc tggcagcaca gagacaaggg ggcacggcag gactgcagcc    840
tgcagagggg ctggagaagc ggaggctggc acccagtggc cagcgaggcc caggtccaag    900
tccagcgagg tcgaggtcta gagtacagca aggccaaggt ccaaggtcag tgagtctaag    960
gtccatggtc agtgaggctg agacccaggg tccaatgagg ccaaggtcca gagtccagta   1020
aggccgagat ccagggtcca gggaggtcaa g                                  1051
```

<210> SEQ ID NO 13
<211> LENGTH: 1291
<212> TYPE: DNA
<213> ORGANISM: Homo sapiens
<220> FEATURE:
<221> NAME/KEY: misc_feature
<223> OTHER INFORMATION: sequence of STAR13

<400> SEQUENCE: 13

```
agccactgag gtcctaactg cagccaaggg gccgttctgc acatgtcgct caccctctgt     60
gctctgttcc ccacagagca aacgcacatg caacgttgg tccgctcagc cactggttct    120
gtggtggaac ggtggatgtc tgcactgtga catcagctga gtaagtaaca acgactgagg    180
atgccgctga cccagggctg gggaagggga ctcccagctc agacaggctt ggctgtggtt    240
tgctttggga ggagagtgaa catcacaggg aatggctcat gtcagcccca ggagggtggg    300
ctggcccctg gtccccgggc tccttctggc cctgcaggcg atagagagcc tcaacctgct    360
gccgcttctc cttggcccgg gtgatggccg tctggaagag cctgcagtag aggtgcacag    420
ccagcggaga gtcgtcattg ccgggtacag ggtaggtgat gaggcagggg ttgcagttgg    480
tgtccacgat gcccactgtg gggatgttca tcttggctgc gtctctcacg gccacgtgtg    540
gctcaaagat gttgttgagc gtgtgcagga agatgatgag gtccggcagg cggaccgtgg    600
ggccaaagag gaggcgcgcg ttggtcagca tgccgcccct gaagtagcga gtgtgggcgt    660
actcgccaca gtcacgggcc atgttctcaa tcaggtacga gaactgccgg ttgcggctta    720
taaacaagat gatgcccttg cggtaggcca tgtgggcggt gaagttcaag gccagctgga    780
ggtgcgtggc tgtctgttcc agtcgatga tgtcgtggtc caggcggctc ccaaagatgt    840
acggctccat aaacctgcca gagaccccac caaggcaagg gggatgagag ttcacggggc    900
catctccact ggctccttgc aggaacacag acgcccacca gggactcccg ggctcctctg    960 tggggggcact atgggctggg aagcacaatt tgcaacgctc ccgtgtgca tggacagcag   1020 tgcagaccca tccaggccac ccctctgcat gcctcgtctc gtggcttaac ccctcctacc   1080
ctctacctct tcccgaagga atcctaatag aactgacccc atatggatgt gtggacatcc   1140
aacatgacgc caaaaggaca ttctgccccg tgcagctcac agggcagccg cctccgtcac   1200
tgtcctcttc ccgaggcttt gcggatgagg ccctctgggg gttggactta gcggggtgct   1260
ctgggccaaa agcattaagg gatcagggca g                                  1291
```

<210> SEQ ID NO 14
<211> LENGTH: 711
<212> TYPE: DNA
<213> ORGANISM: Homo sapiens
<220> FEATURE:
<221> NAME/KEY: misc_feature
<223> OTHER INFORMATION: sequence of STAR14

<400> SEQUENCE: 14

| | | | | | |
|---|---|---|---|---|---|
| ccctggacca | gggtccgtgg | tcttggtggg | cactggcttc | ttcttgctgg | gtgttttcct | 60 |
| gtgggtctct | ggcaaggcac | tttttgtggc | gctgcttgtg | ctgtgtgcgg | gaggggcagg | 120 |
| tgctctttcc | tcttggagct | ggaccctctg | gggcgggtcc | ccgtcggcct | ccttgtgtgt | 180 |
| tttctgcacc | tggtacagct | ggatggcctc | ctcaatgccg | tcgtcgctgc | tggagtcgga | 240 |
| cgcctcgggc | gcctgtacgg | cgctcgtgac | tcgctttccc | ctccttgcgg | tgctggcgtt | 300 |
| ccttttaatc | ccacttttat | tctgtactgc | ttctgaaggg | cggtgggggt | tgctggcttt | 360 |
| gtgctgccct | cctctcctg | cgtggtcgtg | gtcgtgacct | tggacctgag | gcttctgggc | 420 |
| tgcacgtttg | tctttgctaa | ccggggggagg | tctgcagaag | gcgaactcct | tctggacgcc | 480 |
| catcaggccc | tgccggtgca | ccacctttgt | agccggctct | tggtgggatt | tcgagagtga | 540 |
| cttcgccgaa | ttttcatgtg | tgtctggttt | cttctccact | gacccatcac | attttttgggt | 600 |
| ctcatgctgt | cttttctcat | tcagaaactg | ttctatttct | gccctgatgc | tctgctcaaa | 660 |
| ggagtctgct | ctgctcatgc | tgactgggga | ggcagagccc | tggtccttgc | t | 711 |

<210> SEQ ID NO 15
<211> LENGTH: 1876
<212> TYPE: DNA
<213> ORGANISM: Homo sapiens
<220> FEATURE:
<221> NAME/KEY: misc_feature
<223> OTHER INFORMATION: sequence of STAR15

<400> SEQUENCE: 15

| | | | | | |
|---|---|---|---|---|---|
| gagtccaaga | tcaaggtgcc | agcatcttgt | gagggccttc | ttgttacgtc | actccctagc | 60 |
| gaaagggcaa | agagagggtg | agcaagagaa | aggggggctg | aactcgtcct | tgtagaagag | 120 |
| gcccattccc | gagacaatgg | cattcatcca | ttcactccac | cctcatggcc | tcaccacctc | 180 |
| tcatgaggct | ccacctccca | gccctggttt | gttggggatt | aaatttccaa | cacatgcctt | 240 |
| ttgggggaca | tgttaaaatt | atagcacccc | aaatgttaca | ctatcttttg | atgagcggta | 300 |
| gttctgatttt | taagtctagc | tggcctactt | tttcttgcac | gtgggatgct | ttctgcctgt | 360 |
| tccagggcag | gcagctcttc | tctgtccctc | tgctggcccc | acctcatcct | ctgttgtcct | 420 |
| cttccctcct | tctgtgccct | ggggtcctgg | tgggggtgtg | actgtcaact | gcgttgggct | 480 |
| aacttttttc | cctgctggtg | gcccgtaatg | aaagaaagct | tcttgctccc | aagttcctta | 540 |
| aatccaagct | catagacaac | gcggtctcac | agcaggcctg | gggccagcct | cacgtgagcc | 600 |
| ccttccctgg | tgtagtcact | ggcatggggg | aatgggattt | cctgttgccc | tactgtgtgg | 660 |
| ctgaggtggg | ggttgcttcc | tggagccagg | ccttgtggaa | gggcagtgcc | cactgcagtg | 720 |
| gatgctgggc | cctgaatctg | accccagtgt | tcattggctc | tgtgagaccc | agtgagggca | 780 |
| gggagggaag | tggagctggg | gtgagaagta | gaggccctgc | agggcccacg | tgccagccac | 840 |
| caggcctcag | actaggctca | gatgacggag | agctgcacac | ctgcccaacc | caggccctgc | 900 |
| agtgcccaca | tgccagccgc | tggggcccag | acttgctcca | gagggcggag | agctttacac | 960 |
| cggcccaacc | caggccatgg | ctccaaatgc | gtgacagttt | tgctgttgct | tctttagtc | 1020 |

```
attgtcaagt tgatgcttgt tttgcagagg accaaggctt tatgaaccta ttaccctgtg    1080
tgaagagttt caccaggtta tggaaatttc tttaaaacca taccacagtt ttttcattat    1140
tcatgtatat ttttaaaaat aattactgca ctcagtagaa taacatgaaa atgttgcctg    1200
ttagccattt tccagtttgc cccgagaata ctgggggcac ttgtggctgc aatgtttatc    1260
ctgcggcagc tttgccatga agtatctcac ttttattatt attttttgcat tgctcgagta   1320 tattgacttt ggaaacaaaa gacatcattc tatttatagc attatgtttt tagtagtggt    1380
atttccatat acaagataca gtaattttcc gtcaatgaaa atgtcaaatt ctagaaaatg    1440
taacattcct atgcgtggtg ttaacatcgt tctctaacag ttgttggccg aagattcgtt    1500
tgatgaatcc gattttccca aaatagccga ttctgatgat tcagacgatt ctgatgttct    1560
gtttagaaat aattccaaga acagttttta cattttatttt tcacattgaa aatcagtcag   1620
atttgcttca gcctcaaaga gcacgtttat gtaaaattaa atgagtgctg gcagccagct    1680
gcgctttgtt tttctaaatg ggaaaagggt taaatttcac tcagcttttta aatgacagcg   1740 cacagcctgt gtcatagagg gttggaggag atgactttaa ctgcctgtgg ttaggatccc    1800
tttcccccag gaatgtctgg gagcccactg ccgggtttgc tgtccgtctc gtttggactc    1860
agttctgcat gtactg                                                    1876

<210> SEQ ID NO 16
<211> LENGTH: 1282
<212> TYPE: DNA
<213> ORGANISM: Homo sapiens
<220> FEATURE:
<221> NAME/KEY: misc_feature
<223> OTHER INFORMATION: sequence of STAR16

<400> SEQUENCE: 16
cgcccacctc ggcttttccaa agtgctggga ttacaggcat gagtcactgc gcccatcctg    60
attccaagtc tttagataat aacttaactt tttcgaccaa ttgccaatca ggcaatcttt    120
gaatctgcct atgacctagg acatccctct ccctacaagt tgccccgcgt ttccagacca    180
aaccaatgta catcttacat gtattgattg aagttttaca tctccctaaa acatataaaa    240
ccaagctata gtctgaccac ctcaggcacg tgttctcagg acctccctgg ggctatggca    300
tgggtcctgg tcctcagatt tggctcagaa taaatctctt caaatatttt ccagaatttt    360
actcttttca tcaccattac ctatcaccca taagtcagag ttttccacaa ccccttcctc    420
agattcagta atttgctaga atggccacca aactcaggaa agtattttac ttacaattac    480
caatttatta tgaagaactc aaatcaggaa tagccaaatg gaagaggcat agggaaaggt    540
atggaggaag gggcacaaag cttccatgcc ctgtgtgcac accaccctct cagcatcttc    600
atgtgttcac caactcagaa gctcttcaaa ctttgtcatt tagggg tttt tatggcagtt    660 ccactatgta ggcatggttg ataaatcact ggtcatcggt gatagaactc tgtctccagc    720
tcctctctct ctcctcccca gaagtcctga ggtgggctg aaagtttcac aaggttagtt     780
gctctgacaa ccagcccta tcctgaagct attgaggggt cccccaaaag ttaccttagt     840
atggttggaa gaggcttatt atgaataaca aaagatgctc ctattttttac cactagggag   900 catatccaag tcttgcggga acaaagcatg ttactggtag caaattcata caggtagata    960
gcaatctcaa ttcttgcctt ctcagaagaa agaatttgac caaggggggca taaggcagag   1020 tgagggacca agataagttt tagagcagga gtgaaagtta ttaaaaagt tttaggcagg     1080 aatgaaagaa agtaaagtac atttggaaga gggccaagtg ggcgacatga gagagtcaaa   1140
```

<210> SEQ ID NO 17
<211> LENGTH: 793
<212> TYPE: DNA
<213> ORGANISM: Homo sapiens
<220> FEATURE:
<221> NAME/KEY: misc_feature
<223> OTHER INFORMATION: sequence of STAR17

<400> SEQUENCE: 17

```
atccgagggg aggaggagaa gaggaaggcg agcagggcgc cggagcccga ggtgtctgcg      60
agaactgttt taaatggttg gcttgaaaat gtcactagtg ctaagtggct tttcggattg     120
tcttatttat tactttgtca ggtttcctta aggagagggt gtgttggggg tgggggagga     180
ggtggactgg ggaaacctct gcgtttctcc tcctcggctg cacagggtga gtaggaaacg     240
cctcgctgcc acttaacaat ccctctatta gtaaatctac gcggagactc tatgggaagc     300
cgagaaccag tgtcttcttc cagggcagaa gtcacctgtt gggaacggcc cccgggtccc     360
cctgctgggc tttccggctc ttctaggcgg cctgatttct cctcagccct ccacccagcg     420
tccctcaggg acttttcaca cctccccacc cccatttcca ctacagtctc caggggcaca     480
gcacttcatt gacagccaca cgagccttct cgttctcttc tcctctgttc cttctctttc     540
tcttctcctc tgttccttct ctttctctgt cataatttcc ttggtgcttt cgccacctta     600
aacaaaaaag agaaaaaaat aaaataaaaa aaacccattc tgagccaaag tattttaaga     660
tgaatccaag aaagcgaccc acatagcсcсt ccccacccac ggagtgcgcc aagacgcacc     720
caggctccat cacagggccg agagcagcgc cactctggtc gtacttttgg gtcaagagat     780
cttgcaaaag agg                                                        793
```

<210> SEQ ID NO 18
<211> LENGTH: 492
<212> TYPE: DNA
<213> ORGANISM: Homo sapiens
<220> FEATURE:
<221> NAME/KEY: misc_feature
<223> OTHER INFORMATION: sequence of STAR18

<400> SEQUENCE: 18

```
atcttttgc tctctaaatg tattgatggg ttgtgttttt tttcccacct gctaataaat       60
attacattgc aacattcttc cctcaacttc aaaactgctg aactgaaaca atatgcataa     120
aagaaaatcc tttgcagaag aaaaaaagct attttctccc actgattttg aatggcactt     180
gcggatgcag ttcgcaaatc ctattgccta ttccctcatg aacattgtga atgaaacct      240
ttggacagtc tgccgcattg cgcatgagac tgcctgcgca aggcaagggt atggttccca     300
aagcacccag tggtaaatcc taacttatta ttcccttaaa attccaatgt aacaacgtgg     360
gccataaaag agtttctgaa caaaacatgt catctttgtg gaaaggtgtt tttcgtaatt     420
aatgatggaa tcatgctcat ttcaaaatgg aggtccacga tttgtggcca gctgatgcct     480
gcaaattatc ct                                                         492
```

<210> SEQ ID NO 19
<211> LENGTH: 1840
<212> TYPE: DNA

<213> ORGANISM: Homo sapiens
<220> FEATURE:
<221> NAME/KEY: misc_feature
<223> OTHER INFORMATION: sequence of STAR19

<400> SEQUENCE: 19

| | | | | | |
|---|---|---|---|---|---|
| tcacttcctg | atattttaca | ttcaaggcta | gctttatgca | tatgcaacct | gtgcagttgc | 60 |
| acagggcttt | gtgttcagaa | agactagctc | ttggtttaat | actctgttgt | tgccatcttg | 120 |
| agattcatta | taatataatt | tttgaatttg | tgttttgaac | gtgatgtcca | atgggacaat | 180 |
| ggaacattca | cataacagag | gagacaggtc | aggtggcagc | ctcaattcct | tgccacccTT | 240 |
| ttcacataca | gcattggcaa | tgccccatga | gcacaaaatt | tgggggaacc | atgatgctaa | 300 |
| gactcaaagc | acatataaac | atgttacctc | tgtgactaaa | agaagtggag | gtgctgacag | 360 |
| cccccagagg | ccacagttta | tgttcaaacc | aaaacttgct | tagggtgcag | aaagaaggca | 420 |
| atggcagggt | ctaagaaaca | gcccatcata | tccttgttta | ttcatgttac | gtccctgcat | 480 |
| gaactaatca | cttacactga | aaatattgac | agaggaggaa | atggaaagat | agggcaaccc | 540 |
| atagttcttt | ttccttttag | tctttcctta | tcagtaaacc | aaagatagta | ttggtaaaat | 600 |
| gtgtgtgagt | taattaatga | gttagttta | ggcagtgttt | ccactgttgg | ggtaagaaca | 660 |
| aaatatatag | gcttgtattg | agctattaaa | tgtaaattgt | ggaatgtcag | tgattccaag | 720 |
| tatgaattaa | atatccttgt | atttgcattt | aaaattggca | ctgaacaaca | aagattaaca | 780 |
| gtaaaattaa | taatgtaaaa | gtttaatttt | tacttagaat | gacattaaat | agcaaataaa | 840 |
| agcaccatga | taaatcaaga | gagagactgt | ggaaagaagg | aaaacgtttt | tattttagta | 900 |
| tatttaatgg | gactttcttc | ctgatgtttt | gttttgtttt | gagagagagg | gatgtggggg | 960 |
| cagggaggtc | tcattttgtt | gcccaggctg | gacttgaact | cctgggctcc | agctatcctg | 1020 |
| ccttagcttc | ttgagtagct | gggactacag | gcacacacca | cagtgtctga | cattttctgg | 1080 |
| attttttttt | tttttttatt | tttttgtga | gacaggttct | ggctctgtta | ctcaggttgc | 1140 |
| agtgcagtgg | catgatagcg | gctcactgca | gcctcaacct | cctcagctta | agctactctc | 1200 |
| ccacttcagc | ctcctgagta | gcaggacta | cagttgtgtg | ccaccacacc | tgtggctaat | 1260 |
| ttttgtagag | atggggtctc | tccacgttgc | cgaggctggt | ctccaactcc | tggtctcaag | 1320 |
| cgaacctcct | gacttggcct | cccgaagtgc | tgggattaca | ggcttgagcc | actgcatcca | 1380 |
| gcctgtcctc | tgtgttaaac | ctactccaat | ttgtctttca | tctctacata | aacgctctt | 1440 |
| ttcaaagttc | ccatagacct | cactgttgct | aatctaataa | taaattatct | gccttttctt | 1500 |
| acatggttca | tcagtagcag | cattagattg | ggctgctcaa | ttcttcttgg | tatattttct | 1560 |
| tcatttggct | tctggggcat | cacactctct | ttgagttact | cattcctcat | tgatagcttc | 1620 |
| ttcctagtct | tctttactgg | ttcttcctct | tctccctgac | tccttaatat | tgttttctc | 1680 |
| cccaggcttt | agttcttagt | cctcttctgt | tatctattta | cacccaattc | tttcagagtc | 1740 |
| tcatccagag | tcatgaactt | aaacctgttt | ctgtgcagat | aattcacatt | attatatctc | 1800 |
| cagcccagac | tctcccgcaa | actgcagact | gatcctactg | | | 1840 |

<210> SEQ ID NO 20
<211> LENGTH: 780
<212> TYPE: DNA
<213> ORGANISM: Homo sapiens
<220> FEATURE:
<221> NAME/KEY: misc_feature
<223> OTHER INFORMATION: sequence of STAR20

<400> SEQUENCE: 20

```
gatctcaagt tcaatatca tgttttggca aaacattcga tgctcccaca tccttaccta    60
aagctaccag aaaggctttg ggaactgtca acagagctac agaaaagtca gtaaagacca   120
atggacccct caaacaaaaa cagccaagct tttctgccaa aagatgact gagaagactg    180 ttaaagcaaa aaactctgtt cctgcctcag atgatggcta tccagaaata gaaaaattat   240
ttcccttcaa tcctctaggc ttcgagagtt ttgacctgcc tgaagagcac cagattgcac   300 atctccccctt gagtgaagtg cctctcatga tacttgatga ggagagagag cttgaaaagc   360
tgtttcagct gggccccccct tcacctttga agatgccctc tccaccatgg aaatccaatc   420
tgttgcagtc tcctttaagc attctgttga ccctggatgt tgaattgcca cctgtttgct   480
ctgacataga tatttaaatt tcttagtgct ttagagtttg tgtatatttc tattaataaa   540
gcattatttg tttaacagaa aaaagatat atacttaaat cctaaaataa aataaccatt    600
aaaaggaaaa acaggagtta aactaataa gggaacaaag gacataaaat gggataataa    660
tgcttaatcc aaaataaagc agaaaatgaa gaaaaatgaa atgaagaaca gataaataga   720
aaacaaatag caatatgaaa gacaaacttg accgggtgtg gtggctgatg cctgtaatcc   780
```

<210> SEQ ID NO 21
<211> LENGTH: 607
<212> TYPE: DNA
<213> ORGANISM: Homo sapiens
<220> FEATURE:
<221> NAME/KEY: misc_feature
<223> OTHER INFORMATION: sequence of STAR21

<400> SEQUENCE: 21

```
gatcaataat ttgtaatagt cagtgaatac aaaggggtat atactaaatg ctacagaaat    60
tccattcctg ggtataaatc ctagacatat ttatgcatat gtacaccaag atatatctgc   120
aagaatgttc acagcaaatc tctttgtagt agcaaaaggc caaaaggtct atcaacaaga   180
aaattaatac attgtggcac ataatggcat ccttatgcca ataaaaatgg atgaaattat   240
agttaggttc aaaaggcaag cctccagata atttatatca tataattcca tgtacaacat   300
tcaacaacaa gcaaaactaa acatatacaa atgtcaggga aaatgatgaa caaggttaga   360
aaatgattaa tataaaaata ctgcacagtg ataacattta atgagaaaaa aagaaggaag   420
ggcttaggga gggacctaca gggaactcca aagttcatgg taagtactaa atacataatc   480
aaagcactca aaatagaaaa tattttagta atgttttagc tagttaatat cttacttaaa   540
acaaggtcta ggccaggcac ggtggctcac acctgtaatc ccagcacttt gggaggctga   600
ggcgggt                                                             607
```

<210> SEQ ID NO 22
<211> LENGTH: 1380
<212> TYPE: DNA
<213> ORGANISM: Homo sapiens
<220> FEATURE:
<221> NAME/KEY: misc_feature
<223> OTHER INFORMATION: sequence of STAR22

<400> SEQUENCE: 22

```
cccttgtgat ccacccgcct tggcctccca aagtgctggg attacaggcg tgagtcacta    60
cgcccggcca ccctccctgt atattatttc taagtatact attatgttaa aaaaagttta   120 aaatattga tttaatgaat tcccagaaac taggatttta catgtcacgt tttcttatta    180 taaaataaa atcaacaat aaatatatgg taaaagtaaa aagaaaaaca aaaacaaaaa    240
```

```
gtgaaaaaaa taaacaacac tcctgtcaaa aacaacagt  tgtgataaaa cttaagtgcc      300
tgaaaattta gaaacatcct tctaaagaag ttctgaataa aataaggaat aaaataatca      360
catagttttg gtcattggtt ctgtttatgt gatggattat gtttattgat ttgtgtatgt      420
tgaacttatc tcaatagatg cagacaaggc cttgataaaa gttttttaaca cctttttcatg    480 ttgaaaactc tcaatagact aggtattgat gaaacatatc tcaaaataat agaagctatt      540
tatgataaac ccatagccaa tatcatactg agtgggcaaa agctggaagc attccctttg      600
aaaactggca caagacaagg atgccctctc tcaccactcc tattaaatgt agtattggaa      660
gttctggcca gagcaatcag gcaggagaaa gaaaaggtat taaaatagga agagaggaag     720
tcaaattgtc tctgtttgca gtaaacatga ttgtatattt agaaaacccc attgtctcat      780
cctaaaaact ccttaagctg ataaacaact tcagcaaagt ctcaggatac aaaatcaatg      840
tgcaaaaatc acaagcattc ctatacaccg ataatagaca gcagagagcc aaatcatgag      900
tgaagtccca ttcacaattg cttcaaagaa aataaaatac ttaggaatac aactttcacg     960
ggacatgaag gacattttca aggacaacta aaaaccactg ctcaaggaaa tgagagagga     1020
cacaagaaaa tggaaaaaca ttccatgctc atggaagaat caatatcatg aaaatggcca     1080
tactgcccaa agtaatttat agattcaatg ctaaccccat caagccacca ttgacttttct    1140 tcacagaact agaaaaaaac tattttaaaa ctcatatgta gtcaaaaaga gtcggtatag     1200
ccaagacaat cctaagcata aagaacaaag ctggatgcat cacgctgact tcaaaccata     1260
ctacaaggct acagtaacca aaacagcatg gtactggtac caaaacagat agatagaccg     1320
atagaacaga acagaggcct cggaaataac accacacatc tacaaccctt tgatcttcaa     1380
```

<210> SEQ ID NO 23
<211> LENGTH: 1246
<212> TYPE: DNA
<213> ORGANISM: Homo sapiens
<220> FEATURE:
<221> NAME/KEY: misc_feature
<223> OTHER INFORMATION: sequence of STAR23

<400> SEQUENCE: 23

```
atcccctcat ccttcagggc agctgagcag ggcctcgagc agctggggga gcctcactta       60
atgctcctgg gagggcagcc agggagcatg gggtctgcag gcatggtcca gggtcctgca     120
ggcggcacgc accatgtgca gccgccccca cctgttgctc tgcctccgcc acctggccat     180
gggcttcagc agccagccac aaagtctgca gctgctgtac atggacaaga agcccacaag     240
cagctagagg accttgtgtt ccacgtgccc agggagcatg gcccacagcc aaagaccag      300 tcaggagcag gcaggggctt ctggcaggcc cagctctacc tctgtcttca cacagatggg     360
agatttctgt tgtgattttg agtgatgtgc ccctttggtg acatccaaga tagttgctga     420
agcaccgctc taacaatgtg tgtgtattct gaaaacgaga acttctttat tctgaaataa     480
ttgatgcaaa ataaattagt ttggatttga aattctattc atgtaggcat gcacacaaaa     540
gtccaacatt gcatatgaca caaagaaaag aaaaagcttg cattccttaa atacaaatat     600
ctgttaacta tatttgcaaa tatatttgaa tacacttcta ttatgttaca tataatatta     660
tatgtatatg tatatataat atacatatat atgttacata taatatactt ctattatgtt    720
acatataata tttatctata agtaaataca taaatataaa gatttgagta gctgtagaac     780
attgtcttat gtgttatcag ctactactac aaaaatatct cttccactta tgccagtttg     840
ccatataaat atgatcttct cattgatggc ccagggcaag agtgcagtgg gtacttattc     900
```

-continued

| | |
|---|---|
| tctgtgagga gggaggagaa aagggaacaa ggagaaagtc acaaagggaa aactctggtg | 960 |
| ttgccaaaat gtcaagtttc acatattccg agacggaaaa tgacatgtcc cacagaagga | 1020 |
| ccctgcccag ctaatgtgtc acagatatct caggaagctt aaatgatttt tttaaaagaa | 1080 |
| aagagatggc attgtcactt gtttcttgta gctgaggctg tgggatgatg cagatttctg | 1140 |
| gaaggcaaag agctcctgct ttttccacac cgagggactt tcaggaatga ggccagggtg | 1200 |
| ctgagcacta caccaggaaa tccctggaga gtgttttttct tactta | 1246 |

```
<210> SEQ ID NO 24
<211> LENGTH: 939
<212> TYPE: DNA
<213> ORGANISM: Homo sapiens
<220> FEATURE:
<221> NAME/KEY: misc_feature
<223> OTHER INFORMATION: sequence of STAR24

<400> SEQUENCE: 24
```

| | |
|---|---|
| acgaggtcac gagttcgaga ccagcctggc caagatggtg aagccctgtc tctactaaaa | 60 |
| atacaacaag tagccgggcg cggtgacggg cgcctgtaat cccagctact caggaggctg | 120 |
| aagcaggaga atctctagaa cccaggaggc ggaggtgcag tgagctgaga ctgccccgct | 180 |
| gcactctagc ctgggcaaca cagcaagact ctgtctcaaa taaataaata aataaataaa | 240 |
| taaataaata aataaataaa tagaaaggga gagttggaag tagatgaaag agaagaaaag | 300 |
| aaatcctaga tttcctatct gaaggcacca tgaagatgaa ggccacctct tctgggccag | 360 |
| gtcctcccgt tgcaggtgaa ccgagttctg gcctccattg gagaccaaag gagatgactt | 420 |
| tggcctggct cctagtgagg aagccatgcc tagtcctgtt ctgtttgggc ttgatcctgt | 480 |
| atcacttgat tgtctctcct ggactttcca tggattccag ggatgcaact gagaagttta | 540 |
| tttttaatgc acttacttga agtaagagtt attttaaaac attttagcaa aggaaatgaa | 600 |
| ttctgacagg ttttgcactg aagacattca catgtgagga aaacaggaaa accactatgc | 660 |
| tagaaaaagc aaatgctgtt gagattgtct cacaaacaca aattgcgtgc cagcaggtag | 720 |
| gtttgagcct caggttgggc acattttacc ttaagcgcac tgttggtgga acttaaggtg | 780 |
| actgtaggac ttatatatac atacatacat ataatatata tacatattta tgtgtatata | 840 |
| cacacacaca cacacacaca cacacagggt cttgctatct tgcccagggt ggtctccaac | 900 |
| tctgggtctc aagcgatcct ctgcctcccc ttcccaaag | 939 |

```
<210> SEQ ID NO 25
<211> LENGTH: 1067
<212> TYPE: DNA
<213> ORGANISM: Homo sapiens
<220> FEATURE:
<221> NAME/KEY: misc_feature
<223> OTHER INFORMATION: sequence of STAR25

<400> SEQUENCE: 25
```

| | |
|---|---|
| cagcccctct tgtgttttc tttatttctc gtacacacac gcagttttaa gggtgatgtg | 60 |
| tgtataatta aaaggaccct tggcccatac tttcctaatt ctttagggac tgggattggg | 120 |
| tttgactgaa atatgttttg gtggggatgg gacggtggac ttccattctc cctaaactgg | 180 |
| agttttggtc ggtaatcaaa actaaaagaa acctctggga gactggaaac ctgattggag | 240 |
| cactgaggaa caagggaatg aaaaggcaga ctctctgaac gtttgatgaa atggactctt | 300 |
| gtgaaaatta acagtgaata ttcactgttg cactgtacga agtctctgaa atgtaattaa | 360 |
| aagttttat tgagcccccg agctttggct tgcgcgtatt tttccggtcg cggacatccc | 420 |

```
accgcgcaga gcctcgcctc cccgctgccc tcagcctccg atgacttccc cgccccgcc      480 ctgctcggtg acagacgttc tactgcttcc aatcggaggc acccttcgcg ggagcggcca     540
atcgggagct ccggcaggcg gggaggccgg gccagttaga tttggaggtt caacttcaac    600
atggccgaag caagtagcgc caatctaggc agcggctgtg aggaaaaaag gcatgagggg    660
tcgtcttcgg aatctgtgcc acccggcact accatttcga gggtgaagct cctcgacacc    720
atggtggaca ctttcttca gaagctggtc gccgccggca ggtaaagtgg acgcagccgc     780
ggtgggagtg tttgttggca ccgaagctca aatcccgcga ggtcaggacg gccgcaggct    840
ggcgcgcggt gacgtgggtc cgcgttgggg cggggcagt cggacgaggc gacccagtca     900
aatcctgagc cttaggagtc agggtattca cgcactgata acctgtagcg gaccgggata    960
gctagctact ccttcctaca ggaagcccccg ttttcactaa aatttcaggt ggttgggagg  1020
aaagatagag cctttgcaaa ttagagcagg gtttttttatt ttttttat              1067
```

<210> SEQ ID NO 26
<211> LENGTH: 540
<212> TYPE: DNA
<213> ORGANISM: Homo sapiens
<220> FEATURE:
<221> NAME/KEY: misc_feature
<223> OTHER INFORMATION: sequence of STAR26

<400> SEQUENCE: 26

```
cccctgaca agccccagtg tgtgatgttc cccactctgt gtccatgcat tctcattgtt      60
caactcccat ctgtgagtga aacatgcag tgtttggttt tctgtccttg agatagtttg     120
ctgagaatga tggtttccag cttcatccat gtccttgcaa aggaagtgaa cttatccttt    180
tttatggctt catagtattc catggcacat atgtgccaca ttttttttaat ccagtctatc   240 attgatggac atttggggttg gttccaagtc tttgctattg tgaatagcac cacaattaac    300
atatgtgtgc atgtatacat ctttatagta gcatgattta taatccttcg ggtatatacc    360
ctgtaatggg atcgctgggt caaatggtat ttctagttct agatccttga ggaatcacca    420
cactgctttc cacaatggtt gaactaattt acgctcccac cagcagtgta aaagcattcc    480
tatttctcca cgtcctctcc agtatctgtt gtttcctgac tttttaatga tcatcattct    540
```

<210> SEQ ID NO 27
<211> LENGTH: 1520
<212> TYPE: DNA
<213> ORGANISM: Homo sapiens
<220> FEATURE:
<221> NAME/KEY: misc_feature
<223> OTHER INFORMATION: sequence of STAR27

<400> SEQUENCE: 27

```
cttggccctc acaaagcctg tggccaggga acaattagcg agctgcttat tttgctttgt      60
atccccaatg ctgggcataa tgcctgccat tatgagtaat gccggtagaa gtatgtgttc     120
aaggaccaaa gttgataaat accaaagaat ccagagaagg gagagaacat tgagtagagg    180
atagtgacag aagagatggg aacttctgac aagagttgtg aagatgtact aggcaggggg    240
aacagcttaa ggagagtcac acaggaccga gctcttgtca agccggctgc catggaggct    300
gggtggggcc atggtagctt tcccttcctt ctcaggttca gagtgtcagc cttgaacttc    360
taattcccag aggcatttat tcaatgtttt cttctagggg catacctgcc ctgctgtgga    420
agactttctt ccctgtgggt cgccccagtc cccagatgag acggtttggg tcagggccag    480
```

| | |
|---|---|
| gtgcaccgtt gggtgtgtgc ttatgtctga tgacagttag ttactcagtc attagtcatt | 540 |
| gagggaggtg tggtaaagat ggagatgctg ggtcacatcc ctagagaggt gttccagtat | 600 |
| gggcacatgg gagggctgga aggataggtt actgctagac gtagagaagc cacatccttt | 660 |
| aacaccctgg cttttcccac tgccaagatc cagaaagtcc ttgtggtttc gctgctttct | 720 |
| cctttttttt tttttttttt tttctgagat ggagtctggc tctgtcgccc aggctggagt | 780 |
| gcagtggcac gatttcggct cactgcaagt tccgcctcct aggttcatac cattctccca | 840 |
| cctcagcctc ccgagtagct gggactacag gcgccaccac acccagctaa ttttttgtat | 900 |
| ttttagtaga cggcgtttc accatgtta gccaggatgg tcttgatccg cctgcctcag | 960 |
| cctcccaaag tgctgggatt acaggcgtga gccaccgcgc ccggcctgct tcttctttc | 1020 |
| atgaagcatt cagctggtga aaaagctcag ccaggctggt ctggaactct tgacctcaag | 1080 |
| tgatctgcct gcctcagcct cccaaagtgc tgagattaca ggcatgagcc agtccgaatg | 1140 |
| tggctttttt tgttttgttt tgaaacaagg tctcactgtt gcccaggctg cagtgcagtg | 1200 |
| gcatacctca gctccactgc agcctcgacc tcctgggctc aagcaatcct cccaactgag | 1260 |
| cctccccagt agctggggct acaagcgcat gccaccacgc ctggctattt tttttttttt | 1320 |
| tttttttttt gagaaggagt ttcattcttg ttgcccaggc tggagtgcaa tggcacagtc | 1380 |
| tcagctcact gcagcctccg cctcctgggt tcaagcgatt ctcctgcctc agcctcccga | 1440 |
| gtagctggga ttataggcac ctgccaccat gcctggctaa ttttttgta tttttagtag | 1500 |
| ggatggggtt tcaccatgtt | 1520 |

<210> SEQ ID NO 28
<211> LENGTH: 961
<212> TYPE: DNA
<213> ORGANISM: Homo sapiens
<220> FEATURE:
<221> NAME/KEY: misc_feature
<223> OTHER INFORMATION: sequence of STAR28

<400> SEQUENCE: 28

| | |
|---|---|
| aggaggttat tcctgagcaa atggccagcc tagtgaactg gataaatgcc catgtaagat | 60 |
| ctgtttaccc tgagaagggc atttcctaac tctcccctata aaatgccaag tggagcaccc | 120 |
| cagatgaaat agctgatatg cttttctatac aagccatcta ggactggctt tatcatgacc | 180 |
| aggatattca cccactgaat atggctatta cccaagttat ggtaaatgct gtagttaagg | 240 |
| gggtcccttc cacatggaca ccccaggtta taaccagaaa gggttcccaa tctagactcc | 300 |
| aagagagggt tcttagacct catgcaagaa agaacttggg gcaagtacat aaagtgaaag | 360 |
| caagtttatt aagaaagtaa agaaacaaaa aaatggctac tccataagca aagttatttc | 420 |
| tcacttatat gattaataag agatggatta ttcatgagtt ttctgggaaa ggggtgggca | 480 |
| attcctggaa ctgagggttc ctcccacttt tagaccatat agggtatctt cctgatattg | 540 |
| ccatggcatt tgtaaactgt catggcactg atggagtgt cttttagcat tctaatgcat | 600 |
| tataattagc atataatgag cagtgaggat gaccagaggt cacttctgtt gccatattgg | 660 |
| tttcagtggg gtttggttgg ctttttttt tttttaacca caacctgttt ttatttatt | 720 |
| tatttattta tttatttatt tatatttttt atttttttt agatggagtc ttgctctgtc | 780 |
| acccaggtta gagtgcagtg gcaccatctc ggctcactgc aagctctgcc tccttggttc | 840 |
| acgccattct gctgcctcag cctcccgagt agctgggact acaggtgcct gccaccatac | 900 |
| ccggctaatt ttttctattt ttcagtagag acggggtttc accgtgttag ccaggatggt | 960 | c                                                                                961

<210> SEQ ID NO 29
<211> LENGTH: 2233
<212> TYPE: DNA
<213> ORGANISM: Homo sapiens
<220> FEATURE:
<221> NAME/KEY: misc_feature
<223> OTHER INFORMATION: sequence of STAR29

<400> SEQUENCE: 29

```
agcttggaca cttgctgatg ccactttgga tgttgaaggg ccgccctctc ccacaccgct      60
ggccactttt aaatatgtcc cctctgccca aagggcccc agaggagggg ctggtgaggg     120
tgacaggagt tgactgctct cacagcaggg ggttccggag ggacctttc tccccattgg     180
gcagcataga aggacctaga agggcccct ccaagcccag ctgggcgtgc agggccagcg     240
attcgatgcc ttcccctgac tcaggtggcg ctgtcctaaa ggtgtgtgtg ttttctgttc     300
gccaggggt ggcggataca gtggagcatc gtgcccgaaa tgtctgagcc cgtggtaagt     360
ccctggaggg tgcacggtct cctccgactg tctccatcac gtcaggcctc acagcctgta     420
ggcaccgctc ggggaagcct ctggatgagg ccatgtggtc atccccctgg agtcctggcc     480
tggcctgaag aggaggggag gaggaggcca gcccctccct agcccaagg cctgcgaggc     540
tgcaagcccg gccccacatt ctagtccagg cttggctgtg caagaagcag attgcctggc     600
cctggccagg cttcccagct aggatgtggt atggcagggg tggggacat tgagggggctg     660
ctgtagcccc cacaacctcc ccaggtaggg tggtgaacag taggctggac aagtggacct     720
gttcccatct gagattcaag agcccacctc tcggaggttg cagtgagccg agatccctcc     780
actgcactcc agcctgggca acagagcaag actctgtctc aaaaaaacag aacaacgaca     840
acaaaaaacc cacctctggc ccactgccta actttgtaaa taaagttttta ttggcacata     900
gacacaccca ttcatttaca tactgctgcg gctgcttttg cattacccct gagtagacga     960
cagaccacgt ggccatggaa gccaaaaata tttactgtct ggcccttta c agaagtctgc    1020
tctagaggga gaccccggcc catggggcag gaccactggg cgtgggcaga agggaggcct    1080
cggtgcctcc acgggcctag ttgggtatct cagtgcctgt ttcttgcatg gagcaccagg    1140
ggtcagggca agtacctgga ggaggcaggc tgttgcccgc ccagcactgg gacccaggag    1200
accttgagag gctcttaacg aatggagac aagcaggacc agggctccca ttggctgggc    1260
ctcagttttcc ctgcctgtaa gtgagggagg gcagctgtga aggtgaactg tgaggcagag    1320
cctctgctca gccattgcag gggcggctct gccccactcc tgttgtgcac ccagagtgag    1380
gggcacgggg tgagatgtca ccatcagccc atagggtgt cctcctggtg ccaggtcccc    1440
aagggatgtc ccatccccc tggctgtgtg gggacagcag agtccctggg gctgggaggg    1500
ctccacactg ttttgtcagt ggttttctg aactgttaaa tttcagtgga aaattctctt    1560
tccccttta ctgaaggaac ctccaaagga agacctgact gtgtctgaga agttccagct    1620
ggtgctggac gtcgcccaga aagcccaggt actgccacgg gcgccggcca ggggtgtgtc    1680
tgcgccagcc atgggcacca gccaggggtg tgtctacgcc ggccaggggt aggtctccgc    1740
cggcctccgc tgctgcctgg ggagggccgt gcctgacact gcaggcccgg tttgtccgcg    1800
gtcagctgac ttgtagtcac cctgcccttg gatggtcgtt acagcaactc tggtggttgg    1860
ggaaggggcc tcctgattca gcctctgcgg acggtgcgcg agggtggagc tccctcccct    1920
ccccaccgcc cctggccagg gttgaacgcc cctgggaagg actcaggccc gggtctgctg    1980
```

-continued

| | |
|---|---|
| ttgctgtgag cgtggccacc tctgccctag accagagctg ggccttcccc ggcctaggag | 2040 |
| cagccgggca ggaccacagg gctccgagtg acctcagggc tgcccgacct ggaggccctc | 2100 |
| ctggcgtcgc ggtgtgactg acagcccagg agcgggggct gttgtaattg ctgtttctcc | 2160 |
| ttcacacaga acctttccgg gaagatggct gacatcctgg agaagatcaa gaagtaagtc | 2220 |
| ccgcccccca ccc | 2233 |

<210> SEQ ID NO 30
<211> LENGTH: 1851
<212> TYPE: DNA
<213> ORGANISM: Homo sapiens
<220> FEATURE:
<221> NAME/KEY: misc_feature
<223> OTHER INFORMATION: sequence of STAR30

<400> SEQUENCE: 30

| | |
|---|---|
| gggtgcattt ccacccaggg gacacttggc aatggtggga gacattgctt gttgtcacaa | 60 |
| ctgggcatgg gagtgctgct gcgtctagtg ggtagaggcc agagatgctc ctaatatcct | 120 |
| acaaggcaca gaacagcccc ccacaacaga gaattatcca gcctgaaaat gtccacagtg | 180 |
| ctgaggttgg gaaaccctat tctagagcca acaggctgtg aagcttgact catggttcca | 240 |
| tcaccaatag ctgcgtgacc ttggtgagtt ccttagctgc tctgtgcctc ggattcatgg | 300 |
| taggttttcc ttgttaggtt taaatgagtg aagttataca gagggcctga agtctcatgg | 360 |
| tattttacta gagcctcatt gtgttttagt tataattaga aattgggtaa ggtaaggaca | 420 |
| cagaagaagc catctgatct gggggcttca cacttagaag tgacctcgga gcaattgtat | 480 |
| tggggtggaa agggactaac agccaggagc agagggcaca ttggaattgg ggccagaggg | 540 |
| cacagactgc cttgtccatc aggcatagca atggacagag gaaggggaat gactagttat | 600 |
| ggctgcaagg ccaagtacag gggacttatt tctcatatct atctatctat ctacctaccg | 660 |
| tctatttatc tatcatctat ctacttattt atctatctat ttatgcatgt gtaccaaccg | 720 |
| aaagttttag taaatgcaca aactgcgata taatgaaaat ggaaattttc aaaagaagag | 780 |
| aaatcacctg ccacctgact acctaacaa atgagtggtt ttcatctctc cttccaggcc | 840 |
| tgtcattttt acagtgcttt agtcataaaa caggtcctct attctattgt tttatgtcac | 900 |
| atgaaattgt accataagca ttttccatga tgtgactcca ctgtttcatt ttccattttt | 960 |
| ttccagaatg aagataacct cattgttttt ttcctgattg taaaaatgct ctgtgctctt | 1020 |
| tttttttttt tttaacaatg caggcagtac caaaaagtat gaagaagaat gtaatagttc | 1080 |
| ccatttccca tctcactctt taaggccagc attttggtga acatccatcc gaacaaatct | 1140 |
| ccacgcgttt atcaatttgt tgacttactc cttcttttat gtaaatatga acatgattta | 1200 |
| actgccagtc catttggaac cttaaagtga aggttttta ttgttggggt ttgctatggt | 1260 |
| ctgaatatgt gtgtcccccc aaaatttatg ttgaatccta acgcccaatg cgattaggag | 1320 |
| gtggggccat taggaggtga ttaagtcatg aagtcatcag ccctaatgaa tgggatttgt | 1380 |
| ggccttgaaa agggaccccca gagagctgcc ttgccccttc tgccatgtaa ggacacagtg | 1440 |
| aggagctagg aagggggcct cagcagagac caaatgtgat ggtgcctcga tattggactt | 1500 |
| cccagcctcc agaatgtgag aaatgaattt ctgttgttta taagtcaccc agtctatagt | 1560 |
| attttgttct agcagcccaa acagactaag tcagggttgt tgttttagga agtggggaat | 1620 |
| ggggccatgc atgggtgtac gccagaacaa aggaagccag caagtcctga agatactgg | 1680 |
| aaaagggaat agtgggcacg tgcagtgtgt tagtttcctg aggctgctat aacaaagcac | 1740 |

-continued

| | |
|---|---|
| cacaggttgg gtggcttaaa taacagaaat tcattctccc atcattctgg ggaccagacg | 1800 |
| tctgaaatca agactcctat gccatgctcc ttctgaaggc tccaggggag g | 1851 |

<210> SEQ ID NO 31
<211> LENGTH: 1701
<212> TYPE: DNA
<213> ORGANISM: Homo sapiens
<220> FEATURE:
<221> NAME/KEY: misc_feature
<223> OTHER INFORMATION: sequence of STAR31
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (1667)..(1667)
<223> OTHER INFORMATION: n is a, c, g, or t
<220> FEATURE:
<221> NAME/KEY: misc_feature
<222> LOCATION: (1677)..(1677)
<223> OTHER INFORMATION: n is a, c, g, or t
<220> FEATURE:
<221> NAME/KEY: misc_feature
<222> LOCATION: (1683)..(1684)
<223> OTHER INFORMATION: n is a, c, g, or t
<220> FEATURE:
<221> NAME/KEY: misc_feature
<222> LOCATION: (1686)..(1687)
<223> OTHER INFORMATION: n is a, c, g, or t
<220> FEATURE:
<221> NAME/KEY: misc_feature
<222> LOCATION: (1690)..(1690)
<223> OTHER INFORMATION: n is a, c, g, or t
<220> FEATURE:
<221> NAME/KEY: misc_feature
<222> LOCATION: (1693)..(1696)
<223> OTHER INFORMATION: n is a, c, g, or t

<400> SEQUENCE: 31

| | |
|---|---|
| cacccgcctt ggccccccag agtgctggga ttacaagtgt aaaccaccat tcctggctag | 60 |
| atttaatttt ttaaaaaata aagagaagta ggaatagttc attttaggga gagcccctta | 120 |
| actgggacag gggcaggaca ggggtgaggc ttcccttant tcaagctcac ctcaaaccca | 180 |
| cccaggactg tgtgtcacat tctccaataa aggaaaggtt gctgccccg cctgtgagtg | 240 |
| ctgcagtgga gggtagaggg ccgtgggcag agtgcttcat ggactgctca tcaagaaagg | 300 |
| cttcatgaca atcggcccag ctgctgtcat cccacattct acttccagct aggagaaggc | 360 |
| ggcttgccca cagtcaccca gccggcaagt gtcacccctg ggttggaccc agagctatga | 420 |
| tcctgcccag gggtccagct gagaatcagg cccacgttct aggcagaggg gctcacctac | 480 |
| tgggactcca gtagctgtag tgcatggagg catcatggct gcagcagcct ggacctggtc | 540 |
| tcacactggc tgtccctgtg ggcaggccat cctcaatgcc aggtcaggcc caagcatgta | 600 |
| tcccagacaa tgacaatggg gtggaatcct ctcttgtccc agaagccact cctcactgtt | 660 |
| ctacctgagg aaggcagggg catggtggaa tcctgaagcc tgctgtgagg gtctccagcg | 720 |
| aacttgcaca tggtcagccc tgccttctcc tccctgaact agattgagcg agagcaagaa | 780 |
| ggacattgaa ccagcaccca aagaattttg gggaacggcc tctcatccag gtcaggctca | 840 |
| cctcctttt aaaatttaat taattaatta attaattttt ttttagagac agagtcttac | 900 |
| tgtgtggccc aggctgtagt gcagtggcac aatcatagtt cactgcagcc tcaaactccc | 960 |
| cacctcagcc tctggattag ctgagactac aggtgcacca ccaccacacc cagctaatat | 1020 |
| ttttattttt gtagagagag ggtttcacca tcttgcccag gctggtctca aactcctggg | 1080 |

| | |
|---|---|
| ctcaagtgat cccgcccagg tctgaaagcc cccaggctgg cctcagactg tggggttttc | 1140 |
| catgcagcca cccgagggcg cccccaagcc agttcatctc ggagtccagg cctggccctg | 1200 |
| ggagacagag tgaaaccagt ggttttatg aacttaactt agagtttaaa agatttctac | 1260 |
| tcgatcactt gtcaagatgc gccctctctg gggagaaggg aacgtgactg gattccctca | 1320 |
| ctgttgtatc ttgaataaac gctgctgctt catcctgtgg gggccgtggc cctgtccctg | 1380 |
| tgtgggtggg gcctcttcca tttccctgac ttagaaacca cagtccacct agaacagggt | 1440 |
| ttgagaggct tagtcagcac tgggtagcgt tttgactcca ttctcggctt tcttcttttt | 1500 |
| cttttccagga tttttgtgca gaaatggttc ttttgttgcc gtgttagtcc tccttggaag | 1560 |
| gcagctcaga aggcccgtga atgtcgggg acaggaccc cagggaggg aaccccaggc | 1620 |
| tacgcacttt agggttcgtt ctccagggag ggcgacctga ccccgnatc cgtcggngcg | 1680 |
| cgnngnnacn aannnnttcc c | 1701 |

<210> SEQ ID NO 32
<211> LENGTH: 771
<212> TYPE: DNA
<213> ORGANISM: Homo sapiens
<220> FEATURE:
<221> NAME/KEY: misc_feature
<223> OTHER INFORMATION: sequence of STAR32

<400> SEQUENCE: 32

| | |
|---|---|
| gatcacacag cttgtatgtg ggagctagga ttggaacccc agaagtctgg ccccaggttc | 60 |
| atgctctcac ccactgcata caatggcctc tcataaatca atccagtata aacattaga | 120 |
| atctgcttta aaaccataga attagtagcg taagtaataa atgcagagac catgcagtga | 180 |
| atggcattcc tggaaaaagc ccccagaagg aattttaaat cagctttcgt ctaatcttga | 240 |
| gcagctagtt agcaaatatg agaatacagt tgttcccaga taatgcttta tgtctgacca | 300 |
| tcttaaactg gcgctgtttt tcaaaaactt aaaaacaaaa tccatgactc ttttaattat | 360 |
| aaaagtgata catgtctact tgggaggctg aggtggtggg aggatggctt gagtttgagg | 420 |
| ctgcagtatg ctactatcat gcctataaat agccgctgca ttccagcttg gcaacatac | 480 |
| ccaggcccta tctcaaaaaa ataaaaagta atacatctac attgaagaaa attaatttta | 540 |
| ttgggttttt ttgcattttt attatacaca gcacacacag cacatatgaa aaaatgggta | 600 |
| tgaactcagg cattcaactg gaagaacagt actaaatcaa tgtccatgta gtcagcgtga | 660 |
| ctgaggttgg tttgtttttt ctttttttctt ctcttctctt ctcttttctt tttttttgag | 720 |
| acggagcttt gctcttttg cccaggcttg attgcaatgg cgtgatctca g | 771 |

<210> SEQ ID NO 33
<211> LENGTH: 1368
<212> TYPE: DNA
<213> ORGANISM: Homo sapiens
<220> FEATURE:
<221> NAME/KEY: misc_feature
<223> OTHER INFORMATION: sequence of STAR33

<400> SEQUENCE: 33

| | |
|---|---|
| gcttttatcc tccattcaca gctagcctgg cccccagagt acccaattct ccctaaaaaa | 60 |
| cggtcatgct gtatagatgt gtgtggcttg gtagtgctaa agtggccaca tacagagctc | 120 |
| tgacaccaaa cctcaggacc atgttcatgc cttctcactg agttctggct tgttcgtgac | 180 |
| acattatgac attatgatta tgatgacttg tgagagcctc agtcttctat agcactttta | 240 |
| gaatgcttta taaaaaccat ggggatgtca ttatattcta acctgttagc acttctgttc | 300 |

```
gtattaccca tcacatccca acatcaattc tcatatatgc aggtacctct tgtcacgcgc    360
gtccatgtaa ggagaccaca aaacaggctt tgtttgagca acaaggtttt tatttcacct    420
gggtgcaggt gggctgagtc tgaaaagaga gtcagtgaag ggagacaggg gtgggtccac    480
tttataagat ttgggtaggt agtggaaaat tacaatcaaa gggggttgtt ctctggctgg    540
ccagggtggg ggtcacaagg tgctcagtgg gagagccttt gagccaggat gagccagaag    600
gaatttcaca aggtaatgtc atcagttaag gcagggactg gccatttca cttcttttgt    660 ggtggaatgt catcagttaa ggcaggaacc ggccattttc acttcttttg tgattcttca    720
cttgcttcag gccatctgga cgtataggtg caggtcacag tcacagggga taagatggca    780
atggcatagc ttgggctcag aggcctgaca cctctgagaa actaaagatt ataaaaatga    840
tggtcgcttc tattgcaaat ctgtgtttat tgtcaagagg cacttatttg tcaattaaga    900
acccagtggt agaatcgaat gtccgaatgt aaaacaaaat acaaaacctc tgtgtgtgtg    960
tgtgtgtgag tgtgtgtgta tgtgtgtgtg tgtgtattag agaggaaaag cctgtatttg   1020
gaggtgtgat tcttagattc taggttcttt cctgcccacc ccatatgcac ccaccccaca   1080
aaagaacaaa caacaaatcc caggacatct tagcgcaaca tttcagtttg catattttac   1140
atatttactt tcttacata ttaaaaaact gaaaatttta tgaacacgct aagttagatt   1200
ttaaattaag tttgttttta cactgaaaat aatttaatat ttgtgaagaa tactaataca   1260
ttggtatatt tcattttctt aaaattctga accctcttc ccttatttcc ttttgacccg   1320
attggtgtat tggtcatgtg actcatggat ttgccttaag gcaggagg               1368

<210> SEQ ID NO 34
<211> LENGTH: 755
<212> TYPE: DNA
<213> ORGANISM: Homo sapiens
<220> FEATURE:
<221> NAME/KEY: misc_feature
<223> OTHER INFORMATION: sequence of STAR34

<400> SEQUENCE: 34
actgggcacc ctcctaggca ggggaatgtg agaactgccg ctgctctggg gctgggcgcc     60
atgtcacagc aggagggagg acggtgttac accacgtggg aaggactcag ggtggtcagc    120
cacaaagctg ctggtgatga ccaggggctt gtgtcttcac tctgcagccc taacacccag    180
gctgggttcg ctaggctcca tcctgggggt gcagaccctg agagtgatgc cagtgggagc    240
ctcccgcccc tccccttcct cgaaggccca ggggtcaaac agtgtagact cagaggcctg    300
agggcacatg tttatttagc agacaaggtg gggctccatc agcggggtgg cctggggagc    360
agctgcatgg gtggcactgt ggggagggtc tcccagctcc ctcaatggtg ttcgggctgg    420
tgcggcagct ggcggcaccc tggacagagg tggatatgag ggtgatgggt ggggaaatgg    480
gaggcacccg agatggggac agcagaataa agacagcagc agtgctgggg ggcaggggga    540
tgagcaaagg caggcccaag accccagcc cactgcaccc tggcctccca caagcccct    600 cgcagccgcc cagccacact cactgtgcac tcagccgtcg atacactggt ctgttaggga    660
gaaagtccgt cagaacaggc agctgtgtgt gtgtgtgcgt gtatgagtgt gtgtgtgtga    720
tccctgactg ccaggtcctc tgcactgccc ctggg                              755

<210> SEQ ID NO 35
<211> LENGTH: 1193
<212> TYPE: DNA
<213> ORGANISM: Homo sapiens
```

```
<220> FEATURE:
<221> NAME/KEY: misc_feature
<223> OTHER INFORMATION: sequence of STAR35
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (422)..(423)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
```

-continued

```
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (761)..(761)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (868)..(868)
<223> OTHER INFORMATION: n is a, c, g, or t
<220> FEATURE:
<221> NAME/KEY: misc_feature
<222> LOCATION: (880)..(881)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (925)..(925)
<223> OTHER INFORMATION: n is a, c, g, or t
<220> FEATURE:
<221> NAME/KEY: misc_feature
<222> LOCATION: (1019)..(1019)
<223> OTHER INFORMATION: n is a, c, g, or t
<220> FEATURE:
<221> NAME/KEY: misc_feature
<222> LOCATION: (1021)..(1021)
<223> OTHER INFORMATION: n is a, c, g, or t
<220> FEATURE:
<221> NAME/KEY: misc_feature
<222> LOCATION: (1055)..(1055)
<223> OTHER INFORMATION: n is a, c, g, or t
<220> FEATURE:
<221> NAME/KEY: misc_feature
<222> LOCATION: (1062)..(1063)
<223> OTHER INFORMATION: n is a, c, g, or t
<220> FEATURE:
<221> NAME/KEY: misc_feature
<222> LOCATION: (1074)..(1074)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t
<220> FEATURE:
<221> NAME/KEY: misc_feature
<222> LOCATION: (1100)..(1101)
<223> OTHER INFORMATION: n is a, c, g, or t
<220> FEATURE:
<221> NAME/KEY: misc_feature
<222> LOCATION: (1106)..(1107)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1138)..(1138)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1145)..(1146)
```

```
<223> OTHER INFORMATION: n is a, c, g, or t
<220> FEATURE:
<221> NAME/KEY: misc_feature
<222> LOCATION: (1158)..(1159)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1187)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t

<400> SEQUENCE: 35
cgacttggtg atgcgggctc ttttttggtt ccatatgaac tttaaagtag tcttttccaa      60
ttctgtgaag aaagtcattg gtaggttgat ggggatggca ttgaatctgt aaattacctt     120
gggcagtatg gccattttca caatgttgat tcttcctatc catgatgatg gaatgttctt     180
ccattagttt gtatcctctt ttatttcctt gagcagtggt ttgtagttct ccttgaagag     240
gtccttcaca tcccttgtaa gttggattcc taggtatttt attctctttg aagcaaattg     300
tgaatgggag tncactcacg atttggctct ctgtttgtct gctgggtgta taaanaatgt     360
ngtgatnttn gtacattgat ttngtatccn tgagacttng ctgaatttgc ttnatcngct     420
tnngggaacc ttttgggctg aaacnatggg attttctaaa tatacaatca tgtcgtctgc     480
aaacagggaa caatttgact tcctcttttc ctaattgaat acactttatc tccttctcct     540
gcctaattgc cctgggcaaa acttccaaca ctatgntngn aataggagnt ggtgagagag     600
ggcatccctg ttcttgttgc cagnttttca aagggaatgc ttccagtttt ggcccattca     660
gtatgatatg ggctgtgggt ngtgtcataa atagctctta tnattttgaa atgtgtccca     720
tcaataccta atttattgaa agtttttagc atgaangcat ngttgaattt ggtcaaaggc     780
tttttctgca tctatggaaa taatcatgtg gttttttgtct ttggctcntg tttatatgct     840
ggatnacatt tattgatttg tgtatatnga acccagcctn ncatcccagg gatgaagccc     900
acttgatcca agcttggcgc gcngnctagc tcgaggcagg caaaagtatg caaagcatgc     960
atctcaatta gtcagcaccc atagtccgcc cctacctccg cccatccgcc cctaactcng    1020
nccgttcgcc cattctcgcc catggctgac taatnttttt annatccaag cggngccgcc    1080
ctgcttganc attcagagtn nagagnnttg gaggccnagc cttgcaaaac tccggacngn    1140
ttctnnggat tgaccccnnt taaatatttg gttttttgtn ttttcanngg nga          1193

<210> SEQ ID NO 36
<211> LENGTH: 1712
<212> TYPE: DNA
<213> ORGANISM: Homo sapiens
<220> FEATURE:
<221> NAME/KEY: misc_feature
<223> OTHER INFORMATION: sequence of STAR36

<400> SEQUENCE: 36
gatcccatcc ttagcctcat cgatacctcc tgctcacctg tcagtgcctc tggagtgtgt      60
gtctagccca ggcccatccc ctggaactca ggggactcag gactagtggg catgtacact     120
tggcctcagg ggactcagga ttagtgagcc ccacatgtac acttggcctc agtgactca      180 ggactagtga gccccacatg tacacttggc ctcagggac tcaggattag tgagccccca     240
```

| | |
|---|---|
| catgtacact tggcctcagg ggactcagga ttagtgagcc ccacatgtac acttggcctc | 300 |
| aggggactca ggactagtga gccccacatg tacacttggc ctcaggggac tcagaactag | 360 |
| tgagccccac atgtacactt ggcttcaggg gactcaggat tagtgagccc cacatgtaca | 420 |
| cttggacacg tgaaccacat cgatgtgctg cagagctcag ccctctgcag atgaaatgtg | 480 |
| gtcatggcat tccttcacag tggcacccct cgttccctcc ccacctcatc tcccattctt | 540 |
| gtctgtcttc agcacctgcc atgtccagcc ggcagattcc accgcagcat cttctgcagc | 600 |
| accccgacc acacacctcc ccagcgcctg cttggccctc cagcccagct cccgcctttc | 660 |
| ttccttgggg aagctccctg gacagacacc ccctcctccc agccatggct tttcctgct | 720 |
| ctgccccacg cgggaccctg ccctggatgt gctacaatag acacatcaga tacagtcctt | 780 |
| cctcagcagc cggcagaccc agggtggact gctcggggcc tgcctgtgag gtcacacagg | 840 |
| tgtcgttaac ttgccatctc agcaactagt gaatatgggc agatgctacc ttccttccgg | 900 |
| ttccctggtg agaggtactg gtggatgtcc tgtgttgccg ccaccttttt gtccctggat | 960 |
| gccatttatt ttttccaca aatatttccc aggtctcttc tgtgtgcaag gtattagggc | 1020 |
| tgcagcgggg gccaggccac agatctctgt cctgagaaga cttggattct agtgcaggag | 1080 |
| actgaagtgt atcacaccaa tcagtgtaaa ttgttaactg ccacaaggag aaaggccagg | 1140 |
| aaggagtggg gcatggtggt gttctagtgt tacaagaaga agccagggag ggcttcctgg | 1200 |
| atgaagtggc atctgacctg ggatctggag gaggagaaaa atgtcccaaa agagcagaga | 1260 |
| gcccacccta ggctctgcac caggaggcaa cttgctgggc ttatggaatt cagagggcaa | 1320 |
| gtgataagca gaaagtcctt gggggccaca attaggattt ctgtcttcta aagggcctct | 1380 |
| gccctctgct gtgtgacctt gggcaagtta cttcacctct agtgctttgg ttgcctcatc | 1440 |
| tgtaaagtgg tgaggataat gctatcacac tggttgagaa ttgaagtaat tattgctgca | 1500 |
| aagggcttat aagggtgtct aatactagta ctagtaggta cttcatgtgt cttgacaatt | 1560 |
| ttaatcatta ttattttgtc atcaccgtca ctcttccagg ggactaatgt ccctgctgtt | 1620 |
| ctgtccaaat taaacattgt ttatccctgt gggcatctgg cgaggtggct aggaaagcct | 1680 |
| ggagctgttt cctgttgacg tgccagacta gt | 1712 |

<210> SEQ ID NO 37
<211> LENGTH: 1321
<212> TYPE: DNA
<213> ORGANISM: Homo sapiens
<220> FEATURE:
<221> NAME/KEY: misc_feature
<223> OTHER INFORMATION: sequence of STAR37

<400> SEQUENCE: 37

| | |
|---|---|
| aggatcacat ttaaggaagt gtgtggggtc cctggatgac accagcaccc agtgcggctc | 60 |
| tgtctggcaa ccgctcccaa ggtggcagga gtgggtgtcc cctgtgtgtc agtgggcagc | 120 |
| tcctgctgag cctacagctc actggggagc ctgacagcgg ggccatgtgc ctgacactcc | 180 |
| tctctgcttg tggacctggc aaggcaggga gcagaaaaca gagccacttg aaggctttct | 240 |
| gtctgcgtct gtgtgcagtg tggatttagt tgtgcttttt tcttgctggg agagcacagc | 300 |
| caccatttac aagcagtgtc accctcatgg gtggcgagga cagaacagga gcctctgctc | 360 |
| tctgtaccta tctgggcccg gtgggctccc ttgtcctggc ttccatctct gtctcagcga | 420 |
| ccattcagcc ctgcgcagga acacatgttg cttagaaaag ccaaattcag cccttgtctc | 480 |
| tgcctcctct ggtctcatga tgtgcatctg ttaccttgaa actggaaacc agtctatcaa | 540 |

```
tgtctgtgcc aatttttat tccctcccca acctccttcc ccatacgact tttattttat       600
gtaggatgtg tgctgtctaa tgatgggatg accacatttt tccatgttct aaaagtgctc       660
ctctcccgca gggtcccagg gctggtggtt gctttgggtc tacagctacg tcttacccgc       720
ctcctgcctc aacagcctgt gtggtggcaa agccggtgtg gggctgggga acgcagcgtt       780
ctccaggagg gggacccggc tctccttctg cagtgcaggc gaaggcctag atgccagtgt       840
gacctcccac aaggcgtggc ttccagactc cccggctgga agtgatgctt ttttgcctcc       900
ggccctgggt ttgaagcagc ctggctttct cttggtaagt ggctggtgtc ttagcagctg       960
caatctgagc tcagccacct acacaccacc gtggccgaca ctttcattaa aaagtttcct      1020
gagacgactt gcgtgcatgt tgacttcatg atcagcgccg ctgggaagaa cccctgagcc      1080
ggtggggtgg ggctggaagc agcaggtgca gtgatgggc tggtgccca ggaggcctca       1140 gtgctcaatc aggccaaggt ggccaagccc aggctgcagg gaaggccggc ctgggggttg       1200
tgggtgagca caggcaggca ccagctgggc agtgttagga tgctggagca gcatccgtaa       1260
ccccactgag tggggtagtc tggttgggggc agggaccgct gttgctttgg cagagagaga      1320
t                                                                      1321
```

<210> SEQ ID NO 38
<211> LENGTH: 1445
<212> TYPE: DNA
<213> ORGANISM: Homo sapiens
<220> FEATURE:
<221> NAME/KEY: misc_feature
<223> OTHER INFORMATION: sequence of STAR38
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (949)..(949)
<223> OTHER INFORMATION: n is a, c, g, or t

<400> SEQUENCE: 38

```
gatctatggg agtagcttcc ttagtgagct ttcccttcaa atactttgca accaggtaga        60
gaattttgga gtgaaggttt tgttcttcgt ttcttcacaa tatggatatg catcttcttt       120
tgaaaatgtt aaagtaaatt acctctcttt tcagatactg tcttcatgcg aacttggtat       180 cctgttttcca tccagccttt ctataaccca gtaacatctt ttttgaaacc agtgggtgag      240
aaagacacct ggtcaggaac gcggaccaca ggacaactca ggctcaccca cggcatcaga       300
ctaaaggcaa acaaggactc tgtataaagt accggtggca tgtgtatnag tggagatgca       360
gcctgtgctc tgcagacagg gagtcacaca gacacttttc tataatttct taagtgcttt       420
gaatgttcaa gtagaaagtc taacattaaa tttgattgaa caattgtata ttcatggaat       480
attttggaac ggaataccaa aaaatggcaa tagtggttct ttctggatgg aagacaaact       540
tttcttgttt aaaataaatt ttattttata tatttgaggt tgaccacatg accttaagga       600
tacatataga cagtaaactg gttactacag tgaagcaaat taacatatct accatcgtac       660
atagttacat ttttttgtgt gacaggaaca gctaaaatct acgtatttaa caaaaatcct       720
```

```
aaagacaata catttttatt aactatagcc ctcatgatgt acattagatc gtgtggttgt    780
ttcttccgtc cccgccacgc cttcctcctg ggatggggat tcattcccta gcaggtgtcg    840
gagaactggc gcccttgcag ggtaggtgcc ccggagcctg aggcgggnac tttaanatca    900
gacgcttggg ggccggctgg gaaaaactgg cggaaaatat tataactgna ctctcaatgc    960
cagctgttgt agaagctcct gggacaagcc gtggaagtcc cctcaggagg cttccgcgat   1020
gtcctaggtg gctgctccgc ccgccacggt catttccatt gactcacacg cgccgcctgg   1080
aggaggaggc tgcgctggac acgccggtgg cgcctttgcc tgggggagcg cagcctggag   1140
ctctggcggc agcgctggga gcggggcctc ggaggctggg cctggggacc caaggttggg   1200
cggggcgcag gaggtgggct cagggttctc cagagaatcc ccatgagctg acccgcaggg   1260
cggccgggcc agtaggcacc gggcccccgc ggtgacctgc ggacccgaag ctggagcagc   1320
cactgcaaat gctgcgctga ccccaaatgc tgtgtccttt aaatgtttta attaagaata   1380
attaataggt ccgggtgtgg aggctcaagc cttaatcccc agcacctggc gaggccgagg   1440
aggga                                                               1445
```

<210> SEQ ID NO 39
<211> LENGTH: 2331
<212> TYPE: DNA
<213> ORGANISM: Homo sapiens
<220> FEATURE:
<221> NAME/KEY: misc_feature
<223> OTHER INFORMATION: sequence of STAR39

<400> SEQUENCE: 39

```
gtgaaataga tcactaaagc tgattcctct tgtctaaatg aaactttcta cccttttgatg    60 gacagctatg ctttccccat cctctcccgt cccccagccc ttggtaacca tcatcctact   120
ctctacttgt aggagttcaa cttgtttaga ttttgtgagt gagaacatgt ggtatttgcc   180
tttagagtcc tctaggttta tccatattgt gttaaatgac aggattccct gccttttaa    240 ggctgaatag tatttcattg taatatatat acatacacac acacatatac acacacatat   300
atatacatat atacatatat gtacatagat acatatatat gtacatatat acacacacat   360
atacacacat atatacacat atatacatat acatatatac acatatatgt acatatatat   420 aactttttt catttatcca ttcacttaat acatatgatg gagggcttta tatatgccag    480
gctctgtgat gaatgctgga aattcaatag tgagaaagac tcagtctctg cctccaaaga   540
gcatcatggg ctaggtgctg caacgaggaa ttgccaactg ttgtcatgag agcacagaga   600
agggactcaa ccagccttga agaatcaggg gaggcttcta agctaatggt gtgtgcctgg   660
ggatcacatt gtttcaagca gcagtaacag gatgtgctca ggtccagatg tgagagagag   720
agagagcata tgtcttcaag aaactaacag tagctcccta tagctgaagc aggagtacaa   780
aatagtgagt ttaagtgatg aggcaagaga tatgaagaag cttgaccatg cagctacacc   840
gggcagcatg ccctctgaga catctcatgg aagccggaaa tgggagtgcc ttgataccaa   900
gccagagaaa ttataatact aagtagatag actgagcagc actcctcctg ggaagaatga   960
gacaagccct gaatttggag gtaagttgtg gattggtgat tagaggagag gtaacaggca  1020
ccaaagcaag aaatagtatt gatgcaaagc tgaggttaat tggatgacaa aatgaagagc  1080
ataaggggct cagacacaga ctgagcagaa aacgagtagc atctgaacct agattgagtt  1140
actaatggat gagaaagagt tcttaaagtt gatgaccacg ggatccatat ataagaatgt  1200
ccaatctccc caaattgatc cacgagttca gtgcaatgcc aatcaaaatc ccactaacaa  1260
```

| | | |
|---|---|---|
| gtttatttta aaatgtaaat gaaaatacaa aattttaaa aagcaaagca atattgaaaa | 1320 | |
| cccaggaaaa attaggagga cttacacaac ctgatctcaa aacttaccat tatcaagaca | 1380 | |
| gagtgttatt gacacaagga gagacaaata gataaacgga atgtggtagt ctggagatgc | 1440 | |
| acccacatgt atgtggtcaa ttgatttttg gccaaggcac caagtcaatt caaaggagca | 1500 | |
| aggaaagtag tacagaaaca accaaatatt gttttggaaa ataatgacaa agggcttata | 1560 | |
| accagaatat aagcatataa atataattct ttcaaatcaa taataagaag gcaaatatct | 1620 | |
| aataaaaatg agcaaagact tgaaaagtca cttaaaaagg cttattaatt agaaatatgc | 1680 | |
| aaatgttatt agtcttcagt ggaatttaca ttaaaccaca agggatacta ttatatctta | 1740 | |
| tgcccactag aataaccaaa ggaaaaaaga cagacaaaac aaaatgctgg tgaggatgtg | 1800 | |
| aagcaactgg aactctcata cattattggt ggtaatgtaa aatttataca accattatga | 1860 | |
| ataaaggttt ggcagtttct tacaaagttg aatgcacttc tccacgatga ctaggctttt | 1920 | |
| cactcatagg cgtctggctc cctagaactg aaaacatatg ttcacaagaa gacttgcaaa | 1980 | |
| tatatattct cccacgtcag gagatatttg ctatgcattt aactgacata agattagtgc | 2040 | |
| tagagtttat aatgaggttc ttcaaatcta aagaaaatg caaagcatat aatagtaagg | 2100 | |
| ggtgcaggcc aggcgcagtg gctcactctg taatcccagc actttgggag gccgaggtgg | 2160 | |
| gcggatcaca aggtcaggag ttcgagacca acctggccaa catagtgaaa ccctgtctct | 2220 | |
| actaaaaata caaaaactag ccaggtgcgg tgtcatgcac ctgtagtccc agctactcgg | 2280 | |
| gaggccgagg caggagaatc acttgaacct gggaggtgga ggttgcagtg a | 2331 | |

<210> SEQ ID NO 40
<211> LENGTH: 1071
<212> TYPE: DNA
<213> ORGANISM: Homo sapiens
<220> FEATURE:
<221> NAME/KEY: misc_feature
<223> OTHER INFORMATION: sequence of STAR40

<400> SEQUENCE: 40

| | | |
|---|---|---|
| gctgtgattc aaactgtcag cgagataagg cagcagatca agaaagcact ccgggctcca | 60 | |
| gaaggagcct tccaggccag cttttgagcat aagctgctga tgagcagtga gtgtcttgag | 120 | |
| tagtgttcag ggcagcatgt taccattcat gcttgacttc tagccagtgt gacgagaggc | 180 | |
| tggagtcagg tctctagaga gttgagcagc tccagcctta gatctcccag tcttatgcgg | 240 | |
| tgtgcccatt cgctttgtgt ctgcagtccc ctggccacac ccagtaacag ttctgggatc | 300 | |
| tatgggagta gcttccttag tgagcttcc cttcaaatac tttgcaacca ggtagagaat | 360 | |
| tttggagtga aggttttgtt cttcgttct tcacaatatg gatatgcatc ttcttttgaa | 420 | |
| aatgttaaag taaattacct ctcttttcag atactgtctt catgcgaact tggtatcctg | 480 | |
| tttccatccc agccttctat aacccagtaa catctttttt gaaaccagtg ggtgagaaag | 540 | |
| acacctggtc aggaacgcgg accacaggac aactcaggct cacccacggc atcagactaa | 600 | |
| aggcaaacaa ggactctgta taaagtaccg gtggcatgtg tattagtgga gatgcagcct | 660 | |
| gtgctctgca gacagggagt cacacagaca cttttctata atttcttaag tgctttgaat | 720 | |
| gttcaagtag aaagtctaac attaaatttg attgaacaat tgtatattca tggaatattt | 780 | |
| tggaacggaa taccaaaaaa tggcaatagt ggttctttct ggatggaaga caaacttttc | 840 | |
| ttgtttaaaa taaattttat tttatatatt tgaggttgac cacatgacct taaggataca | 900 | |
| tatagacagt aaactggtta ctacagtgaa gcaaattaac atatctacca tcgtacatag | 960 | |

```
ttacattttt ttgtgtgaca ggaacagcta aaatctacgt atttaacaaa aatcctaaag    1020
acaatacatt tttattaact atagccctca tgatgtacat tagatctcta a             1071

<210> SEQ ID NO 41
<211> LENGTH: 1135
<212> TYPE: DNA
<213> ORGANISM: Homo sapiens
<220> FEATURE:
<221> NAME/KEY: misc_feature
<223> OTHER INFORMATION: sequence of STAR41

<400> SEQUENCE: 41
cgtgtgcagt ccacggagag tgtgttctcc tcatcctcgt tccggtggtt gtggcgggaa      60
acgtggcgct gcaggacacc aacatcagtc acgtatttca ttctggaaaa aaaagtagca     120
caagcctcgg ctggttccct ccagctctta ccaggcagcc taagcctagg ctccattccc     180
gctcaaggcc ttcctcaggg gcctgctcac cacaggagct gttcccatgc agggactaag     240
gacatgcagc ctgcatagaa accaagcacc caggaaaaca tgattggatg gagcggggg     300 gtgtggtctc tagccttgtc cacctccggt cctcatgggt ctcacacctc ctgagaatgg    360
gcaccgcaga ggccacagcc catacagcca agatgacaga ctccgtaagt gacagggatc     420
cacagcagag tgggtgaaat gttccctata aactttacaa aattaatgag ggcaggggga    480
ggggagaaat gaaatgaac ccagctcgca gcacatcagc atcagtcact aggtcggcgt     540
gctctctgac tgcttcctcg tagctgcttg gtgtctcatt gcctcagaag catgtagacc    600
ctgtcacaag attgtagttc ccctaactgc tccgtagatc acaacttgaa ccttaggaaa    660
tgctgttttc cctttgagat attcctttgg gtcctgtata ctgatggagc tactgactga    720
gctgctccga aggaccccac gaggagctga ctaaaccaag agtgcagttt gtacaccctg    780
atgattacat ccccccttgcc ccaccaatca actctcccaa ttttccagcc cctcacccctc   840 cagtcccctt aaaagcccca gcccaggccg ggcacagtgg ctcatgcctg taatcccagc    900
actttgggag gccaaggtgg gcagatcacc tgagggcagg aatttgagac cagcctgacc    960
aacatgaaga aacccgtctc tattacaaa tacaaaatta gccggcgtg ttgctgcata     1020 ctggtaatcc cagctacttg ggagggtgag gcaggagaat cacttgaatc tgggaggcgg    1080
aggttgcgat gagccgagac agcgccattg cactgcagcc tgggcaacaa gagca          1135

<210> SEQ ID NO 42
<211> LENGTH: 735
<212> TYPE: DNA
<213> ORGANISM: Homo sapiens
<220> FEATURE:
<221> NAME/KEY: misc_feature
<223> OTHER INFORMATION: sequence of STAR42

<400> SEQUENCE: 42
aagggtgaga tcactaggga gggaggaagg agctataaaa gaaagaggtc actcatcaca      60
tcttacacac ttttaaaac cttggttttt taatgtccgt gttcctcatt agcagtaagc    120
cctgtggaag caggagtctt tctcattgac caccatgaca agaccctatt tatgaaacat    180
aatagacaca caaatgttta tcggatattt attgaaatat aggaattttt cccctcacac    240
ctcatgacca cattctggta cattgtatga atgaatatac cataatttta cctatggctg    300
tatatttagg tctttttcgtg caggctataa aaatatgtat gggccggtca cagtgactta    360
cgcccgtagt cccagaactt tgggaggccg aggcgggtgg atcacctgag gtcgggagtt    420
caaaaccagc ctgaccaaca tggagaaacc ccgtctctgc taaaaataca aaattaact    480
```

```
ggacacggtg gcgtatgcct gtaatcccag ctactcggga agctgaggca ggagaactgc    540
ttgaacccag gaggcggagg ttgtggtgag tcgagattgc gccattgcac tccagcctgg    600
gcaacaagag cgaaattcca tctcaaaaaa aagaaaaaag tatgactgta tttagagtag    660
tatgtggatt tgaaaaatta ataagtgttg ccaacttacc ttagggttta taccatttat    720
gagggtgtcg gtttc                                                     735
```

<210> SEQ ID NO 43
<211> LENGTH: 1227
<212> TYPE: DNA
<213> ORGANISM: Homo sapiens
<220> FEATURE:
<221> NAME/KEY: misc_feature
<223> OTHER INFORMATION: sequence of STAR43

<400> SEQUENCE: 43

```
caaatagatc tacacaaaac aagataatgt ctgcccattt ttccaaagat aatgtggtga     60
agtgggtaga gagaaatgca tccattctcc ccacccaacc tctgctaaat tgtccatgtc    120
acagtactga gaccagggggg cttattccca gcgggcagaa tgtgcaccaa gcacctcttg   180
tctcaatttg cagtctaggc cctgctattt gatggtgtga aggcttgcac ctggcatgga   240
aggtccgttt tgtacttctt gctttagcag ttcaaagagc agggagagct gcgagggcct   300
ctgcagcttc agatggatgt ggtcagcttg ttggaggcgc cttctgtggt ccattatctc   360 cagccccct gcggtgttgc tgtttgcttg gcttgtctgg ctctccatgc cttgttggct   420
ccaaaatgtc atcatgctgc accccaggaa gaatgtgcag gcccatctct tttatgtgct   480
ttgggctatt ttgattcccc gttgggtata ttccctaggt aagacccaga agacacagga   540
ggtagttgct ttgggagagt ttggacctat gggtatgagg taatagacac agtatcttct   600 cttttcatttg gtgagactgt tagctctggc cgcggactga attccacaca gctcacttgg   660
gaaaacttta ttccaaaaca tagtcacatt gaacattgtg gagaatgagg acagagaag   720 aggccctaga tttgtacatc tgggtgttat gtctataaat agaatgcttt ggtggtcaac   780
tagacttgtt catgttgaca tttagtcttg ccttttcggt ggtgatttaa aaattatgta   840
tatcttgttt ggaatatagt ggagctatgg tgtggcattt tcatctggct ttttgtttag   900
ctcagcccgt cctgttatgg gcagccttga agctcagtag ctaatgaaga ggtatcctca   960
ctccctccag agagcggtcc cctcacggct cattgagagt ttgtcagcac cttgaaatga  1020
gtttaaactt gtttatttt aaaacattct tggttatgaa tgtgcctata ttgaattact  1080
gaacaacctt atggttgtga agaattgatt tggtgctaag gtgtataaat ttcaggacca  1140
gtgtctctga agagttcatt tagcatgaag tcagcctgtg gcaggttggg tggagccagg  1200
gaacaatgga gaagctttca tgggtgg                                      1227
```

<210> SEQ ID NO 44
<211> LENGTH: 1586
<212> TYPE: DNA
<213> ORGANISM: Homo sapiens
<220> FEATURE:
<221> NAME/KEY: misc_feature
<223> OTHER INFORMATION: sequence of STAR44

<400> SEQUENCE: 44

```
cacctgcctc agcctcccaa agtgctgaga ttcaaagaaa ttttcatgga gaggggacag     60
atggagtcaa ttcttgtggg gtgaacatga gtaccacagt tagactgagg ttgggaaaga   120
```

```
ttttccagac aattggaaga gcatgtgaaa gacacagatt ttgagaaatg ttaagtctag      180
ggaactgcaa ggcttttggc acaagaaagc cactgtagac tatagaggca ggatgcctag      240
attcaaatcc caactgctac acttctaagc tttgtaattt tggcaagttt ttaccctcta      300
ttttcttatc tataaaatat agattttata tatatagata tagatatata gatagataat      360
aattgtgcat gcctaataaa gttgtcaaag attaaatgtt atatgtgaag tattttgtac      420
ggtgatagga acccaggaag ggctctatga atattatgta ttattattat tctaaagtag      480
ctggaataca atgttcaaag gagatagtgg caggagataa gtttgaattg aaagattgag      540
gccagaacat aaagtgcctc ctatattata ttttacataa ttggaacatc attgaaaaat      600
ttaagtatta tttatgtgtg tatgtgtgtt ttatataatt aattctagtt catcatttta      660
aaatatcttt ctgatgtcac tgtgaacaac agatgagaag aagtgaatcc tgagttaagg      720
agaccagctc tctgattact gccataatcc agggagggta ccataaggat ttcaactgga      780
agtgaatcca tcatgatgga gaggaaggac agggctgaaa atacttagg aagtagtatc       840
agtaggactg gttaagagag agcagaggca ggctacaggg gttggaggtg tcaatcacag      900
agatagggaa aatgggagga gaagcaggct ttgaaaaagt ggcttgtctt gtaaaattat      960
gtgctgttaa aacagtacaa gaaattaata tattcaatcc caaaatacag ggacaattct     1020
ttttgaaaga gttacccaga tagtcttcct tgaagttttc agttaaagaa atttcttgtt     1080
aacaaataat gtagtcatag aagaaaacac ttaaaacttt attgaataaa gctaataaat     1140
catttaatat aatttatagg aaattgttac ataacacaca cattcaatac ttttgctaa     1200
agtataaatt aatggaagga gagcacgcac acagaggttg aattatgttt atgactttat     1260
tagtcaagaa tacaaaattg agtagctaca tcaagcagaa gcacatgctt tacaatccag     1320
cacagaatcc cttgacatcc aaactcccga aacagacatg taaatacaga tgacattgtc     1380
agaacaaaat agggtctcac ccgacctata atgttctttt cttgatataa atatgcacat     1440
gaattgcata cggtcatatg gttccaatta ccattatttc ctctgggctt agctatccat     1500
ctaaggggaa tttacaccaa cactgtactt ctacttgcaa gaatatatga aagcatagtt     1560
aacttctggc ttaggacccc aactca                                           1586

<210> SEQ ID NO 45
<211> LENGTH: 1981
<212> TYPE: DNA
<213> ORGANISM: Homo sapiens
<220> FEATURE:
<221> NAME/KEY: misc_feature
<223> OTHER INFORMATION: sequence of STAR45

<400> SEQUENCE: 45
atggatcata gggtaaataa atttataatt tcttgagaaa gcttcgtact gttttccaag       60
atggctgtac taatttccat tcctaccaac agtgtacagg gtttcttttt ctccacatcc      120
tcaccaacac ttatcttcca tcttttttta taatagccct agtaaaatgt gtgaggtgat      180
atctcattgt ggcattgatt tgcacttctc tgataattag gaatgtttat gattttttca      240
tgtacctggt tggccttttg tatgatgtag gaaatgtcta ttctgattct ttgcttattt      300
tttaataagc atagtttttt tcttattttt gagtaggtta agttgcttat atattattat      360
atgagcccct tacctgatgt atggtttaaa aatattatcc catttgtggg ttctcttaat      420
tctatcattg cttcttttcc tgtggaaaag ttttaagttt tatgcagtct catttgtgtg      480
ttttgctttt gttgcctttt ggaataatct acagaaaatc atagctcagg ccaatgtcat      540
```

| | |
|---|---|
| acagtctcct tctatatttc cttgtagtag ttttacattt aaactttaat tttgatttga | 600 |
| tgcttgtata aagagcaaaa taaaagtcaa attttattct tctgtatgtg gatagtcagt | 660 |
| tttgtctaca ccatttattg aaaataattt tctttcttca ctgtgtattt ttagttattt | 720 |
| tatcaaaaaa tcaattgacc acagacacac ggatttattt acaggttcta tatccctttg | 780 |
| tactgtttta catgtctgtt tttatgccat tgctatgctg ttttaattcc tatagctttg | 840 |
| taatagagtt tggagtcagg tagtctgatg cctccagctt tgttcttttt gttcaagatt | 900 |
| gctttggttg gtccaggtct tttgtggttc catacaaatt ttagcagtaa ttttctatt | 960 |
| tctgtgaaga atgacattgg aatttgatag tggttgcatt taatctgtag attgctttgg | 1020 |
| gtagcattga cacttttaca atactaattt ttgaatccat caatgaagga tgtttctcca | 1080 |
| tttatttatg ccatttaat ttttttcatc aatgtgctat agtttcagt atgtaaatct | 1140 |
| tttatggttt tgattaaatt tactcctgtc ttttatatat ttatatatct gttttgattc | 1200 |
| tattataaat tgaattgcct ttattttca ggtaatagtt tgtcattagt taatagaaac | 1260 |
| aataatgata tttgtatgtt gattttgtaa ctattaactt tattgaattt cttcatcagc | 1320 |
| tataaccatt tattttggtg gaatcttaa gattttctct atcttaagat tatattttca | 1380 |
| aaaaacagaa acaatcttac ctcttccttc cctatgtgga tttctttac gtctttgtct | 1440 |
| tgtgtaactg ttctggctag gcaattacac ataatgtttt catcatttat aattttacat | 1500 |
| cacatccatc tattgtggca cattgattgc tacttttcaa gttgtaaacc tggacattta | 1560 |
| tcactactct tcctccaata caggagtcca tggcgtggtg tgggccctac tgtgccacag | 1620 |
| tccagggcac ggctgggctg aggttctctt gtgcaagagt ccgtggctct gcggagcaag | 1680 |
| agttctccag tgccttagtc cagggttagg cagggtggg gctccttcag tagcttagtc | 1740 |
| cagtgcgccg ccctgcgagg gtcctcctga gcaggagtac acgatgaggc agggtcctac | 1800 |
| tgtgccttag cccaggaagc ggggggctgg gtcctctggt gccatagtcc aggctgccgg | 1860 |
| gagctgggtc ctctggtgcc atagctcagg ccggcgggag ctgggtcctc tggtgccgta | 1920 |
| gtccagggtg cagcagaaca ggagtcctgc ggagcagtag tccagggcac gctggggcgt | 1980 |
| g | 1981 |

<210> SEQ ID NO 46
<211> LENGTH: 1859
<212> TYPE: DNA
<213> ORGANISM: Homo sapiens
<220> FEATURE:
<221> NAME/KEY: misc_feature
<223> OTHER INFORMATION: sequence of STAR46

<400> SEQUENCE: 46

| | |
|---|---|
| attgtttttc tcgcccttct gcattttctg caaattctgt tgaatcattg cagttactta | 60 |
| ggtttgcttc gtctccccca ttacaaacta cttactgggt ttttcaaccc tagttccctc | 120 |
| attttttatga tttatgctca tttctttgta cacttcgtct tgctccatct cccaactcat | 180 |
| ggcccctggc tttggattat gttttggtc ttttattttt tgtcttcttc tacctcaaca | 240 |
| cttatcttcc tctcccagtc tccggtaccc tatcaccaag gttgtcatta acctttcata | 300 |
| ttattcctca ttatccatgt attcatttgc aaataagcgt atattaacaa atcacaggt | 360 |
| ttatggagat ataattcaca taccttaaaa ttcaggcttt taaagtgtac cttttcatgtg | 420 |
| gttttttggta tattcacaaa gttatgcatt gatcaccacc atctgattcc ataacatgtt | 480 |
| caataacctca aaaagaagtc tgtactcatt agtagtcatt tcacattcac cactccctct | 540 |

```
ggctctgggc agtcactgat ctttgtgtct ctatggattt gcctagtcta ggtattttta      600
tgtaaatggc atcatacaac atgtgacctt tgtttggct tttttcattt agcaaaatgt       660
tatcaaggtc tgtccctgtt gtagcatgta ttagcacttc atttcttata tgctgaatga     720
tatactttat ttgtccatca gttgttcatg ctttatttgt ccatcagttg atgaacattt     780 gcgttttgc cactttgggc tattaagaat aatgctactg tgaacaagtg tgtacaagtt      840
cctctacaaa ttttgtgtg gacatatcct ttcagttctc tcaggtgtat atctgggaat      900
tgaattgctg ggtcgtgtag tagctatgtt aaacactttg agaaactgct ataatgttct    960
ccagagctgt accattttaa attctgtgta tgaggattcc acgttctcca cttcctcacc    1020
agtgtatgga tttgggggta cttttttaa aaagtgggat taggctgggc acagtggctc     1080
acacctgtaa tcccaacact tcaggaagct gaggtgggag gatcacttga gcctagtagt   1140
ttgagaccag cctgggcaac atagggagac cctgtctcta caaaaaataa tttaaaataa   1200
attagctggg cgttgtggca cacctgta gtcccagcta catgggaggc tgaggtggaa      1260
ggattccctg agcccagaag tttgaggttg cagtgagcca tgatggcagc actatactgt   1320
agcctgggtg tcagagcaag actccgtttc agggaagaaa aaaaaagtg ggatgatatt     1380 tttgacactt ttcttcttgt tttcttaatt tcatacttct ggaaattcca ttaaattagc    1440
tggtaccact ctaactcatt gtgtttcatg gctgcatagt aatattgcat aatataaata    1500
taccattcat tcatcaaagt tagcagatat tgactgttag gtgccaggca ctgctctaag    1560
cgttaaagaa aaacacacaa aaacttttgc attcttagag tttatttcc aatggagggg    1620 gtggagggag gtaagaattt aggaaataaa ttaattacat atatagcata gggtttcacc    1680
agtgagtgca gcttgaatcg ttggcagctt tcttagtagt ataaatacag tactaaagat    1740
gaaattactc taaatggtgt tacttaaatt actggaatag gtattactat tagtcacttt    1800
gcaggtgaaa gtggaaacac catcgtaaaa tgtaaaatag gaaacagctg gttaatgtt    1859
```

<210> SEQ ID NO 47
<211> LENGTH: 1082
<212> TYPE: DNA
<213> ORGANISM: Homo sapiens
<220> FEATURE:
<221> NAME/KEY: misc_feature
<223> OTHER INFORMATION: sequence of STAR47

<400> SEQUENCE: 47

```
atcattagtc attagggaaa tgcaaatgaa aaacacaagc agccaccaat atacacctac     60
taggatgatt taaaggaaaa taagtgtgaa gaaggacgta aagaaattgt aaccctgata   120
cattgatggt agaaatggat aaagttgcag ccactgtgaa aaacagtctg cagtggctca   180
gaaggttaaa tatagaaccc ctgttggacc caggaactct actcttaggc accccaaaga  240
atagagaaca gaaatcaaac agatgtttgt atactaatgt ttgtagcatc acttttcaca   300
ggagccaaaa ggtggaaata atccaaccat cagtgaacaa atgaatgtaa taaaagcaag  360
gtggtctgca tgcaatgcta catcatccat ctgtaaaaaa cgaacatcat tttgatagat   420
gatacaacat gggtggacat tgagaacatt atgcttagtg aaataagcca gacacaaaag  480
gaatatattg tataattgta attacatgaa gtgcctagaa tagtcaaatt catacaagag   540
aaagtgggat aggaatcacc atgggctgga ataggggga aggtgctata ctgcttattg   600
tggacaaggt ttcgtaagaa atcatcaaaa ttgtgggtgt agatagtggt gttggttatg   660
caaccctgtg aatatattga atgccatgga gtgcacactt tggttaaaag gttcaaatga   720
```

```
taaatattgt gttatatata tttccccacg atagaaaaca cgcacagcca agcccacatg    780
ccagtcttgt tagctgcctt cctttacctt caagagtggg ctgaagcttg tccaatcttt    840
caaggttgct gaagactgta tgatggaagt catctgcatt gggaagaaaa ttaatggaga    900
gaggagaaaa cttgagaatc cacactactc accctgcagg gccaagaact ctgtctccca    960
tgctttgctg tcctgtctca gtatttcctg tgaccacctc cttttcaac tgaagacttt    1020 gtacctgaag gggttcccag gttttcacc tcggcccttg tcaggactga tcctctcaac    1080
ta                                                                   1082
```

<210> SEQ ID NO 48
<211> LENGTH: 1242
<212> TYPE: DNA
<213> ORGANISM: Homo sapiens
<220> FEATURE:
<221> NAME/KEY: misc_feature
<223> OTHER INFORMATION: sequence of STAR48

<400> SEQUENCE: 48

```
atcatgtatt tgttttctga attaattctt agatacatta atgttttatg ttaccatgaa    60
tgtgatatta taatataata ttttaattg gttgctactg tttataagaa tttcattttc     120
tgtttacttt gccttcatat ctgaaaacct tgctgatttg attagtgcat ccacaaattt    180
tcttggattt tctatgggta attacaaatc tccacacaat gaggttgcag tgagccaaga    240
tcacaccact gtactccagc ctgggcgaca gagtgagaca ccatctcaca aaaacacata    300
aacaaacaaa cagaaactcc acacaatgac aacgtatgtg ctttctttt ttcttcctct    360 ttctataata tttctttgtc ctatcttaac tgaactggcc agaaacccca ggacaatgat    420
aaatacgagc agtgtcaaca gacatctcat tcccttcct agctttata aaaataacga     480 ttatgcttca acattacata tggtggtgtc gatggttttg ttatagataa gcttatcagg    540
ttaagaaatt tgtctgcgtt tcctagtttg gtataaagat tttaatataa atgaatgttg    600 tatttatca tcttattttt ttcctacatc tgctaaggta atcctgtgtt ttcccctttt     660
caatctccta atgtggtgaa tgacattaaa ataccttcta ttgttaaaat attcttgcaa    720
cgctgtatag aaccaatgcc tttattctgt attgctgatg gattttgaa aaatatgtag     780 gtggacttag ttttctaagg ggaatagaat ttctaatata tttaaaatat tttgcatgta    840
tgttctgaag gacattggtg tgtcatttct ataccatctg gctactagag gagccgactg    900
aaagtcacac tgccggagga ggggagaggt gctcttccgt ttctggtgtc tgtagccatc    960
tccagtggta gctgcagtga taataatgct gcagtgccga cagttctgga aggagcaaca    1020
acagtgattt cagcagcagc agtattgcgg atccccacg atggagcaag gaaataatt      1080 ctggaagcaa tgacaatatc agctgtggct atagcagctg agatgtgagt tctcacggtg    1140
gcagcttcaa ggacagtagt gatggtccaa tggcgcccag acctagaaat gcacatttcc    1200
tcagcaccgg ctccagatgc tgagcttgga cagctgacgc ct                       1242
```

<210> SEQ ID NO 49
<211> LENGTH: 1015
<212> TYPE: DNA
<213> ORGANISM: Homo sapiens
<220> FEATURE:
<221> NAME/KEY: misc_feature
<223> OTHER INFORMATION: sequence of STAR49

<400> SEQUENCE: 49

```
aaaccagaaa cccaaaacaa tgggagtgac atgctaaaac cagaaaccca aaacaatggg    60
```

```
agggtcctgc taaaccagaa acccaaaaca atgggagtga agtgctaaaa ccagaaaccc      120
aaaacaatgg gagtgtcctg ctacaccaga aacccaaaac gatgggagtg acgtgataaa      180
accagacacc caaaacaatg ggagtgacgt gctaaaccag aaacccaaaa caatgggagt      240
gacgtgctaa aacctggaaa cctaaaacaa tgcgagtgag gtgctaacac cagaatccat      300
aacaatgtga gtgacgtgct aaaccagaac ccaaaacaat gggagtgacg tgctaaaaca      360
ggaacccaaa acaatgagag tgacgtgcta aaccagaaac ccaaaacaat gggaatgacg      420
tgctaaaacc ggaacccaaa acaatgggag tgatgtgcta aaccagaaac ccaaaacaat      480
gggaatgaca tgctaaaact ggaacccaaa acaatggtaa ctaagagtga tgctaaggcc      540
ctacattttg gtcacactct caactaagtg agaacttgac tgaaaaggag attttttttt      600
tctaagacag agttttggtc tgtcccccag agtggagtgc agtggcatga tctcggctca      660
ctgcaagctc tgcctcccgg gttcaggcca ttctcctgcc tcagcctcct gagtagctgg      720
gaatacaggc acccgccacc acacttggct aattttttgt attttttagta gagatggggt      780 ttcaccatat tagcaaggat ggtctcaatc tcctgacctc gtgatctgcc cacctcaggc      840
tcccaaagtg ctgggattac aggtgtgagc caccacaccc agcaaaaagg aggaatttt       900 aaagcaaaat tatgggaggc cattgttttg aactaagctc atgcaatagg tcccaacaga      960
ccaaaccaaa ccaaaccaaa atggagtcac tcatgctaaa tgtagcataa tcaaa          1015

<210> SEQ ID NO 50
<211> LENGTH: 2355
<212> TYPE: DNA
<213> ORGANISM: Homo sapiens
<220> FEATURE:
<221> NAME/KEY: misc_feature
<223> OTHER INFORMATION: sequence of STAR50

<400> SEQUENCE: 50
caaccatcgt tccgcaagag cggcttgttt attaaacatg aaatgaggga aaagcctagt       60
agctccattg gattgggaag aatggcaaag agagacaggc gtcatttttct agaaagcaat     120 cttcacacct gttggtcctc acccattgaa tgtcctcacc caatctccaa cacagaaatg     180
agtgactgtg tgtgcacatg cgtgtgcatg tgtgaaagta tgagtgtgaa tgtgtctata     240
tgggaacata tatgtgattg tatgtgtgta actatgtgtg actggcagcg tggggagtgc     300
tggttggagt gtggtgtgat gtgagtatgc atgagtggct gtgtgtatga ctgtggcggg     360
aggcggaagg ggagaagcag caggctcagg tgtcgccaga gaggctggga ggaaactata     420
aacctgggca atttcctcct catcagcgag cctttcttgg gcaatagggg cagagctcaa     480
agttcacaga gatagtgcct gggaggcatg aggcaaggcg gaagtactgc gaggagggggc    540 agagggtctg acacttgagg ggttctaatg ggaaaggaaa gacccacact gaattccact     600
tagccccaga ccctgggccc agcggtgccg gcttccaacc ataccaacca tttccaagtg     660
ttgccggcag aagttaacct ctcttagcct cagtttcccc acctgtaaaa tggcagaagt     720
aaccaagctt accttcccgg cagtgtgtga ggatgaaaag agctatgtac gtgatgcact     780
tagaagaagg tctagggtgt gagtggtact cgtctggtgg gtgtggagaa gacattctag     840
gcaatgagga ctggggagag cctggcccat ggcttccact cagcaaggtc agtctcttgt     900
cctctgcact cccagccttc cagagaggac cttcccaacc agcactcccc acgctgccag     960
tcacacatag ttacacacat acaatcacat atatgttccc atatagacac attcacactc    1020
ataccttcac acatgcacac gcatgtgcac acacagtcac tcatttctgt gttggagatt    1080
```

```
gggtgaggac attcaatggg tgaggaccaa caggtgtgaa gattgctttc tagaaaatga   1140
ctcctgtctc tctttgccat tcttcccaat ccgatggagc tactaggctt ttccctcatt   1200
tcatgtttaa taaaccttcc caatggcgaa atgggctttc tcaagaagtg gtgagtgtcc   1260
catccctgcg gtggggacag gggtggcagc ggacaagcct gcctggaggg aactgtcagg   1320
ctgattccca gtccaactcc agcttccaac acctcatcct ccaggcagtc ttcattcttg   1380
gctctaattt cgctcttgtt ttcttttta ttttatcga gaactgggtg gagagctttt      1440
ggtgtcattg gggattgctt tgaaaccctt ctctgcctca cactgggagc tggcttgagt   1500
caactggtct ccatggaatt tcttttttta gtgtgtaaac agctaagttt taggcagctg   1560
ttgtgccgtc cagggtggaa agcagcctgt tgatgtggaa ctgcttggct cagatttctt   1620
gggcaaacag atgccgtgtc tctcaactca ccaattaaga agcccagaaa atgtggcttg   1680
gagaccacat gtctggttat gtctagtaat tcagatggct tcacctggga agcccctttct  1740 gaatgtcaaa gccatgagat aaaggacata tatatagtag ctagggtggt ccacttctta   1800
ggggccatct ccggaggtgg tgagcactaa gtgccaggaa gagaggaaac tctgttttgg    1860
agccaaagca taaaaaaacc ttagccacaa accactgaac atttgttttg tgcaggttct    1920
gagtccaggg agggcttctg aggagagggg cagctggagc tggtaggagt tatgtgagat    1980
ggagcaaggg ccctttaaga ggtgggagca gcatgagcaa aggcagagag gtggtaatgt   2040
ataaggtatg tcatgggaaa gagtttggct ggaacagagt ttacagaata gaaaaattca    2100
acactattaa ttgagcctct actacgtgct cgacattgtt ctagtcactg agataggttt     2160
ggtatacaaa acaaaatcca tcctctatgg acattttagt gactaacaac aatataaata   2220 ataaagtga acaaaagctc aaaacatgcc aggcactatt atttatttat ttatttattt       2280
atttatttat tttttgaaac agagtctcgc tctgttgccc aggctggagt gtagtggtgc   2340
gatctcggct cactg                                                     2355
```

<210> SEQ ID NO 51
<211> LENGTH: 2289
<212> TYPE: DNA
<213> ORGANISM: Homo sapiens
<220> FEATURE:
<221> NAME/KEY: misc_feature
<223> OTHER INFORMATION: sequence of STAR51

<400> SEQUENCE: 51

```
tcacaggtga caccaatccc ctgaccacgc tttgagaagc actgtactag attgactttc    60
taatgtcagt cttcattttc tagctctgtt acagccatgg tctccatatt atctagtaca   120
acacacatac aaatatgtgt gatacagtat gaatataata taaaaatatg tgttataata  180
taaatataat attaaaatat gtctttatac tagataataa tacttaataa cgttgagtgt  240
ttaactgctc taagcacttt acctgcagga aacagttttt tttttatttt ggtgaaatac   300
aactaacata aatttattta caattttaag cattttaag tgtatagttt agtggagtta      360
atatattcaa aatgttgtgc agccgtcacc atcatcagtc ttcataactc ttttcatatt    420
gtaaaattaa aagtttatgc tcatttaaaa atgactccca atttcccccc tcctcaacct    480
ctggaaacta ccattctatt ttctgcctcc gtagttttgc ccactctaag tacctcacat     540
aagtggaatt tgtcttattt gcctgtttgt gaccggctga tttcatttag tataatgtcc    600
tcaagtttta ttcacgttat atagcatatg tcataatttt cttcactttt aagcttgagt    660
aatatttcat cgtatgtatc tcacattttg cttatccatt catctctcag tggacacttg   720
```

```
agttgcttct acattttagc tgttgtgaat actgctgcta tgaacatggg tgtataaata      780
tctcaagacc ttttatcag tttttaaaa tatatactca gtagtagttt agctggatta      840
tatggtaatt ttattttaa tttttgagga actgtcctac cctttattc aatagtagct      900 ataccaattg acaattggca ttcctaccaa cagggcataa gggttctcaa ttctccacat      960
attccctgat acttgttatt ttcaggtgtt tttttttttt tttttttttt atgggagcca     1020
tgttaatggg tgtaaggtga tatttcatta gtgtttgat ttgcatttcc ctaatgatta     1080
gtgatgttaa gcatctcttc atgtgcctat tggccatttg tatatcttct ttaaaaatat     1140
atatatactc attcctttgc ccattttga attatgttta tttttgtta ttgagtttca     1200 atacttttct ataaaccta ggtattaatc ctttatcaga cttaagattt gcaaatattc     1260
tctttcattc cacaggttgc taattctctc tgttggtaat atcttttgat gctgttgtgt     1320
ccagaattga ttcattcctg tgggttcttg gtctcactga cttcaagaat aaagctgcgg     1380
accctagtgg tgagtgttac acttcttata gatggtgttt ccggagtttg ttccttcaga     1440
tgtgtccaga gtttcttcct tccaatgggt tcatggtctt gctgacttca ggaatgaagc     1500
cgcagaccct cgcagtgagg tttacagctc ttaaaggtgg cgtgtccaga gttgtttgtt     1560 cccctggtg ggttcgtggt cttgctgact tcaggaatga agccgcagac cctcgcagtg     1620
agtgttacag ctcataaagg tagtgcggac acagagtgag ctgcagcaag atttactgtg     1680
aagagcaaaa gaacaaagct tccacagcat agaaggacac cccagcgggt tcctgctgct     1740
ggctcaggtg gccagttatt attcccttat ttgccctgcc cacatcctgc tgattggtcc     1800
attttacaga gtactgattg gtccatttta cagagtgctg attggtgcat ttacaatcct     1860
ttagctagac acagagtgct gattgctgca ttcttacaga gtgctgattg gtgcatttac     1920
agtcctttag ctagatacag aacgctgatt gctgcgtttt ttacagagtg ctgattggtg     1980
catttacaat cctttagcta gacacagtgc tgattggtgg ttttttacag agtgctgatt     2040
ggtgcgtctt tacagagtgc tgattggtgc atttacaatc ctttagctag acacagagtg     2100
ctgattggtg cgtttataat cctctagcta gacagaaaag ttttccaagt ccccacctga     2160
ccgagaagcc ccactggctt cacctctcac tgttatactt tggacatttg tccccccaaa     2220
atctcatgtt gaaatgtaac ccctaatgtt ggaactgagg ccagactgga tgtggctggg     2280
ccatgggga                                                              2289

<210> SEQ ID NO 52
<211> LENGTH: 1184
<212> TYPE: DNA
<213> ORGANISM: Homo sapiens
<220> FEATURE:
<221> NAME/KEY: misc_feature
<223> OTHER INFORMATION: sequence of STAR52

<400> SEQUENCE: 52
ctcttctttg ttttttatt tgggtgtg tgggtacgtg taagatgaga aatgtacaaa       60
cacaagtatt tcagaaactc caagtaatat tctgtctgtg agttcacggt aaataaataa      120
aaagggcaaa gtgacagaaa tacaggatta ttaaaagcaa aataatgttc tttgaaatcc      180 ccccccttggt gtatttttta tcttaggatg cagcactttc agcatgccca agtattgaaa      240
gcagtgtttt tacgctacca cggtaatttt atttagaaac cccatgttca cttttagttt      300
taaaatggtc tttatgacat aaaattatca gcattcatat ttttgtgttt taatattcct      360
ttggctactt attgaaacag taaacattac gaaaattagt aaacaaatct tgatagttg       420
```

```
cttattttg tttaattgaa tgtttatttt attaggtaaa tatacaatca aatttattta      480
aaaataatga ggaaaagaat acttttcttt cgctttgcga aagcaaagtg attttcatt      540 cttctccgtc cgattccttc tcttccagct gccacagccg actgacaggc tcccggcggc      600
ctgaggagta gtatgcaaat tttggatgat tgacacctac agtagaagcc aatcacgtca      660
aagtaggatg ctgattggtt gacaacaata ggcgtaaacc ttgacgtttt aaaaacctga      720
cacccaatcc aggcgattca tgcaaataaa ggaagggagt cacattacca ggggccagag      780
agacttgagt acgacctcac gtgttcagtg gtggatattg cacagacgtc tgcaaggtct      840
atataaacgc tacataatgt tcaactcaat tgcttgcctt ggccttccc aaacttgtca       900 ctggaatata aattatccct tttttaaaaa taaaaaaata agaattatgt agtgcacata      960
tatgatggtt catgtagaaa tctaaatgga cttccaacgc atggaatttt cctatttccc     1020
cctttcttta aattaatcct cagtgaagga ggctgttttc ccctagattt caaaaggacg     1080
agatttacag agcctttcct tggagaaacc cgctctaggc acagatggtc agtaaattta     1140
gcttcttcag cgaagttcca catggcaccg ccagatggca taag                      1184

<210> SEQ ID NO 53
<211> LENGTH: 1431
<212> TYPE: DNA
<213> ORGANISM: Homo sapiens
<220> FEATURE:
<221> NAME/KEY: misc_feature
<223> OTHER INFORMATION: sequence of STAR53

<400> SEQUENCE: 53
ccctgaggaa gatgacgagt aactccgtaa gagaaccttc cactcatccc ccacatccct       60
gcagacgtgc tattctgtta tgatactggt atcccatctg tcacttgctc cccaaatcat      120
tcccttctta caattttcta ctgtacagca ttgaggctga acgatgagag atttcccatg      180
ctctttctac tccctgccct gtatatatcc ggggatcctc cctacccagg atgctgtggg      240
gtcccaaacc ccaagtaagc cctgatatgc gggccacacc tttctctagc ctaggaattg      300
ataacccagg cgaggaagtc actgtggcat gaacagatgg ttcacttcga ggaaccgtgg      360
aaggcgtgtg caggtcctga gatagggcag aatcggagtg tgcagggtct gcaggtcagg      420
aggagttgag attgcgttgc cacgtggtgg gaactcactg ccacttattt ccttctctct      480
tcttgcctca gcctcaggga tacgacacat gcccatgatg agaagcagaa cgtggtgacc      540
tttcacgaac atgggcatgg ctgcggaccc ctcgtcatca ggtgcatagc aagtgaaagc      600
aagtgttcac aacagtgaaa agttgagcgt catttttctt agtgtgccaa gagttcgatg      660
ttagcgttta cgttgtattt tcttacactg tgtcattctg ttagatacta acattttcat      720
tgatgagcaa gacatactta atgcatattt tggtttgtgt atccatgcac ctaccttaga      780
aaacaagtat tgtcggttac ctctgcatgg aacagcatta ccctcctctc tcccagatg      840 tgactactga gggcagttct gagtgtttaa tttcagattt tttcctctgc atttacacac      900
acacgcacac aaaccacacc acacacacac acacacacac acacacacac acacacacac      960
acacaccaag taccagtata agcatctgcc atctgctttt cccattgcca tgcgtcctgg     1020
tcaagctccc ctcactctgt ttcctggtca gcatgtactc ccctcatccg attccctgt     1080 agcagtcact gacagttaat aaacctttgc aaacgttccc cagttgtttg ctcgtgccat     1140
tattgtgcac acagctctgt gcacgtgtgt gcatatttct ttaggaaaga ttcttagaag     1200
tggaattgct gtgtcaaagg agtcatttat tcaacaaaac actaatgagt gcgtcctcgt     1260
```

```
gctgagcgct gttctaggtg ctggagcgac gtcagggaac aaggcagaca ggagttcctg   1320 accccgttc tagaggagga tgtttccagt tgttgggttt tgtttgtttg tttcttctag    1380
agatggtggt cttgctctgt ccaggctaga gtgcagtggc atgatcatag c            1431
```

<210> SEQ ID NO 54
<211> LENGTH: 975
<212> TYPE: DNA
<213> ORGANISM: Homo sapiens
<220> FEATURE:
<221> NAME/KEY: misc_feature
<223> OTHER INFORMATION: sequence of STAR54

<400> SEQUENCE: 54

```
ccataaaagt gtttctaaac tgcagaaaaa tcccctaca gtcttacagt tcaagaattt     60
tcagcatgaa atgcctggta gattacctga ctttttttgc caaaaataag gcacagcagc   120
tctctcctga ctctgacttt ctatagtcct tactgaatta tagtccttac tgaattcatt   180
cttcagtgtt gcagtctgaa ggacacccac attttctctt tgtctttgtc aattctttgt   240
gttgtaaggg caggatgttt aaaagttgaa gtcattgact tgcaaaatga gaaatttcag   300
agggcatttt gttctctaga ccatgtagct tagagcagtg ttcacactga ggttgctgct   360
aatgtttctg cagttcttac caatagtatc atttacccag caacaggata tgatagagga   420
cttcgaaaac cccagaaaat gttttgccat atatccaaag cccttgggaa atggaaagg    480 aattgcgggc tcccattttt atatatggat agatagagac caagaaagac caaggcaact   540
ccatgtgctt tacattaata aagtacaaaa tgttaacatg taggaagtct aggcgaagtt   600
tatgtgagaa ttctttacac taattttgca acattttaat gcaagtctga aattatgtca   660
aaataagtaa aaattttac aagttaagca gagaataaca atgattagtc agagaaataa    720
gtagcaaaat cttcttctca gtattgactt ggttgctttt caatctctga ggacacagca   780
gtcttcgctt ccaaatccac aagtcacatc agtgaggaga ctcagctgag actttggcta   840
atgttggggg gtccctcctg tgtctcccca ggcgcagtga gcctgcaggc cgacctcact   900
cgtggcacac aactaaatct gggagaagc aacccgatgc cagcatgatg cagatatctc    960
agggtatgat cggcc                                                    975
```

<210> SEQ ID NO 55
<211> LENGTH: 501
<212> TYPE: DNA
<213> ORGANISM: Homo sapiens
<220> FEATURE:
<221> NAME/KEY: misc_feature
<223> OTHER INFORMATION: sequence of STAR55

<400> SEQUENCE: 55

```
cctgaactca tgatccgccc acctcagcct cctgaagtgc tgggattaca ggtgtgagcc    60 accacccca gccgcaacac actcttgagc aaccatgtg tcataaaga aataaaatgg      120 aaatcagaaa gtatcttgag acagacaaaa atggaaacac aacataccaa aatttatggg   180
acacagcaaa agcagtttta ggagggaagt ttatagtgat gaataccctac ctcaaaatca   240 ttagcctgat tggatgacac tacagtgtat aaatgaattg aaaaccacat tgtgccccat    300
acatatatac aattttttatt tgttaattaa aaataaaata aactttaaa aagaagaaa    360 gagctcaaat aaacaaccta actttatacc tcaaggaaat agaagagcca gctaagccca   420
aagttgacag aaggaaaaaa atattggcag aaagaaatga aacagagact agaaagacaa   480
```

```
ttgaagagat cagcaaaact a                                              501
```

<210> SEQ ID NO 56
<211> LENGTH: 741
<212> TYPE: DNA
<213> ORGANISM: Homo sapiens
<220> FEATURE:
<221> NAME/KEY: misc_feature
<223> OTHER INFORMATION: sequence of STAR56

<400> SEQUENCE: 56

```
acacaggaaa agatcgcaat tgttcagcag agctttgaac cggggatgac ggtctccctc     60
gttgcccggc aacatggtgt agcagccagc cagttatttc tctggcgtaa gcaataccag    120
gaaggaagtc ttactgctgt cgccgccgga aacaggttg ttcctgcctc tgaacttgct     180
gccgccatga agcagattaa agaactccag cgcctgctcg gcaagaaaac gatgaaaat     240
gaactcctca agaagccgt tgaatatgga cgggcaaaaa agtggatagc gcacgcgccc     300
ttattgcccg gggatgggga gtaagcttag tcagccgttg tctccgggtg tcgcgtgcgc    360
agttgcacgt cattctcaga cgaaccgatg actggatgga tggccgccgc agtcgtcaca    420
ctgatgatac ggatgtgctt ctccgtatac accatgttat cggagagctg ccaacgtatg    480
gttatcgtcg ggtatgggcg ctgcttcgca gacaggcaga acttgatggt atgcctgcga    540
tcaatgccaa acgtgtttac cggatcatgc gccagaatgc gctgttgctt gagcgaaaac    600
ctgctgtacc gccatcgaaa cgggcacata caggcagagt ggccgtgaaa gaaagcaatc    660
agcgatggtg ctctgacggg ttcgagttct gctgtgataa cggagagaga ctgcgtgtca    720
cgttcgcgct ggactgctgt g                                              741
```

<210> SEQ ID NO 57
<211> LENGTH: 1365
<212> TYPE: DNA
<213> ORGANISM: Homo sapiens
<220> FEATURE:
<221> NAME/KEY: misc_feature
<223> OTHER INFORMATION: sequence of STAR57

<400> SEQUENCE: 57

```
tccttctgta aataggcaaa atgtattta gtttccacca cacatgttct tttctgtagg      60
gcttgtatgt tggaaatttt atccaattat tcaattaaca ctataccaac aatctgctaa    120
ttctggagat gtggcagtga ataaaaaagt tatagtttct gattttgtgg agcttggact    180
ttaatgatgg acaaaacaac acattcttaa atatatattt catcaaaatt atagtgggtg    240
aattatttat atgtgcattt acatgtgtat gtatacataa atgggcggtt actggctgca    300
ctgagaatgt acacgtggcg cgaacgaggc tgggcggtca gagaaggcct cccaaggagg    360
tggctttgaa gctgagtggt gcttccacgt gaaaaggctg gaaagggcat tccaagaaaa    420
ggctgaggcc agcgggaaag aggttccagt gcgctctggg aacggaaagc gcacctgcct    480
gaaacgaaaa tgagtgtgct gaaataggac gctagaaagg gaggcagagg ctggcaaaag    540
cgaccgagga ggagctcaaa ggagcgagcg gggaaggccg ctgtggagcc tggaggaagc    600
acttcggaag cgcttctgag cgggtaaggc cgctgggagc atgaactgct gagcaggtgt    660
gtccagaatt cgtgggttct tggtctcact gacttcaaga atgaagaggg accgcggacc    720
ctcgcggtga gtgttacagc tcttaaggtg gcgcgtctgg agtttgttcc ttctgatgtt    780
cggatgtgtt cagagtttct tccttctggt gggttcgtgg tctcgctggc tcaggagtga    840
agctgcagac cttcgcggtg agtgttacag ctcataaaag cagggtggac tcaaagagtg    900
```

```
agcagcagca agatttattg caaagaatga aagaacaaag cttccacact gtggaagggg      960
accccagcgg gttgccactg ctggctccgc agcctgcttt tattctctta tctggcccca     1020
cccacatcct gctgattggt agagccgaat ggtctgtttt gacggcgctg attggtgcgt     1080
ttacaatccc tgcgctagat acaaaggttc tccacgtccc caccagatta gctagataga     1140
gtctccacac aaaggttctc caaggcccca ccagagtagc tagatacaga gtgttgattg     1200
gtgcattcac aaaccctgag ctagacacag ggtgatgact ggtgtgttta caaaccttgc     1260
ggtagataca gagtatcaat tggcgtattt acaatcactg agctaggcat aaaggttctc     1320
caggtcccca ccagactcag gagcccagct ggcttcaccc agtgg                    1365
```

<210> SEQ ID NO 58
<211> LENGTH: 1401
<212> TYPE: DNA
<213> ORGANISM: Homo sapiens
<220> FEATURE:
<221> NAME/KEY: misc_feature
<223> OTHER INFORMATION: sequence of STAR58

<400> SEQUENCE: 58

```
aagtttacct tagccctaaa ttatttcatt gtgattggca ttttaggaaa tatgtattaa       60
ggaatgtctc ttaggagata aggataacat atgtctaaga aaattatatt gaaatattat      120
tacatgaact aaaatgttag aactgaaaaa aaattattgt aactccttcc agcgtaggca      180
ggagtatcta gataccaact ttaacaactc aactttaaca acttcgaacc aaccagatgg      240
ctaggagatt cacctattta gcatgatatc ttttattgat aaaaaaatat aaaacttcca      300
ttaaattttt aagctactac aatcctatta aatttaact taccagtgtt ctcaatgcta       360
cataatttaa aatcattgaa atcttctgat tttaactcct cagtcttgaa atctacttat      420
ttttagttac atatatatcc aatctactgc cgctagtaga agaagcttgg aatttgagaa      480
aaaaatcaga cgttttgtat attctcatat tcactaattt attttttaaa tgagtttctg      540
caatgcatca agcagtggca aaacaggaga aaaattaaaa ttggttgaaa agatatgtgt      600
gccaaacaat cccttgaaat tgatgaagt gactaatcct gagttattgt ttcaaatgtg       660
tacctgttta tacaagggta tcacctttga aatctcaaca ttaaatgaaa ttttataagc      720
aatttgttgt aacatgatta ttataaaatt ctgatataac attttttatt acctgtttag      780
agtttaaaga gagaaaagga gttaagaata attacatttt cattagcatt gtccgggtgc      840
aaaaacttct aacactatct tcaaatcttt ttctccattg ccttctgaac atacccactt      900
gggtatctca ttagcactgc aaattcaaca ttttcgattg ctaattttc tccctaaata       960 tttatttgtt ttctcagctt tagccaatgt ttcactattg accatttgct caagtatagt     1020
gacgcttcaa tgaccttcag agagctgttt cagtccttcc tggactactt gcatgcttcc     1080
aacaaaatga agcactcttg atgtcagtca ctcaaataaa tggaaatggg cccatttact     1140
aggaatgtta acagaataaa aagatagacg tgacaccagt tgcttcagtc catctccatt     1200
tacttgctta aggcctggcc atatttctca cagttgatat ggcgcagggc acatgtttaa     1260
atggctgttc ttgtaggatg gtttgactgt tggattcctc atcttccctc tccttaggaa     1320
ggaaggttac agtagtactg ttggctcctg gaatatagat tcataaagaa ctaatggagt     1380
atcatctccc actgctcttg t                                              1401
```

<210> SEQ ID NO 59
<211> LENGTH: 866

<212> TYPE: DNA
<213> ORGANISM: Homo sapiens
<220> FEATURE:
<221> NAME/KEY: misc_feature
<223> OTHER INFORMATION: sequence of STAR59

<400> SEQUENCE: 59

| | | | | | |
|---|---|---|---|---|---|
| gagatcacgc | cactgcactc | cagcctgggg | gacagagcaa | gactccatct | cagaaacaaa | 60 |
| caaacacaca | aagccagtca | aggtgtttaa | ttcgacggtg | tcaggctcag | gtctcttgac | 120 |
| aggatacatc | cagcacccgg | gggaaacgtc | gatgggtggg | gtggaatcta | ttttgtggcc | 180 |
| tcaagggagg | gtttgagagg | tagtcccgca | agcggtgatg | gcctaaggaa | gcccctccgc | 240 |
| ccaagaagcg | atattcattt | ctagcctgta | gccacccaag | agggagaatc | gggctcgcca | 300 |
| cagaccccac | aaccccaac | ccaccccacc | cccaccctc | ccacctcgtg | aaatgggctc | 360 |
| tcgctccgtc | aggctctagt | cacaccgtgt | ggttttggaa | cctccagcgt | gtgtgcgtgg | 420 |
| gttgcgtggt | ggggtggggc | cggctgtgga | cagaggaggg | gataaagcgg | cggtgtcccg | 480 |
| cgggtgcccg | ggacgtgggg | cgtggggcgt | gggtggggtg | gccagagcct | tgggaactcg | 540 |
| tcgcctgtcg | ggacgtctcc | cctcctggtc | ccctctctga | cctacgctcc | acatcttcgc | 600 |
| cgttcagtgg | ggaccttgtg | ggtggaagtc | accatccctt | tggactttag | ccgacgaagg | 660 |
| ccgggctccc | aagagtctcc | ccggaggcgg | ggccttgggc | aggctcacaa | ggatgctgac | 720 |
| ggtgacggtt | ggtgacggtg | atgtacttcg | gaggcctcgg | gccaatgcag | aggtatccat | 780 |
| ttgacctcgg | tgggacaggt | cagctttgcg | gagtcccgtg | cgtccttcca | gagactcatc | 840 |
| cagcgctagc | aagcatggtc | ccgagg | | | | 866 |

<210> SEQ ID NO 60
<211> LENGTH: 2067
<212> TYPE: DNA
<213> ORGANISM: Homo sapiens
<220> FEATURE:
<221> NAME/KEY: misc_feature
<223> OTHER INFORMATION: sequence of STAR60
<220> FEATURE:
<221> NAME/KEY: misc_feature
<222> LOCATION: (92)..(92)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (344)..(345)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (902)..(902)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:

<221> NAME/KEY: misc_feature
<222> LOCATION: (924)..(924)
<223> OTHER INFORMATION: n is a, c, g, or t
<220> FEATURE:
<221> NAME/KEY: misc_feature
<222> LOCATION: (1522)..(1522)
<223> OTHER INFORMATION: n is a, c, g, or t
<220> FEATURE:
<221> NAME/KEY: misc_feature
<222> LOCATION: (1590)..(1590)
<223> OTHER INFORMATION: n is a, c, g, or t
<220> FEATURE:
<221> NAME/KEY: misc_feature
<222> LOCATION: (1601)..(1601)
<223> OTHER INFORMATION: n is a, c, g, or t
<220> FEATURE:
<221> NAME/KEY: misc_feature
<222> LOCATION: (1647)..(1647)
<223> OTHER INFORMATION: n is a, c, g, or t
<220> FEATURE:
<221> NAME/KEY: misc_feature
<222> LOCATION: (1677)..(1677)
<223> OTHER INFORMATION: n is a, c, g, or t
<220> FEATURE:
<221> NAME/KEY: misc_feature
<222> LOCATION: (1777)..(1777)
<223> OTHER INFORMATION: n is a, c, g, or t

<400> SEQUENCE: 60

```
agcagtgcag aactggggaa gaagaagagt ccctacacca cttaatactc aaaagtactc      60
gcaaaaaata acaccoctca ccaggtggca tnattactct ccttcattga gaaaattagg     120
aaactggact tcgtagaagc taattgcttt atccagagcc acctgcatac aaacctgcag     180
cgccacctgc atacaaacct gtcagccgac cccaaagccc tcagtcgcac caagcctctg     240
ctgcacaccc tcgtgccttc acactggccg ttccccaagc tggggcata  ctncccagct     300
ctgagaaatg tattcatcct tcaaagcccc gctcatgtgt cctnntcaac aggaaaatct     360
cccatgagat gctctgctat ccccatctct cctgccccat agcttaggca nacttctgtg     420
gtggtgagtc ctgggctgtg ctgtgatgtg ttcgcctgcn atgtntgttc ttccccacaa     480
tgatgggccc ctgaattctc tatctctagc acctgtgctc agtaaaggct tgggaaacca     540
ggctcaaagc ctggcccaga tgccacctt  tccagggtgc ttccggggggc caccaaccag     600
agtgcagcct tctcctccac caggaactct tgcagcccca cccctgagca cctgcacccc     660
attacccatc tttgtttctc cgtgtgatcg tattattaca gaattatata ctgtattctt     720
aatacagtat ataattgtat aattattctt aatacagtat ataattatac aaatacaaaa     780
tatgtgttaa tggaccgttt atgttactgg taaagcttta agtcaacagt gggacattag     840
ttaggttttt ggcgaagtca aaagttatat gtgcattttc aacttcttga ggggtcggta     900
cntctnaccc ccatgttgtt caanggtcaa ctgtctacac atatcatagc taattcacta     960
cagaaatgtt agcttgtgtc actagtatct ccccttctca taagcttaat acacatacct    1020
tgagagagct cttggccatc tctactaatg actgaagttt ttatttatta tagatgtcat    1080
aataggcata aaactacatt acatcattcg agtgccaatt ttgccaccctt gaccctcttt    1140
tgcaaaacac caacgtcagt acacatatga agaggaaact gcccgagaac tgaagttcct    1200
gagaccagga gctgcaggcg ttagatagaa tatggtgacg agagttacga ggatgacgag    1260
agtaaatact tcatactcag tacgtgccaa gcactgctat aagcgctctg tatgtgtgaa    1320
gtcatttaat cctcacagca tcccacggtg taattatttt cattatcccc atgagggaac    1380
agaaactcag aacggttcaa cacatatgcg agaagtcgca gccggtcagt gagagagcag    1440
gttcccgtcc aagcagtcag accccgagtg cacactctcg accctgtcc  agcagactca    1500
```

```
ctcgtcataa ggcggggagt gntctgtttc agccagatgc tttatgcatc tcagagtacc    1560
caaaccatga aagaatgagg cagtattcan gagcagatgg ngctgggcag taaggctggg    1620
cttcagaata gctggaaagc tcaagtnatg ggacctgcaa gaaaaatcca ttgtttngat    1680
aaatagccaa agtccctagg ctgtaagggg aaggtgtgcc aggtgcaagt ggagctctaa    1740
tgtaaaatcg cacctgagtc tcctggtctt atgagtnctg ggtgtacccc agtgaaaggt    1800
cctgctgcca ccaagtgggc catggttcag ctgtgtaagt gctgagcggc agccggaccg    1860
cttcctctaa cttcacctcc aaaggcacag tgcacctggt tcctccagca ctcagctgcg    1920
aggcccctag ccagggtccc ggcccccggc cccggcagc tgctccagct tccttcccca    1980
cagcattcag gatggtctgc gttcatgtag acctttgttt tcagtctgtg ctccgaggtc    2040
actggcagca ctagccccgg ctcctgt                                       2067

<210> SEQ ID NO 61
<211> LENGTH: 1470
<212> TYPE: DNA
<213> ORGANISM: Homo sapiens
<220> FEATURE:
<221> NAME/KEY: misc_feature
<223> OTHER INFORMATION: sequence of STAR61
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (963)..(963)
<223> OTHER INFORMATION: n is a, c, g, or t
<220> FEATURE:
<221> NAME/KEY: misc_feature
<222> LOCATION: (976)..(976)
<223> OTHER INFORMATION: n is a, c, g, or t

<400> SEQUENCE: 61
cagcccccac atgcccagcc ctgtgctcag ctctgcagcg gggcatggtg ggcagagaca      60
cagaggccaa ggccctgctt cggggacggt gggcctggga tgagcatggc cttggccttc     120
gccgagagtn ctcttgtgaa ggagggggtca ggaggggctg ctgcagctgg ggaggagggc    180
gatggcactg tggcangaag tgaantagtg tgggtgcctn gcaccccagg cacggccagc     240
ctggggtatg gacccggggc cntctgttct agagcaggaa ggtatggtga ggacctcaaa    300
aggacagcca ctggagagct ccaggcagag gnacttgaga ggccctgggg ccatcctgtc    360
```

```
tcttttctgg gtctgtgtgc tctgggcctg ggcccttcct ctgctccccc gggcttggag      420
agggctggcc ttgcctcgtg caaaggacca ctctagactg gtaccaagtc tggcccatgg      480
cctcctgtgg gtgcaggcct gtgcgggtga cctgagagcc agggctggca ggtcagagtc      540
aggagaggga tggcagtgga tgccctgtgc aggatctgcc taatcatggt gaggctggag      600
gaatccaaag tgggcatgca ctctgcactc atttctttat tcatgtgtgc ccatcccaac      660
aagcagggag cctggccagg agggcccctg ggagaaggca ctgatgggct gtgttccatt      720
taggaaggat ggacggttgt gagacgggta agtcagaacg ggctgcccac ctcggccgag      780
agggccccgt ggtgggttgg caccatctgg gcctggagag ctgctcagga ggctctctag      840
ggctgggtga ccaggnctgg ggtacagtag ccatgggagc aggtgcttac ctggggctgt      900
ccctgagcag gggctgcatt gggtgctctg tgagcacaca cttctctatt cacctgagtc      960
ccnctgagtg atgagnacac ccttgttttg cagatgaatc tgagcatgga gatgttaagt     1020
ggcttgcctg agccacacag cagatggatg gtgtagctgg gacctgaggg caggcagtcc     1080
cagcccgagg acttcccaag gttgtggcaa actctgacag catgacccca gggaacaccc     1140
atctcagctc tggtcagaca ctgcggagtt gtgttgtaac ccacacagct ggagacagcc     1200
accctagccc cacccttatc ctctcccaaa ggaacctgcc ctttcccttc attttcctct     1260
tactgcattg agggaccaca cagtgtggca gaaggaacat gggttcagga cccagatgga     1320
cttgcttcac agtgcagccc tcctgtcctc ttgcagagtg cgtcttccac tgtgaagttg     1380
ggacagtcac accaactcaa tactgctggg cccgtcacac ggtgggcagg caacggatgg     1440
cagtcactgg ctgtgggtct gcagaggtgg                                      1470

<210> SEQ ID NO 62
<211> LENGTH: 1011
<212> TYPE: DNA
<213> ORGANISM: Homo sapiens
<220> FEATURE:
<221> NAME/KEY: misc_feature
<223> OTHER INFORMATION: sequence of STAR62

<400> SEQUENCE: 62
agtgtcaaat agatctacac aaaacaagat aatgtctgcc cattttttcca aagataatgt      60 ggtgaagtgg gtagagagaa atgcatccat tctccccacc caacctctgc taaattgtcc     120
atgtcacagt actgagacca gggggcttat tcccagcggg cagaatgtgc accaagcacc     180
tcttgtctca atttgcagtc taggccctgc tatttgatgg tgtgaaggct tgcacctggc     240
atggaaggtc cgttttgtac ttcttgcttt agcagttcaa agagcaggga gagctgcgag     300
ggcctctgca gcttcagatg gatgtggtca gcttgttgga ggcgccttct gtggtccatt     360
atctccagcc cccctgcggt gttgctgttt gcttggcttg tctggctctc catgccttgt     420
tggctccaaa atgtcatcat gctgcacccc aggaagaatg tgcaggccca tctcttttat     480
gtgctttggg ctattttgat tccccgttgg gtatattccc taggtaagac ccagaagaca     540
caggaggtag ttgctttggg agagtttgga cctatgggta tgaggtaata gacacagtat     600
cttctctttc atttggtgag actgttagct ctggccgcgg actgaattcc acacagctca     660
cttgggaaaa ctttattcca aaacatagtc acattgaaca ttgtggagaa tgagggacag     720
agaagaggcc ctagatttgt acatctgggt gttatgtcta taaatagaat gctttggtgg     780
tcaactagac ttgttcatgt tgacatttag tcttgccttt tcgtggtgta tttaaaaatt     840
atgtatatct tgtttggaat atagtggagc tatggtgtgg cattttcatc tggcttttg     900
```

```
tttagctcag cccgtcctgt tatgggcagc cttgaagctc agtagctaat gaagaggtat    960
cctcactccc tccagagagc ggtcccctca cggctcattg agagtttgtc a           1011
```

<210> SEQ ID NO 63
<211> LENGTH: 1410
<212> TYPE: DNA
<213> ORGANISM: Homo sapiens
<220> FEATURE:
<221> NAME/KEY: misc_feature
<223> OTHER INFORMATION: sequence of STAR63

<400> SEQUENCE: 63

```
ccacagcctg atcgtgctgt cgatgagagg aatctgctct aagggtctga gcggagggag     60
atgccgaagc tttgagcttt ttgtttctgg cttaaccttg gtggattttc accctctggg    120
cattacctct tgtccagggg aggggctggg ggagtgcctg gagctgtagg gacagagggc    180
tgagtggggg ggactgcttg ggctgaccac ataatattct gctgcgtatt aatttttttt    240
tgagacagtc tttctctgtt gcccaggctg gagtgtaatg gcttgatagc tcactgccac    300
ctccgcctcc tgggttcaag tgattctcct gcttcagctt ccggagtagc tgggactgca    360
ggtgcccgcc accatggctg gctaatttt gtatttttat tagcaatggg gttttgctat    420
gttgcccagg ccgtcccga actcctgccc tcaagtgata cacctgcctc ggcctcccaa    480
agtgctggga ttagaggctt gagccactgc gcctggccag ctgcatattg ttaattagac    540
ataaaatgca aaataagatg atataaacac aaaggtgtga aataagatgg acacctgctg    600
agcgcgcctg tcctgaagca tcgcccctct gcaaaagcag gggtcagcat gtgttctccg    660
gtccttgctc ttacagagga gtgagctgcc tatgcgtctt ccagccactt cctgggctgc    720
tcagaggcct ctcacgggtg ttctgggttg ctgccacttg caggggtgct gaggcggggc    780
tcctcccgtg cggggcatgt ccaggccgcc ctctctgaag gcttggcagg tacaggtggg    840
agtgggggtc tctgggctgc tgtggggact gggcaggctc ctggaagacc tccctgtgtt    900
tgggctgaaa gcgcagcccg aggggaggtc cccaggagg ccgctgtcgg gggtgggggc    960
ttggaggagg gaggggccga ggagccggcg acactccgtg acggcccagg aacgtcccta   1020
aacaaggcgc cgcgttctcg atggggtggg gtccgctttc ttttctcaaa agctgcagtt   1080
actccatgct cggaggactg gcgtccgcgc cctgttccaa tgctgccccg gggccctggc   1140
cttggggaat cggggccttg gactggaccc tgggggcttc gcggagccgg gcctggcggg   1200
gcgagcggag cagaggctgg gcagccccgg ggaagcgctc gccaaagccg ggcgctgctc   1260
ccagagcgcg aggtgcagaa ccagaggctg gtcccgcggc gctaacgaga gaagaggaag   1320
cgcgctgtgt agagggcgcc caccccgtgg ggcgaacccc cttcctcaac tccatggacg   1380
gggctcatgg gttcccagcg gctcagacgc                                    1410
```

<210> SEQ ID NO 64
<211> LENGTH: 1414
<212> TYPE: DNA
<213> ORGANISM: Homo sapiens
<220> FEATURE:
<221> NAME/KEY: misc_feature
<223> OTHER INFORMATION: sequence of STAR64

<400> SEQUENCE: 64

```
tggatcagat ttgttttata ccctcccttc tactgctctg agagttgtac atcacagtct     60
actgtatctg tttcccatta ttataatttt tttgcactgt gcttgcctga agggagcctc    120
```

| | |
|---|---|
| aagttcatga gtctccctac cctcctccca aatgagacat ggacctttga atgctttcct | 180 |
| gggaccacca ccccaccttt catgctgctg ttatccagga ttttagttca acagtgtttt | 240 |
| aaccccccaa atgagtcatt tttattgttt cgtatagtga atgtgtattt gggtttgctt | 300 |
| atatggtgac ctgtttattt gctcctcatt gtacctcatg ctctgctctt tccttctaga | 360 |
| ttcagtctct ttcctaatga ggtgtctcgc agcaattctt tacaagacag ccaagatagg | 420 |
| ccagctctca gagcacttgt tgtctgaaaa agtcttgtct tatttaattt cttttttctta | 480 |
| gagatggggt ctcattatgt tacccacact ggtctcaaac ttctggctta aagcggtcct | 540 |
| cccaccttgg cctcccaaag tgctaggatt acaggcgtga gcgacctcgt ccagcctgtc | 600 |
| tgagaaagcg tttgttttgc ccttgctctc agatgacagt ttggggatag aattctaggt | 660 |
| ggacggtttt tttccttcag ccctttgaag agtctgtatt ttcattatct ccctgcatta | 720 |
| gatgttcttt tgcaagtaac gtgtcttttc tctctgggta ttcttaaggt tttctctttg | 780 |
| cctttggtga gctgcagtgg atttgctttt ttcaagaggt caagagaaag gaaagtgtga | 840 |
| ggtttctgtt ttttactgac aatttgtttg ttgatttgtt ttcccaccca gaggttcctt | 900 |
| gccactttgc caggctggaa ggcagacttc ttctggtgtc ctgttcacag acggggcagc | 960 |
| ctgcggaagg ccctgccaca tgcagggcct cggtcctcat tcccttgcat gtggacccgg | 1020 |
| gcgtgactcc tgttcaggct ggcacttccc agagctgagc cccagcctga ccttcctccc | 1080 |
| atactgtctt cacaccccct cctttcttct gatacctgga ggttttcctt tctttcctgt | 1140 |
| cacctccact tggattttaa atcctctgtc tgtggaattg tattcggcac aggaagatgc | 1200 |
| ttgcaagggc caggctcatc agccctgtcc ctgctgctgg aagcagcaca gcagagcctc | 1260 |
| atgctcaggc tgagatggag cagaggcctg cagacgagca cccagctcag ctggggttgg | 1320 |
| cgccgatggt ggagggtcct cgaaagctct ggggacgatg gcagagctat tggcagggga | 1380 |
| gccgcagggt cttttgagcc cttaaaagat ctct | 1414 |

<210> SEQ ID NO 65
<211> LENGTH: 1310
<212> TYPE: DNA
<213> ORGANISM: Homo sapiens
<220> FEATURE:
<221> NAME/KEY: misc_feature
<223> OTHER INFORMATION: sequence of STAR65

<400> SEQUENCE: 65

| | |
|---|---|
| gtgaatgttg atggatcaaa tatctttctg tgttgtttat caaagttaaa ataaatgtgg | 60 |
| tcatttaaag gacaaaagat gaggggttgg agtctgttca agcaagggt atattaggag | 120 |
| aaaagcagaa ttctctccct gtgaagggac agtgactcct attttccacc tcatttttac | 180 |
| taactctcct aactatctgc ttaggtagag atatatccat gtacatttat aaaccacagt | 240 |
| gaatcatttg attttggaat aaagatagta taaaatgtgt cccagtgttg atatacatca | 300 |
| tacattaaat atgtctggca gtgttctaat tttacagttg tccaaagata atgttagggc | 360 |
| atactggcta tggatgaagc tccaatgttc agattgcaaa gaaacttaga attttactaa | 420 |
| tgaaaccaaa tacatcccaa gaaatttttc agaagaaaaa aagagaaact agtagcaaag | 480 |
| taaagaatca ccacaatatc atcagatttt ttttatatgt agaatattta ttcagttctt | 540 |
| ttttcaagta cacctgtctt tcattcattg tactttattt tttgtgaagg tttaaattta | 600 |
| tttcttctat gtgtttagtg atatttaaaa ttttatttta atcaagttta tcagaaagtt | 660 |
| ctgttagaaa atatgacgag gctttaattc cgccatctat atttttccgct attatataaa | 720 |

```
gataattgtt ttctctttt aaaacaactt gaattgggat tttatatcat aatttttaa        780 tgtctttttt tattatactt taagttctgg gatacatgtg cagaacgtgc aggtgtgtta       840
catagatata cacgtgccat ggtggtttgc tgcacccact aacctgttat cgacattagg       900
tatttctcct aatgctatca cccctattt ccccacccc cgagaggccc cagtgtgtga         960
tgttctcctc cctgtgtcca tgtgttctca ttgttcatct cccacttatg gtatctacca      1020
taaccttgaa attgtcttat gcattcactt gtttggttgt tatatagcct ccatcaggac      1080
agggatattt gctgctgctt cttttttttt tcttttgag acagtcttgc tccgtcatcc      1140
aggctggagt gcttctcggc tcaatgcaac ctccacctcc caggtttaag cgattctcca     1200
acttcagcct cccaaatggc tgggactgca ggcatgcacc actacacctg gctaattttt    1260
gtatttgtaa tagagacaat gtttcaccat gttggccagg ctggtctcga                1310
```

<210> SEQ ID NO 66
<211> LENGTH: 1917
<212> TYPE: DNA
<213> ORGANISM: Homo sapiens
<220> FEATURE:
<221> NAME/KEY: misc_feature
<223> OTHER INFORMATION: sequence of STAR67

<400> SEQUENCE: 66

```
aggatcctaa aattttgtga ccctagagca agtactaact atgaaagtga aatagagaat        60
gaaggaatta tttaattaag tccagcaaaa cccaaccaaa tcatctgtaa aatatatttg       120
ttttcaacat ccaggtattt tctgtgtaaa aggttgagtt gtatgctgac ttattgggaa       180
aaataattga gttttcccct tcactttgcc agtgagagga aatcagtact gtaattgtta       240
aaggttaccc atacctacct ctactaccgt ctagcatagg taaagtaatg tacactgtga       300
agtttcctgc ttgactgtaa tgttttcagt ttcatcccat tgattcaaca gctatttatt       360
cagcacttac tacaaccatg ctggaaaccc aagagtaaat aggctgtgtt actcaacagg       420
actgaggtac agccgaactg tcaggcaagg ttgctgtcct ttggacttgc ctgctttctc       480
tctatgtagg aagaagaaat ggacataccg tccaggaaat agatatatgt tacatttcct       540
tattccataa ttaatattaa taaccctgga cagaaactac caagtttcta gacccttata       600
gtaccacctt acccttctg gatgaatcct tcacatgttg atacatttta tccaaatgaa       660
aattttggta ctgtaggtat aacagacaaa gagagaacag aaaactagag atgaagtttg       720
ggaaaaggtc aagaaagtaa ataatgcttc tagaagacac aaaagaaaa atgaaatggt       780 aatgttggga aagttttaat acattttgcc ctaaggaaaa aaactacttg ttgaaaattct      840 acttaagact ggacctttc tctaaaaatt gtgcttgatg tgaattaaag caacacaggg       900
aaatttatgg gctccttcta agttctaccc aactcaccgc aaaactgttc ctagtaggtg      960
tggtatactc tttcagattc tttgtgtgta tgtatatgtg tgtgtgtgtg tgtgtttgta      1020
tgtgtacagt ctatatacat atgtgtacct acatgtgtgt atatataaat atatatttac      1080
ctggatgaaa tagcatatta tagaatattc ttttttcttt aaatatatat gtgcatacat      1140
atgtatatgc acatatatac ataaatgtag atatagctag gtaggcattc atgtgaaaca      1200
aagaagccta ttacttttta atggttgcat gatattccat cataggagta tagtacaact      1260
tatgtaacac acatttggct tgttgtaaaa ttttggtatt aataaaatag cacatatcat      1320
gcaaagacac ccttgcatag gtctattcat tctttgattt ttaccttagg acaaaattta      1380
aaagtagaat ttctgggtca agcagtatgc tcatttaaaa tgtcattgca tatttccaaa      1440
```

```
ttgtcctcca gaaaagtagt aacagtaaca attgatggac tgcgtgtttt ctaaaacttg   1500 cattttttc  cttattggtg aggtttggca ttttccatat gtttattggc attttaattt   1560
tttttggttc atgtctttta ttccttcct  gcaaatttgt ggtgtgtctc aactttattt   1620
atactctcat tttcataatt ttctaaagga atttgacttt aaaaaaataa gacagccaat   1680
gctttggttt aatttcattg ctgcttttg  aagtgactgc tgtgttttta tactttta    1740 tattttgttg ttttagcaaa ttcttctata ttataattgt gtatgctgga acaaaaagtt   1800
atatttctta atctagataa aatatttcaa gatgttgtaa ttacagtccc ctctaaaatc   1860
atataaatag acgcatagct gtgtgatttg taattagtta tgtccattga tagatcc      1917
```

```
<210> SEQ ID NO 67
<211> LENGTH: 375
<212> TYPE: DNA
<213> ORGANISM: Artificial
<220> FEATURE:
<223> OTHER INFORMATION: wt zeocin resistance gene
<220> FEATURE:
<221> NAME/KEY: CDS
<222> LOCATION: (1)..(375)

<400> SEQUENCE: 67 atg gcc aag ttg acc agt gcc gtt ccg gtg ctc acc gcg cgc gac gtc    48
Met Ala Lys Leu Thr Ser Ala Val Pro Val Leu Thr Ala Arg Asp Val
1               5                   10                  15 gcc gga gcg gtc gag ttc tgg acc gac cgg ctc ggg ttc tcc cgg gac    96
Ala Gly Ala Val Glu Phe Trp Thr Asp Arg Leu Gly Phe Ser Arg Asp
                20                  25                  30 ttc gtg gag gac gac ttc gcc ggt gtg gtc cgg gac gac gtg acc ctg   144
Phe Val Glu Asp Asp Phe Ala Gly Val Val Arg Asp Asp Val Thr Leu
            35                  40                  45 ttc atc agc gcg gtc cag gac cag gtg gtg ccg gac aac acc ctg gcc   192
Phe Ile Ser Ala Val Gln Asp Gln Val Val Pro Asp Asn Thr Leu Ala
        50                  55                  60 tgg gtg tgg gtg cgc ggc ctg gac gag ctg tac gcc gag tgg tcg gag   240
Trp Val Trp Val Arg Gly Leu Asp Glu Leu Tyr Ala Glu Trp Ser Glu
65                  70                  75                  80 gtc gtg tcc acg aac ttc cgg gac gcc tcc ggg ccg gcc atg acc gag   288
Val Val Ser Thr Asn Phe Arg Asp Ala Ser Gly Pro Ala Met Thr Glu
                85                  90                  95 atc ggc gag cag ccg tgg ggg cgg gag ttc gcc ctg cgc gac ccg gcc   336
Ile Gly Glu Gln Pro Trp Gly Arg Glu Phe Ala Leu Arg Asp Pro Ala
                100                 105                 110 ggc aac tgc gtg cac ttc gtg gcc gag gag cag gac tga               375
Gly Asn Cys Val His Phe Val Ala Glu Glu Gln Asp
            115                 120
```

```
<210> SEQ ID NO 68
<211> LENGTH: 124
<212> TYPE: PRT
<213> ORGANISM: Artificial
<220> FEATURE:
<223> OTHER INFORMATION: Synthetic Construct

<400> SEQUENCE: 68

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
                20                  25                  30

Phe Val Glu Asp Asp Phe Ala Gly Val Val Arg Asp Asp Val Thr Leu
            35                  40                  45
```

```
Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
 65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
            115                 120
```

<210> SEQ ID NO 69
<211> LENGTH: 399
<212> TYPE: DNA
<213> ORGANISM: Artificial
<220> FEATURE:
<223> OTHER INFORMATION: wt blasticidin resistance gene
<220> FEATURE:
<221> NAME/KEY: CDS
<222> LOCATION: (1)..(399)

<400> SEQUENCE: 69

```
atg gcc aag cct ttg tct caa gaa gaa tcc acc ctc att gaa aga gca      48
Met Ala Lys Pro Leu Ser Gln Glu Glu Ser Thr Leu Ile Glu Arg Ala
 1               5                  10                  15 acg gct aca atc aac agc atc ccc atc tct gaa gac tac agc gtc gcc      96
Thr Ala Thr Ile Asn Ser Ile Pro Ile Ser Glu Asp Tyr Ser Val Ala
                20                  25                  30 agc gca gct ctc tct agc gac ggc cgc atc ttc act ggt gtc aat gta     144
Ser Ala Ala Leu Ser Ser Asp Gly Arg Ile Phe Thr Gly Val Asn Val
            35                  40                  45 tat cat ttt act ggg gga cct tgt gca gaa ctc gtg gtg ctg ggc act     192
Tyr His Phe Thr Gly Gly Pro Cys Ala Glu Leu Val Val Leu Gly Thr
    50                  55                  60 gct gct gct gcg gca gct ggc aac ctg act tgt atc gtc gcg atc gga     240
Ala Ala Ala Ala Ala Ala Gly Asn Leu Thr Cys Ile Val Ala Ile Gly
 65                  70                  75                  80 aat gag aac agg ggc atc ttg agc ccc tgc gga cgg tgc cga cag gtg     288
Asn Glu Asn Arg Gly Ile Leu Ser Pro Cys Gly Arg Cys Arg Gln Val
                85                  90                  95 ctt ctc gat ctg cat cct ggg atc aaa gcc ata gtg aag gac agt gat     336
Leu Leu Asp Leu His Pro Gly Ile Lys Ala Ile Val Lys Asp Ser Asp
            100                 105                 110 gga cag ccg acg gca gtt ggg att cgt gaa ttg ctg ccc tct ggt tat     384
Gly Gln Pro Thr Ala Val Gly Ile Arg Glu Leu Leu Pro Ser Gly Tyr
            115                 120                 125 gtg tgg gag ggc taa                                                 399
Val Trp Glu Gly
    130
```

<210> SEQ ID NO 70
<211> LENGTH: 132
<212> TYPE: PRT
<213> ORGANISM: Artificial
<220> FEATURE:
<223> OTHER INFORMATION: Synthetic Construct

<400> SEQUENCE: 70

```
Met Ala Lys Pro Leu Ser Gln Glu Glu Ser Thr Leu Ile Glu Arg Ala
 1               5                  10                  15

Thr Ala Thr Ile Asn Ser Ile Pro Ile Ser Glu Asp Tyr Ser Val Ala
```

```
                    20                  25                  30
Ser Ala Ala Leu Ser Ser Asp Gly Arg Ile Phe Thr Gly Val Asn Val
            35                  40                  45

Tyr His Phe Thr Gly Gly Pro Cys Ala Glu Leu Val Val Leu Gly Thr
    50                  55                  60

Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95

Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly
        130

<210> SEQ ID NO 71
<211> LENGTH: 600
<212> TYPE: DNA
<213> ORGANISM: Artificial
<220> FEATURE:
<223> OTHER INFORMATION: wt puromycin resistance gene
<220> FEATURE:
<221> NAME/KEY: CDS
<222> LOCATION: (1)..(600)

<400> SEQUENCE: 71
```

| | | | | | | | | | | | | | | | | |
|---|---|---|---|---|---|---|---|---|---|---|---|---|---|---|---|---|
| atg | acc | gag | tac | aag | ccc | acg | gtg | cgc | ctc | gcc | acc | cgc | gac | gac | gtc | 48 |
| Met | Thr | Glu | Tyr | Lys | Pro | Thr | Val | Arg | Leu | Ala | Thr | Arg | Asp | Asp | Val | |
| 1 | | | | 5 | | | | | 10 | | | | | 15 | | |
| ccc | agg | gcc | gta | cgc | acc | ctc | gcc | gcc | gcg | ttc | gcc | gac | tac | ccc | gcc | 96 |
| Pro | Arg | Ala | Val | Arg | Thr | Leu | Ala | Ala | Ala | Phe | Ala | Asp | Tyr | Pro | Ala | |
| | | | 20 | | | | | 25 | | | | | 30 | | | |
| acg | cgc | cac | acc | gtc | gat | ccg | gac | cgc | cac | atc | gag | cgg | gtc | acc | gag | 144 |
| Thr | Arg | His | Thr | Val | Asp | Pro | Asp | Arg | His | Ile | Glu | Arg | Val | Thr | Glu | |
| | 35 | | | | | 40 | | | | | 45 | | | | | |
| ctg | caa | gaa | ctc | ttc | ctc | acg | cgc | gtc | ggg | ctc | gac | atc | ggc | aag | gtg | 192 |
| Leu | Gln | Glu | Leu | Phe | Leu | Thr | Arg | Val | Gly | Leu | Asp | Ile | Gly | Lys | Val | |
| | 50 | | | | 55 | | | | | 60 | | | | | | |
| tgg | gtc | gcg | gac | gac | ggc | gcc | gcg | gtg | gcg | gtc | tgg | acc | acg | ccg | gag | 240 |
| Trp | Val | Ala | Asp | Asp | Gly | Ala | Ala | Val | Ala | Val | Trp | Thr | Thr | Pro | Glu | |
| 65 | | | | 70 | | | | | 75 | | | | | 80 | | |
| agc | gtc | gaa | gcg | ggg | gcg | gtg | ttc | gcc | gag | atc | ggc | ccg | cgc | atg | gcc | 288 |
| Ser | Val | Glu | Ala | Gly | Ala | Val | Phe | Ala | Glu | Ile | Gly | Pro | Arg | Met | Ala | |
| | | | | 85 | | | | | 90 | | | | | 95 | | |
| gag | ttg | agc | ggt | tcc | cgg | ctg | gcc | gcg | cag | caa | cag | atg | gaa | ggc | ctc | 336 |
| Glu | Leu | Ser | Gly | Ser | Arg | Leu | Ala | Ala | Gln | Gln | Gln | Met | Glu | Gly | Leu | |
| | | | 100 | | | | | 105 | | | | | 110 | | | |
| ctg | gcg | ccg | cac | cgg | ccc | aag | gag | ccc | gcg | tgg | ttc | ctg | gcc | acc | gtc | 384 |
| Leu | Ala | Pro | His | Arg | Pro | Lys | Glu | Pro | Ala | Trp | Phe | Leu | Ala | Thr | Val | |
| | | 115 | | | | | 120 | | | | | 125 | | | | |
| ggc | gtc | tcg | ccc | gac | cac | cag | ggc | aag | ggt | ctg | ggc | agc | gcc | gtc | gtg | 432 |
| Gly | Val | Ser | Pro | Asp | His | Gln | Gly | Lys | Gly | Leu | Gly | Ser | Ala | Val | Val | |
| | 130 | | | | | 135 | | | | | 140 | | | | | |
| ctc | ccc | gga | gtg | gag | gcg | gcc | gag | cgc | gcc | ggg | gtg | ccc | gcc | ttc | ctg | 480 |
| Leu | Pro | Gly | Val | Glu | Ala | Ala | Glu | Arg | Ala | Gly | Val | Pro | Ala | Phe | Leu | |
| 145 | | | | 150 | | | | | 155 | | | | | 160 | | |
| gag | acc | tcc | gcg | ccc | cgc | aac | ctc | ccc | ttc | tac | gag | cgg | ctc | ggc | ttc | 528 |
| Glu | Thr | Ser | Ala | Pro | Arg | Asn | Leu | Pro | Phe | Tyr | Glu | Arg | Leu | Gly | Phe | |
| | | | | 165 | | | | | 170 | | | | | 175 | | |

```
acc gtc acc gcc gac gtc gag tgc ccg aag gac cgc gcg acc tgg tgc    576
Thr Val Thr Ala Asp Val Glu Cys Pro Lys Asp Arg Ala Thr Trp Cys
        180                 185                 190 atg acc cgc aag ccc ggt gcc tga                                    600
Met Thr Arg Lys Pro Gly Ala
        195
```

<210> SEQ ID NO 72
<211> LENGTH: 199
<212> TYPE: PRT
<213> ORGANISM: Artificial
<220> FEATURE:
<223> OTHER INFORMATION: Synthetic Construct

<400> SEQUENCE: 72

```
Met Thr Glu Tyr Lys Pro Thr Val Arg Leu Ala Thr Arg Asp Asp Val
1               5                   10                  15

Pro Arg Ala Val Arg Thr Leu Ala Ala Ala Phe Ala Asp Tyr Pro Ala
            20                  25                  30

Thr Arg His Thr Val Asp Pro Asp Arg His Ile Glu Arg Val Thr Glu
        35                  40                  45

Leu Gln Glu Leu Phe Leu Thr Arg Val Gly Leu Asp Ile Gly Lys Val
    50                  55                  60

Trp Val Ala Asp Asp Gly Ala Ala Val Ala Val Trp Thr Thr Pro Glu
65                  70                  75                  80

Ser Val Glu Ala Gly Ala Val Phe Ala Glu Ile Gly Pro Arg Met Ala
                85                  90                  95

Glu Leu Ser Gly Ser Arg Leu Ala Ala Gln Gln Met Glu Gly Leu
            100                 105                 110

Leu Ala Pro His Arg Pro Lys Glu Pro Ala Trp Phe Leu Ala Thr Val
        115                 120                 125

Gly Val Ser Pro Asp His Gln Gly Lys Gly Leu Gly Ser Ala Val Val
    130                 135                 140

Leu Pro Gly Val Glu Ala Ala Glu Arg Ala Gly Val Pro Ala Phe Leu
145                 150                 155                 160

Glu Thr Ser Ala Pro Arg Asn Leu Pro Phe Tyr Glu Arg Leu Gly Phe
                165                 170                 175

Thr Val Thr Ala Asp Val Glu Cys Pro Lys Asp Arg Ala Thr Trp Cys
            180                 185                 190

Met Thr Arg Lys Pro Gly Ala
        195
```

<210> SEQ ID NO 73
<211> LENGTH: 564
<212> TYPE: DNA
<213> ORGANISM: Artificial
<220> FEATURE:
<223> OTHER INFORMATION: wt DHFR gene (from mouse)
<220> FEATURE:
<221> NAME/KEY: CDS
<222> LOCATION: (1)..(564)

<400> SEQUENCE: 73

```
atg gtt cga cca ttg aac tgc atc gtc gcc gtg tcc caa aat atg ggg    48
Met Val Arg Pro Leu Asn Cys Ile Val Ala Val Ser Gln Asn Met Gly
1               5                   10                  15 att ggc aag aac gga gac cta ccc tgg cct ccg ctc agg aac gag ttc    96
Ile Gly Lys Asn Gly Asp Leu Pro Trp Pro Pro Leu Arg Asn Glu Phe
            20                  25                  30
```

```
aag tac ttc caa aga atg acc aca acc tct tca gtg aaa ggt aaa cag       144
Lys Tyr Phe Gln Arg Met Thr Thr Thr Ser Ser Val Glu Gly Lys Gln
         35                  40                  45 aat ctg gtg att atg ggt agg aaa acc tgg ttc tcc att cct gag aag       192
Asn Leu Val Ile Met Gly Arg Lys Thr Trp Phe Ser Ile Pro Glu Lys
 50                  55                  60 aat cga cct tta aag gac aga att aat ata gtt ctc agt aga gaa ctc       240
Asn Arg Pro Leu Lys Asp Arg Ile Asn Ile Val Leu Ser Arg Glu Leu
 65                  70                  75                  80 aaa gaa cca cca cga gga gct cat ttt ctt gcc aaa agt ttg gat gat       288
Lys Glu Pro Pro Arg Gly Ala His Phe Leu Ala Lys Ser Leu Asp Asp
                 85                  90                  95 gcc tta aga ctt att gaa caa ccg gaa ttg gca agt aaa gta gac atg       336
Ala Leu Arg Leu Ile Glu Gln Pro Glu Leu Ala Ser Lys Val Asp Met
            100                 105                 110 gtt tgg ata gtc gga ggc agt tct gtt tac cag gaa gcc atg aat caa       384
Val Trp Ile Val Gly Gly Ser Ser Val Tyr Gln Glu Ala Met Asn Gln
        115                 120                 125 cca ggc cac ctc aga ctc ttt gtg aca agg atc atg cag gaa ttt gaa       432
Pro Gly His Leu Arg Leu Phe Val Thr Arg Ile Met Gln Glu Phe Glu
130                 135                 140 agt gac acg ttt ttc cca gaa att gat ttg ggg aaa tat aaa ctt ctc       480
Ser Asp Thr Phe Phe Pro Glu Ile Asp Leu Gly Lys Tyr Lys Leu Leu
145                 150                 155                 160 cca gaa tac cca ggc gtc ctc tct gag gtc cag gag gaa aaa ggc atc       528
Pro Glu Tyr Pro Gly Val Leu Ser Glu Val Gln Glu Glu Lys Gly Ile
                165                 170                 175 aag tat aag ttt gaa gtc tac gag aag aaa gac taa                       564
Lys Tyr Lys Phe Glu Val Tyr Glu Lys Lys Asp
            180                 185
```

<210> SEQ ID NO 74
<211> LENGTH: 187
<212> TYPE: PRT
<213> ORGANISM: Artificial
<220> FEATURE:
<223> OTHER INFORMATION: Synthetic Construct
<400> SEQUENCE: 74

```
Met Val Arg Pro Leu Asn Cys Ile Val Ala Val Ser Gln Asn Met Gly
 1               5                  10                  15

Ile Gly Lys Asn Gly Asp Leu Pro Trp Pro Pro Leu Arg Asn Glu Phe
             20                  25                  30

Lys Tyr Phe Gln Arg Met Thr Thr Thr Ser Ser Val Glu Gly Lys Gln
         35                  40                  45

Asn Leu Val Ile Met Gly Arg Lys Thr Trp Phe Ser Ile Pro Glu Lys
 50                  55                  60

Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
                 85                  90                  95

Ala Leu Arg Leu Ile Glu Gln Pro Glu Leu Ala Ser Lys Val Asp Met
            100                 105                 110

Val Trp Ile Val Gly Gly Ser Ser Val Tyr Gln Glu Ala Met Asn Gln
        115                 120                 125

Pro Gly His Leu Arg Leu Phe Val Thr Arg Ile Met Gln Glu Phe Glu
130                 135                 140

Ser Asp Thr Phe Phe Pro Glu Ile Asp Leu Gly Lys Tyr Lys Leu Leu
145                 150                 155                 160
```

Pro Glu Tyr Pro Gly Val Leu Ser Glu Val Gln Glu Lys Gly Ile
            165                 170                 175

Lys Tyr Lys Phe Glu Val Tyr Glu Lys Lys Asp
            180                 185

<210> SEQ ID NO 75
<211> LENGTH: 1143
<212> TYPE: DNA
<213> ORGANISM: Artificial
<220> FEATURE:
<223> OTHER INFORMATION: wt hygromycin resistance gene
<220> FEATURE:
<221> NAME/KEY: CDS
<222> LOCATION: (1)..(1143)

<400> SEQUENCE: 75

```
atg aaa aag cct gaa ctc acc gcg acg tct gtc gag aag ttt ctg atc      48
Met Lys Lys Pro Glu Leu Thr Ala Thr Ser Val Glu Lys Phe Leu Ile
1               5                   10                  15 gaa aag ttc gac agc gtc tcc gac ctg atg cag ctc tcg gag ggc gaa      96
Glu Lys Phe Asp Ser Val Ser Asp Leu Met Gln Leu Ser Glu Gly Glu
                20                  25                  30 gaa tct cgt gct ttc agc ttc gat gta gga ggg cgt gga tat gtc ctg     144
Glu Ser Arg Ala Phe Ser Phe Asp Val Gly Gly Arg Gly Tyr Val Leu
            35                  40                  45 cgg gta aat agc tgc gcc gat ggt ttc tac aaa gat cgt tat gtt tat     192
Arg Val Asn Ser Cys Ala Asp Gly Phe Tyr Lys Asp Arg Tyr Val Tyr
        50                  55                  60 cgg cac ttt gca tcg gcc gcg ctc ccg att ccg gaa gtg ctt gac att     240
Arg His Phe Ala Ser Ala Ala Leu Pro Ile Pro Glu Val Leu Asp Ile
65                  70                  75                  80 ggg gaa ttc agc gag agc ctg acc tat tgc atc tcc cgc cgt gca cag     288
Gly Glu Phe Ser Glu Ser Leu Thr Tyr Cys Ile Ser Arg Arg Ala Gln
                85                  90                  95 ggt gtc acg ttg caa gac ctg cct gaa acc gaa ctg ccc gct gtt ctg     336
Gly Val Thr Leu Gln Asp Leu Pro Glu Thr Glu Leu Pro Ala Val Leu
            100                 105                 110 cag ccg gtc gcg gag gcc atg gat gcg atc gct gcg gcc gat ctt agc     384
Gln Pro Val Ala Glu Ala Met Asp Ala Ile Ala Ala Ala Asp Leu Ser
        115                 120                 125 cag acg agc ggg ttc ggc cca ttc gga ccg caa gga atc ggt caa tac     432
Gln Thr Ser Gly Phe Gly Pro Phe Gly Pro Gln Gly Ile Gly Gln Tyr
    130                 135                 140 act aca tgg cgt gat ttc ata tgc gcg att gct gat ccc cat gtg tat     480
Thr Thr Trp Arg Asp Phe Ile Cys Ala Ile Ala Asp Pro His Val Tyr
145                 150                 155                 160 cac tgg caa act gtg atg gac gac acc gtc agt gcg tcc gtc gcg cag     528
His Trp Gln Thr Val Met Asp Asp Thr Val Ser Ala Ser Val Ala Gln
                165                 170                 175 gct ctc gat gag ctg atg ctt tgg gcc gag gac tgc ccc gaa gtc cgg     576
Ala Leu Asp Glu Leu Met Leu Trp Ala Glu Asp Cys Pro Glu Val Arg
            180                 185                 190 cac ctc gtg cac gcg gat ttc ggc tcc aac aat gtc ctg acg gac aat     624
His Leu Val His Ala Asp Phe Gly Ser Asn Asn Val Leu Thr Asp Asn
        195                 200                 205 ggc cgc ata aca gcg gtc att gac tgg agc gag gcg atg ttc ggg gat     672
Gly Arg Ile Thr Ala Val Ile Asp Trp Ser Glu Ala Met Phe Gly Asp
    210                 215                 220 tcc caa tac gag gtc gcc aac atc ttc ttc tgg agg ccg tgg ttg gct     720
Ser Gln Tyr Glu Val Ala Asn Ile Phe Phe Trp Arg Pro Trp Leu Ala
225                 230                 235                 240
```

```
tgt atg gag cag cag acg cgc tac ttc gag cgg agg cat ccg gag ctt    768
Cys Met Glu Gln Gln Thr Arg Tyr Phe Glu Arg Arg His Pro Glu Leu
            245                 250                 255 gca gga tcg ccg cgg ctc cgg gcg tat atg ctc cgc att ggt ctt gac    816
Ala Gly Ser Pro Arg Leu Arg Ala Tyr Met Leu Arg Ile Gly Leu Asp
        260                 265                 270 caa ctc tat cag agc ttg gtt gac ggc aat ttc gat gat gca gct tgg    864
Gln Leu Tyr Gln Ser Leu Val Asp Gly Asn Phe Asp Asp Ala Ala Trp
    275                 280                 285 gcg cag ggt cga tgc gac gca atc gtc cga tcc gga gcc ggg act gtc    912
Ala Gln Gly Arg Cys Asp Ala Ile Val Arg Ser Gly Ala Gly Thr Val
290                 295                 300 ggg cgt aca caa atc gcc cgc aga agc gcg gcc gtc tgg acc gat ggc    960
Gly Arg Thr Gln Ile Ala Arg Arg Ser Ala Ala Val Trp Thr Asp Gly
305                 310                 315                 320 tgt gta gaa gta ctc gcc gat agt gga aac cga cgc ccc agc act cgt   1008
Cys Val Glu Val Leu Ala Asp Ser Gly Asn Arg Arg Pro Ser Thr Arg
            325                 330                 335 ccg gag gca aag gaa ttc ggg aga tgg ggg agg cta act gaa aca cgg   1056
Pro Glu Ala Lys Glu Phe Gly Arg Trp Gly Arg Leu Thr Glu Thr Arg
        340                 345                 350 aag gag aca ata ccg gaa gga acc cgc gct atg acg gca ata aaa aga   1104
Lys Glu Thr Ile Pro Glu Gly Thr Arg Ala Met Thr Ala Ile Lys Arg
    355                 360                 365 cag aat aaa acg cac ggg tgt tgg gtc gtt tgt tca taa               1143
Gln Asn Lys Thr His Gly Cys Trp Val Val Cys Ser
370                 375                 380

<210> SEQ ID NO 76
<211> LENGTH: 380
<212> TYPE: PRT
<213> ORGANISM: Artificial
<220> FEATURE:
<223> OTHER INFORMATION: Synthetic Construct

<400> SEQUENCE: 76

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175
```

```
Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
                260                 265                 270

Gln Leu Tyr Gln Ser Leu Val Asp Gly Asn Phe Asp Asp Ala Ala Trp
            275                 280                 285

Ala Gln Gly Arg Cys Asp Ala Ile Val Arg Ser Gly Ala Gly Thr Val
        290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Glu Ala Lys Glu Phe Gly Arg Trp Gly Arg Leu Thr Glu Thr Arg
                340                 345                 350

Lys Glu Thr Ile Pro Glu Gly Thr Arg Ala Met Thr Ala Ile Lys Arg
            355                 360                 365

Gln Asn Lys Thr His Gly Cys Trp Val Val Cys Ser
        370                 375                 380

<210> SEQ ID NO 77
<211> LENGTH: 804
<212> TYPE: DNA
<213> ORGANISM: Artificial
<220> FEATURE:
<223> OTHER INFORMATION: wt neomycin resistance gene
<220> FEATURE:
<221> NAME/KEY: CDS
<222> LOCATION: (1)..(804)

<400> SEQUENCE: 77 atg gga tcg gcc att gaa caa gat gga ttg cac gca ggt tct ccg gcc      48
Met Gly Ser Ala Ile Glu Gln Asp Gly Leu His Ala Gly Ser Pro Ala
1               5                   10                  15 gct tgg gtg gag agg cta ttc ggc tat gac tgg gca caa cag aca atc      96
Ala Trp Val Glu Arg Leu Phe Gly Tyr Asp Trp Ala Gln Gln Thr Ile
                20                  25                  30 ggc tgc tct gat gcc gcc gtg ttc cgg ctg tca gcg cag ggg cgc ccg     144
Gly Cys Ser Asp Ala Ala Val Phe Arg Leu Ser Ala Gln Gly Arg Pro
            35                  40                  45 gtt ctt ttt gtc aag acc gac ctg tcc ggt gcc ctg aat gaa ctg cag     192
Val Leu Phe Val Lys Thr Asp Leu Ser Gly Ala Leu Asn Glu Leu Gln
        50                  55                  60 gac gag gca gcg cgg cta tcg tgg ctg gcc acg acg ggc gtt cct tgc     240
Asp Glu Ala Ala Arg Leu Ser Trp Leu Ala Thr Thr Gly Val Pro Cys
65                  70                  75                  80 gca gct gtg ctc gac gtt gtc act gaa gcg gga agg gac tgg ctg cta     288
Ala Ala Val Leu Asp Val Val Thr Glu Ala Gly Arg Asp Trp Leu Leu
                85                  90                  95 ttg ggc gaa gtg ccg ggg cag gat ctc ctg tca tct cac ctt gct cct     336
Leu Gly Glu Val Pro Gly Gln Asp Leu Leu Ser Ser His Leu Ala Pro
```

```
                          100                 105                 110
gcc gag aaa gta tcc atc atg gct gat gca atg cgg cgg ctg cat acg      384
Ala Glu Lys Val Ser Ile Met Ala Asp Ala Met Arg Arg Leu His Thr
            115                 120                 125 ctt gat ccg gct acc tgc cca ttc gac cac caa gcg aaa cat cgc atc      432
Leu Asp Pro Ala Thr Cys Pro Phe Asp His Gln Ala Lys His Arg Ile
130                 135                 140 gag cga gca cgt act cgg atg gaa gcc ggt ctt gtc gat cag gat gat      480
Glu Arg Ala Arg Thr Arg Met Glu Ala Gly Leu Val Asp Gln Asp Asp
145                 150                 155                 160 ctg gac gaa gag cat cag ggg ctc gcg cca gcc gaa ctg ttc gcc agg      528
Leu Asp Glu Glu His Gln Gly Leu Ala Pro Ala Glu Leu Phe Ala Arg
                165                 170                 175 ctc aag gcg cgc atg ccc gac ggc gat gat ctc gtc gtg acc cat ggc      576
Leu Lys Ala Arg Met Pro Asp Gly Asp Asp Leu Val Val Thr His Gly
                180                 185                 190 gat gcc tgc ttg ccg aat atc atg gtg gaa aat ggc cgc ttt tct gga      624
Asp Ala Cys Leu Pro Asn Ile Met Val Glu Asn Gly Arg Phe Ser Gly
                195                 200                 205 ttc atc gac tgt ggc cgg ctg ggt gtg gcg gac cgc tat cag gac ata      672
Phe Ile Asp Cys Gly Arg Leu Gly Val Ala Asp Arg Tyr Gln Asp Ile
210                 215                 220 gcg ttg gct acc cgt gat att gct gaa gag ctt ggc ggc gaa tgg gct      720
Ala Leu Ala Thr Arg Asp Ile Ala Glu Glu Leu Gly Gly Glu Trp Ala
225                 230                 235                 240 gac cgc ttc ctc gtg ctt tac ggt atc gcc gct ccc gat tcg cag cgc      768
Asp Arg Phe Leu Val Leu Tyr Gly Ile Ala Ala Pro Asp Ser Gln Arg
                245                 250                 255 atc gcc ttc tat cgc ctt ctt gac gag ttc ttc tga                      804
Ile Ala Phe Tyr Arg Leu Leu Asp Glu Phe Phe
                260                 265

<210> SEQ ID NO 78
<211> LENGTH: 267
<212> TYPE: PRT
<213> ORGANISM: Artificial
<220> FEATURE:
<223> OTHER INFORMATION: Synthetic Construct

<400> SEQUENCE: 78

Met Gly Ser Ala Ile Glu Gln Asp Gly Leu His Ala Gly Ser Pro Ala
1               5                   10                  15

Ala Trp Val Glu Arg Leu Phe Gly Tyr Asp Trp Ala Gln Gln Thr Ile
            20                  25                  30

Gly Cys Ser Asp Ala Ala Val Phe Arg Leu Ser Ala Gln Gly Arg Pro
        35                  40                  45

Val Leu Phe Val Lys Thr Asp Leu Ser Gly Ala Leu Asn Glu Leu Gln
    50                  55                  60

Asp Glu Ala Ala Arg Leu Ser Trp Leu Ala Thr Thr Gly Val Pro Cys
65                  70                  75                  80

Ala Ala Val Leu Asp Val Val Thr Glu Ala Gly Arg Asp Trp Leu Leu
                85                  90                  95

Leu Gly Glu Val Pro Gly Gln Asp Leu Leu Ser Ser His Leu Ala Pro
                100                 105                 110

Ala Glu Lys Val Ser Ile Met Ala Asp Ala Met Arg Arg Leu His Thr
            115                 120                 125

Leu Asp Pro Ala Thr Cys Pro Phe Asp His Gln Ala Lys His Arg Ile
        130                 135                 140
```

```
Glu Arg Ala Arg Thr Arg Met Glu Ala Gly Leu Val Asp Gln Asp Asp
145                 150                 155                 160

Leu Asp Glu Glu His Gln Gly Leu Ala Pro Ala Glu Leu Phe Ala Arg
                165                 170                 175

Leu Lys Ala Arg Met Pro Asp Gly Asp Leu Val Val Thr His Gly
            180                 185                 190

Asp Ala Cys Leu Pro Asn Ile Met Val Glu Asn Gly Arg Phe Ser Gly
            195                 200                 205

Phe Ile Asp Cys Gly Arg Leu Gly Val Ala Asp Arg Tyr Gln Asp Ile
        210                 215                 220

Ala Leu Ala Thr Arg Asp Ile Ala Glu Glu Leu Gly Gly Glu Trp Ala
225                 230                 235                 240

Asp Arg Phe Leu Val Leu Tyr Gly Ile Ala Ala Pro Asp Ser Gln Arg
                245                 250                 255

Ile Ala Phe Tyr Arg Leu Leu Asp Glu Phe Phe
            260                 265

<210> SEQ ID NO 79
<211> LENGTH: 1121
<212> TYPE: DNA
<213> ORGANISM: Artificial
<220> FEATURE:
<223> OTHER INFORMATION: wt glutamine synthase gene (human)
<220> FEATURE:
<221> NAME/KEY: CDS
<222> LOCATION: (1)..(1119)

<400> SEQUENCE: 79 atg acc acc tca gca agt tcc cac tta aat aaa ggc atc aag cag gtg      48
Met Thr Thr Ser Ala Ser Ser His Leu Asn Lys Gly Ile Lys Gln Val
1               5                   10                  15 tac atg tcc ctg cct cag ggt gag aaa gtc cag gcc atg tat atc tgg      96
Tyr Met Ser Leu Pro Gln Gly Glu Lys Val Gln Ala Met Tyr Ile Trp
            20                  25                  30 atc gat ggt act gga gaa gga ctg cgc tgc aag acc cgg acc ctg gac     144
Ile Asp Gly Thr Gly Glu Gly Leu Arg Cys Lys Thr Arg Thr Leu Asp
        35                  40                  45 agt gag ccc aag tgt gtg gaa gag ttg cct gag tgg aat ttc gat ggc     192
Ser Glu Pro Lys Cys Val Glu Glu Leu Pro Glu Trp Asn Phe Asp Gly
    50                  55                  60 tcc agt act tta cag tct gag ggt tcc aac agt gac atg tat ctc gtg     240
Ser Ser Thr Leu Gln Ser Glu Gly Ser Asn Ser Asp Met Tyr Leu Val
65                  70                  75                  80 cct gct gcc atg ttt cgg gac ccc ttc cgt aag gac cct aac aag ctg     288
Pro Ala Ala Met Phe Arg Asp Pro Phe Arg Lys Asp Pro Asn Lys Leu
                85                  90                  95 gtg tta tgt gaa gtt ttc aag tac aat cga agg cct gca gag acc aat     336
Val Leu Cys Glu Val Phe Lys Tyr Asn Arg Arg Pro Ala Glu Thr Asn
            100                 105                 110 ttg agg cac acc tgt aaa cgg ata atg gac atg gtg agc aac cag cac     384
Leu Arg His Thr Cys Lys Arg Ile Met Asp Met Val Ser Asn Gln His
        115                 120                 125 ccc tgg ttt ggc atg gag cag gag tat acc ctc atg ggg aca gat ggg     432
Pro Trp Phe Gly Met Glu Gln Glu Tyr Thr Leu Met Gly Thr Asp Gly
    130                 135                 140 cac ccc ttt ggt tgg cct tcc aac ggc ttc cca ggg ccc cag ggt cca     480
His Pro Phe Gly Trp Pro Ser Asn Gly Phe Pro Gly Pro Gln Gly Pro
145                 150                 155                 160 tat tac tgt ggt gtg gga gca gac aga gcc tat ggc agg gac atc gtg     528
Tyr Tyr Cys Gly Val Gly Ala Asp Arg Ala Tyr Gly Arg Asp Ile Val
```

|  |  |  |  |  |  |  |  |  |  |  |  |  |  |  |  |
|---|---|---|---|---|---|---|---|---|---|---|---|---|---|---|---|
|  |  |  | 165 |  |  |  | 170 |  |  |  | 175 |  |  |  |  |
| gag | gcc | cat | tac | cgg | gcc | tgc | ttg | tat | gct | gga | gtc | aag | att | gcg | ggg | 576 |
| Glu | Ala | His | Tyr | Arg | Ala | Cys | Leu | Tyr | Ala | Gly | Val | Lys | Ile | Ala | Gly |  |
|  |  |  | 180 |  |  |  | 185 |  |  |  | 190 |  |  |  |  |
| act | aat | gcc | gag | gtc | atg | cct | gcc | cag | tgg | gaa | ttt | cag | att | gga | cct | 624 |
| Thr | Asn | Ala | Glu | Val | Met | Pro | Ala | Gln | Trp | Glu | Phe | Gln | Ile | Gly | Pro |  |
|  |  | 195 |  |  |  |  | 200 |  |  |  |  | 205 |  |  |  |  |
| tgt | gaa | gga | atc | agc | atg | gga | gat | cat | ctc | tgg | gtg | gcc | cgt | ttc | atc | 672 |
| Cys | Glu | Gly | Ile | Ser | Met | Gly | Asp | His | Leu | Trp | Val | Ala | Arg | Phe | Ile |  |
|  | 210 |  |  |  |  | 215 |  |  |  |  | 220 |  |  |  |  |  |
| ttg | cat | cgt | gtg | tgt | gaa | gac | ttt | gga | gtg | ata | gca | acc | ttt | gat | cct | 720 |
| Leu | His | Arg | Val | Cys | Glu | Asp | Phe | Gly | Val | Ile | Ala | Thr | Phe | Asp | Pro |  |
| 225 |  |  |  |  | 230 |  |  |  |  | 235 |  |  |  |  | 240 |  |
| aag | ccc | att | cct | ggg | aac | tgg | aat | ggt | gca | ggc | tgc | cat | acc | aac | ttc | 768 |
| Lys | Pro | Ile | Pro | Gly | Asn | Trp | Asn | Gly | Ala | Gly | Cys | His | Thr | Asn | Phe |  |
|  |  |  |  | 245 |  |  |  |  | 250 |  |  |  |  | 255 |  |  |
| agc | acc | aag | gcc | atg | cgg | gag | gag | aat | ggt | ctg | aag | tac | atc | gag | gag | 816 |
| Ser | Thr | Lys | Ala | Met | Arg | Glu | Glu | Asn | Gly | Leu | Lys | Tyr | Ile | Glu | Glu |  |
|  |  | 260 |  |  |  |  | 265 |  |  |  |  | 270 |  |  |  |  |
| gcc | att | gag | aaa | cta | agc | aag | cgg | cac | cag | tac | cac | atc | cgt | gcc | tat | 864 |
| Ala | Ile | Glu | Lys | Leu | Ser | Lys | Arg | His | Gln | Tyr | His | Ile | Arg | Ala | Tyr |  |
|  | 275 |  |  |  |  | 280 |  |  |  |  | 285 |  |  |  |  |  |
| gat | ccc | aag | gga | ggc | ctg | gac | aat | gcc | cga | cgt | cta | act | gga | ttc | cat | 912 |
| Asp | Pro | Lys | Gly | Gly | Leu | Asp | Asn | Ala | Arg | Arg | Leu | Thr | Gly | Phe | His |  |
| 290 |  |  |  |  | 295 |  |  |  |  | 300 |  |  |  |  |  |  |
| gaa | acc | tcc | aac | atc | aac | gac | ttt | tct | ggt | ggt | gta | gcc | aat | cgt | agc | 960 |
| Glu | Thr | Ser | Asn | Ile | Asn | Asp | Phe | Ser | Gly | Gly | Val | Ala | Asn | Arg | Ser |  |
| 305 |  |  |  | 310 |  |  |  |  | 315 |  |  |  |  | 320 |  |  |
| gcc | agc | ata | cgc | att | ccc | cgg | act | gtt | ggc | cag | gag | aag | aag | ggt | tac | 1008 |
| Ala | Ser | Ile | Arg | Ile | Pro | Arg | Thr | Val | Gly | Gln | Glu | Lys | Lys | Gly | Tyr |  |
|  |  |  |  | 325 |  |  |  |  | 330 |  |  |  |  | 335 |  |  |
| ttt | gaa | gat | cgt | cgc | ccc | tct | gcc | aac | tgc | gac | ccc | ttt | tcg | gtg | aca | 1056 |
| Phe | Glu | Asp | Arg | Arg | Pro | Ser | Ala | Asn | Cys | Asp | Pro | Phe | Ser | Val | Thr |  |
|  |  |  | 340 |  |  |  |  | 345 |  |  |  |  | 350 |  |  |  |
| gaa | gcc | ctc | atc | cgc | acg | tgt | ctt | ctc | aat | gaa | acc | ggc | gat | gag | ccc | 1104 |
| Glu | Ala | Leu | Ile | Arg | Thr | Cys | Leu | Leu | Asn | Glu | Thr | Gly | Asp | Glu | Pro |  |
|  | 355 |  |  |  |  | 360 |  |  |  |  | 365 |  |  |  |  |  |
| ttc | cag | tac | aaa | aat | ta |  |  |  |  |  |  |  |  |  |  | 1121 |
| Phe | Gln | Tyr | Lys | Asn |  |  |  |  |  |  |  |  |  |  |  |  |
|  | 370 |  |  |  |  |  |  |  |  |  |  |  |  |  |  |  |

<210> SEQ ID NO 80
<211> LENGTH: 373
<212> TYPE: PRT
<213> ORGANISM: Artificial
<220> FEATURE:
<223> OTHER INFORMATION: Synthetic Construct

<400> SEQUENCE: 80

Met Thr Thr Ser Ala Ser Ser His Leu Asn Lys Gly Ile Lys Gln Val
1               5                   10                  15

Tyr Met Ser Leu Pro Gln Gly Glu Lys Val Gln Ala Met Tyr Ile Trp
                20                  25                  30

Ile Asp Gly Thr Gly Glu Gly Leu Arg Cys Lys Thr Arg Thr Leu Asp
            35                  40                  45

Ser Glu Pro Lys Cys Val Glu Glu Leu Pro Glu Trp Asn Phe Asp Gly
        50                  55                  60

Ser Ser Thr Leu Gln Ser Glu Gly Ser Asn Ser Asp Met Tyr Leu Val
65                  70                  75                  80

```
Pro Ala Ala Met Phe Arg Asp Pro Phe Arg Lys Asp Pro Asn Lys Leu
                85                  90                  95

Val Leu Cys Glu Val Phe Lys Tyr Asn Arg Arg Pro Ala Glu Thr Asn
            100                 105                 110

Leu Arg His Thr Cys Lys Arg Ile Met Asp Met Val Ser Asn Gln His
        115                 120                 125

Pro Trp Phe Gly Met Glu Gln Glu Tyr Thr Leu Met Gly Thr Asp Gly
    130                 135                 140

His Pro Phe Gly Trp Pro Ser Asn Gly Phe Pro Gly Pro Gln Gly Pro
145                 150                 155                 160

Tyr Tyr Cys Gly Val Gly Ala Asp Arg Ala Tyr Gly Arg Asp Ile Val
                165                 170                 175

Glu Ala His Tyr Arg Ala Cys Leu Tyr Ala Gly Val Lys Ile Ala Gly
            180                 185                 190

Thr Asn Ala Glu Val Met Pro Ala Gln Trp Glu Phe Gln Ile Gly Pro
        195                 200                 205

Cys Glu Gly Ile Ser Met Gly Asp His Leu Trp Val Ala Arg Phe Ile
    210                 215                 220

Leu His Arg Val Cys Glu Asp Phe Gly Val Ile Ala Thr Phe Asp Pro
225                 230                 235                 240

Lys Pro Ile Pro Gly Asn Trp Asn Gly Ala Gly Cys His Thr Asn Phe
                245                 250                 255

Ser Thr Lys Ala Met Arg Glu Glu Asn Gly Leu Lys Tyr Ile Glu Glu
            260                 265                 270

Ala Ile Glu Lys Leu Ser Lys Arg His Gln Tyr His Ile Arg Ala Tyr
        275                 280                 285

Asp Pro Lys Gly Gly Leu Asp Asn Ala Arg Arg Leu Thr Gly Phe His
    290                 295                 300

Glu Thr Ser Asn Ile Asn Asp Phe Ser Gly Gly Val Ala Asn Arg Ser
305                 310                 315                 320

Ala Ser Ile Arg Ile Pro Arg Thr Val Gly Gln Glu Lys Lys Gly Tyr
                325                 330                 335

Phe Glu Asp Arg Arg Pro Ser Ala Asn Cys Asp Pro Phe Ser Val Thr
            340                 345                 350

Glu Ala Leu Ile Arg Thr Cys Leu Leu Asn Glu Thr Gly Asp Glu Pro
        355                 360                 365

Phe Gln Tyr Lys Asn
    370

<210> SEQ ID NO 81
<211> LENGTH: 154
<212> TYPE: DNA
<213> ORGANISM: Artificial
<220> FEATURE:
<223> OTHER INFORMATION: combined synthetic polyadenylation sequence and
      pausing signal from the human alpha2 globin gene
<220> FEATURE:
<221> NAME/KEY: synthetic polyadenylation sequence
<222> LOCATION: (1)..(49)
<220> FEATURE:
<221> NAME/KEY: cloning site
<222> LOCATION: (50)..(62)
<220> FEATURE:
<221> NAME/KEY: pausing signal from the human alpha2 globin gene
<222> LOCATION: (63)..(154)

<400> SEQUENCE: 81
aataaaatat ctttattttc attacatctg tgtgttggtt ttttgtgtga atcgatagta    60
```

-continued

```
ctaacatacg ctctccatca aaacaaaacg aaacaaaaca aactagcaaa ataggctgtc      120
cccagtgcaa gtgcaggtgc cagaacattt ctct                                  154

<210> SEQ ID NO 82
<211> LENGTH: 596
<212> TYPE: DNA
<213> ORGANISM: Artificial
<220> FEATURE:
<223> OTHER INFORMATION: IRES sequence

<400> SEQUENCE: 82
gcccctctcc ctccccccc cctaacgtta ctggccgaag ccgcttggaa taaggccggt       60
gtgcgtttgt ctatatgtga ttttccacca tattgccgtc ttttggcaat gtgagggccc     120
ggaaacctgg ccctgtcttc ttgacgagca ttcctagggg tctttcccct ctcgccaaag    180
gaatgcaagg tctgttgaat gtcgtgaagg aagcagttcc tctggaagct tcttgaagac    240
aaacaacgtc tgtagcgacc ctttgcaggc agcggaaccc cccacctggc gacaggtgcc    300
tctgcggcca aaagccacgt gtataagata cacctgcaaa ggcggcacaa ccccagtgcc    360
acgttgtgag ttggatagtt gtggaaagag tcaaatggct ctcctcaagc gtattcaaca    420
aggggctgaa ggatgcccag aaggtacccc attgtatggg atctgatctg gggcctcggt    480
gcacatgctt tacatgtgtt tagtcgaggt taaaaaaacg tctaggcccc ccgaaccacg    540
gggacgtggt tttcctttga aaaacacgat gataagcttg ccacaacccc gggata        596
```

SELECTION OF HOST CELLS EXPRESSING PROTEIN AT HIGH LEVELS

CROSS-REFERENCE TO RELATED APPLICATIONS

This application is a continuation-in-part of co-pending U.S. patent application Ser. No. 11/269,525, filed Nov. 7, 2005, which application claims priority under 35 U.S.C. Section 119(e) to U.S. Provisional Patent Appln. Ser. No. 60/626,301, filed Nov. 8, 2004, and to U.S. Provisional Patent Appln. Ser. No. 60/696,610, filed Jul. 5, 2005, the contents of the entirety of all three of which are incorporated by this reference. U.S. patent application Ser. No. 11/269,525 also claims the benefit of EP 04105593.0, filed Nov. 8, 2004, also incorporated herein. This application is further a continuation-in-part of co-pending U.S. patent application Ser. No. 11/359,953, filed Feb. 21, 2006, the contents of the entirety of which is incorporated by this reference, and which itself is a continuation-in-part of co-pending U.S. patent application Ser. No. 11/269,525, filed Nov. 7, 2005, also incorporated herein by this reference. This application is further a continuation-in-part of co-pending U.S. patent application Ser. No. 11/416,490, filed May 2, 2006, the contents of the entirety of which is incorporated by this reference, and which itself is a continuation-in-part of co-pending U.S. patent application Ser. No. 11/269,525, filed Nov. 7, 2005. This application is further a continuation-in-part of co-pending International Patent Appln. No. PCT/EP2007/051696, designating the United States, filed Feb. 21, 2007, and published in English as WO 07096399 A2 on Aug. 30, 2007, the contents of the entirety of which is incorporated by this reference, which International Patent Application claims priority to U.S. patent application Ser. No. 11/359,953, filed Feb. 21, 2006, and to U.S. patent application Ser. No. 11/416,490, filed May 2, 2006, and to EP 06113354.2, filed May 2, 2006, also incorporated herein.

STATEMENT ACCORDING TO 37 C.F.R. §1.52(e)(5)—SEQUENCE LISTING SUBMITTED ON COMPACT DISC

Pursuant to 37 C.F.R. §1.52(e) (1) (ii), a compact disc containing an electronic version of the Sequence Listing has been submitted concomitant with this application, the contents of which are incorporated herein by this reference. A second compact disc is submitted and is an identical copy of the first compact disc. The discs are labeled "copy 1" and "copy 2," respectively, and each disc contains one file entitled "2578-8510US seq list.txt" which is 168 KB and created on Sep. 4, 2007.

TECHNICAL FIELD

The invention relates to the field of molecular biology and biotechnology. More specifically, the invention relates to means and methods for improving the selection of host cells that express proteins at high levels.

BACKGROUND

Proteins can be produced in various host cells for a wide range of applications in biology and biotechnology, for instance as biopharmaceuticals. Eukaryotic, particularly mammalian, host cells are preferred for this purpose for expression of many proteins, for instance when such proteins have certain posttranslational modifications such as glycosylation. Methods for such production are well established, and generally entail the expression in a host cell of a nucleic acid (also referred to as 'transgene') encoding the protein of interest. In general, the transgene together with a selectable marker gene is introduced into a precursor cell, cells are selected for the expression of the selectable marker gene, and one or more clones that express the protein of interest at high levels are identified, and used for the expression of the protein of interest.

One problem associated with the expression of transgenes is that it is unpredictable, stemming from the high likelihood that the transgene will become inactive due to gene silencing (McBurney et al., 2002), and therefore many host cell clones have to be tested for high expression of the transgene.

Methods to select recombinant host cells that express relatively high levels of desired proteins are known, and several such methods are discussed in the introduction of WO 2006/048459, incorporated by reference herein.

In certain advantageous methods in the prior art, bicistronic expression vectors have been described for the rapid and efficient creation of stable mammalian cell lines that express recombinant protein. These vectors contain an internal ribosome entry site (IRES) between the upstream coding sequence for the protein of interest and the downstream coding sequence of the selection marker (Rees et al., 1996). Such vectors are commercially available, for instance the pIRES1 vectors from Clontech (CLONTECHniques, October 1996). Using such vectors for introduction into host cells, selection of sufficient expression of the downstream marker protein then automatically selects for high transcription levels of the multicistronic mRNA, and hence a strongly increased probability of high expression of the protein of interest is envisaged using such vectors. Preferably in such methods, the IRES used is an IRES which gives a relatively low level of translation of the selection marker gene, to further improve the chances of selecting for host cells with a high expression level of the protein of interest by selecting for expression of the selection marker protein (see, e.g., US 2005/0191723 and WO 2006/005718).

The invention aims at providing improved means and methods for selection of host cells expressing high levels of proteins of interest.

SUMMARY OF THE INVENTION

U.S. patent application Ser. No. 11/269,525, published as US 2006/0172382, is incorporated in its entirety by reference herein. US 2006/0172382 discloses a concept for selecting host cells expressing high levels of polypeptides of interest, the concept referred to therein as 'reciprocal interdependent translation'. In that concept, a multicistronic transcription unit is used wherein a sequence encoding a selectable marker polypeptide is upstream of a sequence encoding a polypeptide of interest, and wherein the translation of the selectable marker polypeptide is impaired by mutations therein, whereas translation of the polypeptide of interest is very high (see, e.g., FIG. 13 therein for a schematic view). The invention provides alternative means and methods for selecting host cells expressing high levels of polypeptide.

In one aspect, the invention provides a DNA molecule comprising a multicistronic transcription unit coding for i) a polypeptide of interest, and for ii) a selectable marker polypeptide functional in a eukaryotic host cell, wherein the polypeptide of interest has a translation initiation sequence separate from that of the selectable marker polypeptide, and wherein the coding sequence for the polypeptide of interest is upstream from the coding sequence for the selectable marker polypeptide in the multicistronic transcription unit, and wherein an internal ribosome entry site (IRES) is present downstream from the coding sequence for the polypeptide of interest and upstream from the coding sequence for the selectable marker polypeptide, and wherein the nucleic acid sequence coding for the selectable marker polypeptide in the coding strand comprises a translation start sequence chosen from the group consisting of: a) a GTG start codon; b) a TTG start codon; c) a CTG start codon; d) a ATT start codon; and e) a ACG start codon.

The translation start sequence in the coding strand for the selectable marker polypeptide comprises a start codon different from an ATG start codon, such as one of GTG, TTG, CTG, ATT, or ACG sequence, the first two thereof being the most preferred. Such non-ATG start codons preferably are flanked by sequences providing for relatively good recognition of the non-ATG sequences as start codons, such that at least some ribosomes start translation from these start codons, i.e., the translation start sequence preferably comprises the sequence ACC[non-ATG start codon]G or GCC[non-ATG start codon]G.

In certain embodiments, the selectable marker protein provides resistance against lethal and/or growth-inhibitory effects of a selection agent, such as an antibiotic.

Further provided are expression cassettes comprising a DNA molecule of the invention, which expression cassettes further comprise a promoter upstream of the multicistronic expression unit and are functional in a eukaryotic host cell for initiation transcription of the multicistronic expression unit, and the expression cassettes further comprising a transcription termination sequence downstream of the multicistronic expression unit.

In certain embodiments, such expression cassettes further comprise at least one chromatin control element chosen from the group consisting of a matrix or scaffold attachment region ("MAR/SAR"), an insulator sequence, a ubiquitous chromatin opener element ("UCOE"), and an anti-repressor sequence. Anti-repressor sequences may be used in this aspect, and, in certain embodiments, the anti-repressor sequences are selected from the group consisting of: a) any one SEQ ID NO: 1 through SEQ ID NO: 66; b) fragments of any one of SEQ ID NO: 1 through SEQ ID NO: 66, wherein the fragments have anti-repressor activity; c) sequences that have at least 70% sequence identity to nucleotide sequence to a) or b) wherein the sequences have anti-repressor activity; and d) the complement to any one of a) to c).

Also provided are host cells comprising DNA molecules of the invention.

Further provided are methods for generating host cells expressing a polypeptide of interest, the method comprising the steps of: introducing into a plurality of precursor host cells, a DNA molecule or molecules or an expression cassette of the invention, culturing the cells under conditions selecting for expression of the selectable marker polypeptide, and selecting at least one host cell producing the polypeptide of interest.

In a further aspect, provided are methods for producing a polypeptide of interest, the methods comprising culturing a host cell, the host cell comprising an expression cassette of the invention, and expressing the polypeptide of interest from the expression cassette. In certain embodiments, the polypeptide of interest is further isolated from the host cells and/or from the host cell culture medium.

DETAILED DESCRIPTION OF THE INVENTION

Figure 1:
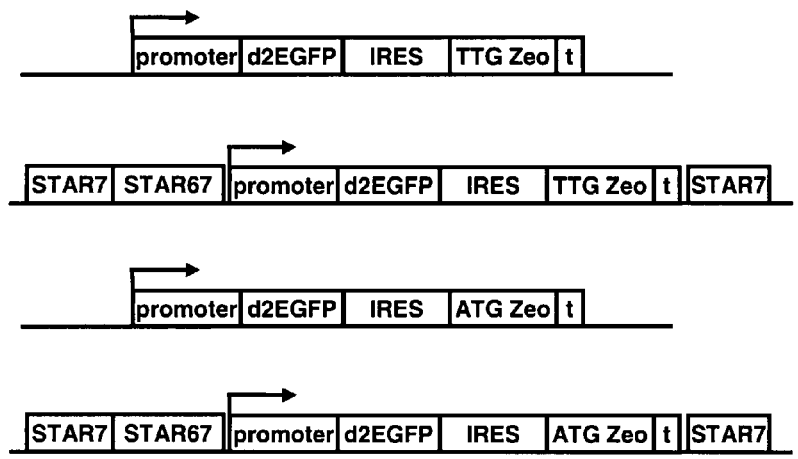
FIG. 1. Results with expression constructs of the invention. The expression construct contains the sequence encoding the polypeptide of interest (exemplified here by d2EGFP) upstream of an IRES, which is upstream of the sequence encoding the selectable marker of the invention (exemplified here by the ZEOCIN™ resistance gene, with a TTG start codon (TTG Zeo) (or in controls with its normal ATG start codon (ATG Zeo)). See example 1 for details. Dots indicate individual data points; lines indicate the average expression levels; used constructs are indicated on the horizontal axis, and schematically depicted above the graph; vertical axis indicates d2EGFP signal.
Figure 1:
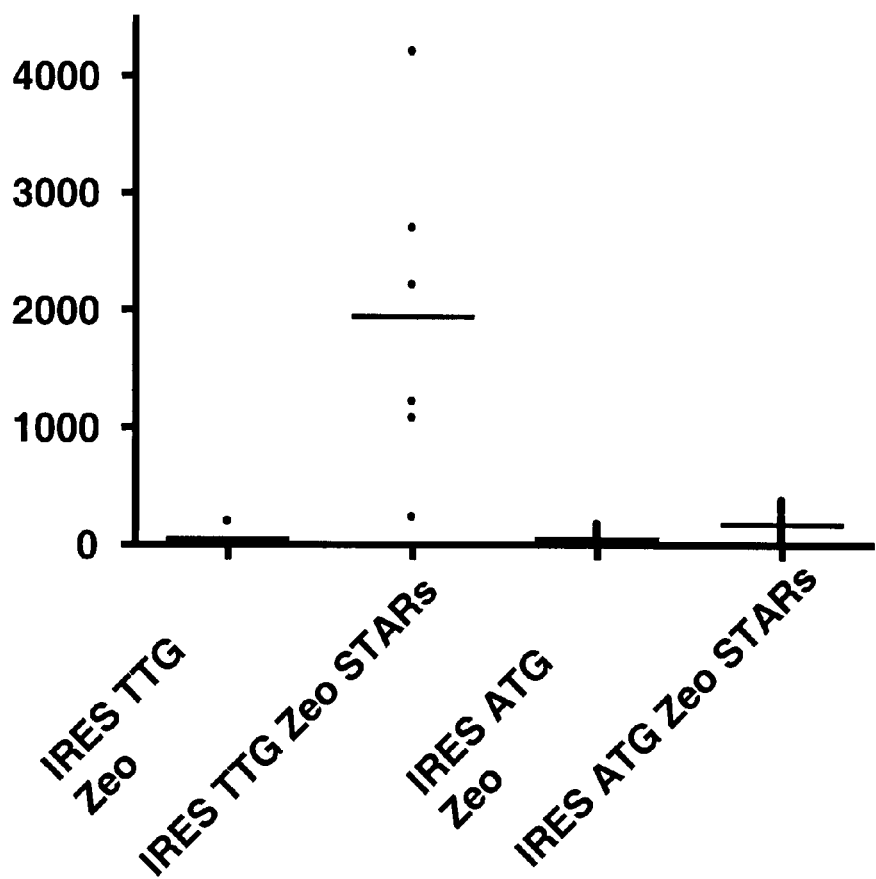

In certain aspects, the invention provides a DNA molecule of the invention. Such a DNA molecule can be used for obtaining eukaryotic host cells expressing high levels of the polypeptide of interest, by selecting for the expression of the selectable marker polypeptide. Subsequently or simultaneously, one or more host cell(s) expressing the polypeptide of interest can be identified, and further used for expression of high levels of the polypeptide of interest.

The term "monocistronic gene" is defined as a gene capable of providing a RNA molecule that encodes one polypeptide. A "multicistronic transcription unit", also referred to as multicistronic gene, is defined as a gene capable of providing an RNA molecule that encodes at least two polypeptides. The term "bicistronic gene" is defined as a gene capable of providing a RNA molecule that encodes two polypeptides. A bicistronic gene is therefore encompassed within the definition of a multicistronic gene. A "polypeptide" as used herein comprises at least five amino acids linked by peptide bonds, and can for instance be a protein or a part, such as a subunit, thereof. Mostly, the terms polypeptide and protein are used interchangeably herein. A "gene" or a "transcription unit" as used in the invention can comprise chromosomal DNA, cDNA, artificial DNA, combinations thereof, and the like. Transcription units comprising several cistrons are transcribed as a single mRNA.

A multicistronic transcription unit of the invention preferably is a bicistronic transcription unit coding from 5' to 3' for a polypeptide of interest and for a selectable marker polypeptide. Hence, the polypeptide of interest is encoded upstream from the coding sequence for the selectable marker polypeptide. The IRES is operably linked to the sequence encoding the selectable marker polypeptide, and hence the selectable marker polypeptide is dependent from the IRES for its translation.

It is preferred to use separate transcription units for the expression of different polypeptides of interest, also when these form part of a multimeric protein (see, e.g., Example 13 of the incorporated herein US 2006/0172382: the heavy and light chain of an antibody each are encoded by a separate transcription unit, each of these expression units being a bicistronic expression unit).

The DNA molecules of the invention can be present in the form of double stranded DNA, having with respect to the selectable marker polypeptide and the polypeptide of interest a coding strand and a non-coding strand, the coding strand being the strand with the same sequence as the translated RNA, except for the presence of T instead of U. Hence, an AUG start codon is coded for in the coding strand by an ATG sequence, and the strand containing this ATG sequence corresponding to the AUG start codon in the RNA is referred to as the coding strand of the DNA. It will be clear to the skilled person that start codons or translation initiation sequences are in fact present in an RNA molecule, but that these can be considered equally embodied in a DNA molecule coding for such an RNA molecule; hence, wherever the invention refers to a start codon or translation initiation sequence, the corresponding DNA molecule having the same sequence as the RNA sequence but for the presence of a T instead of a U in the coding strand of the DNA molecule is meant to be included, and vice versa, except where explicitly specified otherwise. In other words, a start codon is for instance an AUG sequence in RNA, but the corresponding ATG sequence in the coding strand of the DNA is referred to as start codon as well in the invention. The same is used for the reference of 'in frame' coding sequences, meaning triplets (3 bases) in the RNA molecule that are translated into an amino acid, but also to be interpreted as the corresponding trinucleotide sequences in the coding strand of the DNA molecule.

The selectable marker polypeptide and the polypeptide of interest encoded by the multicistronic gene each have their own translation initiation sequence, and therefore each have their own start codon (as well as stop codon), i.e., they are encoded by separate open reading frames.

The term "selection marker" or "selectable marker" is typically used to refer to a gene and/or protein whose presence can be detected directly or indirectly in a cell, for example a polypeptide that inactivates a selection agent and protects the host cell from the agent's lethal or growth-inhibitory effects (e.g., an antibiotic resistance gene and/or protein). Another possibility is that the selection marker induces fluorescence or a color deposit (e.g., green fluorescent protein (GFP) and derivatives (e.g., d2EGFP), luciferase, lacZ, alkaline phosphatase, etc.), which can be used for selecting cells expressing the polypeptide inducing the color deposit, e.g., using a fluorescence activated cell sorter (FACS) for selecting cells that express GFP. In certain embodiments, the selectable marker polypeptide of the invention provides resistance against lethal and/or growth-inhibitory effects of a selection agent. The selectable marker polypeptide is encoded by the DNA of the invention. The selectable marker polypeptide of the invention must be functional in a eukaryotic host cell, and hence being capable of being selected for in eukaryotic host cells. Any selectable marker polypeptide fulfilling this criterion can in principle be used according to the invention. Such selectable marker polypeptides are well known in the art and routinely used when eukaryotic host cell clones are to be obtained, and several examples are provided herein. In certain embodiments, a selection marker used for the invention is ZEOCIN™ broad spectrum antibiotic ($C_{55}H_{83}N_{19}O_{21}S_2Cu$; MW=1137.4 g/mole; soluble in water; CAS [11006-33-0]) or "zeocin", which is readily commercially available. In other embodiments, blasticidin is used. The person skilled in the art will know that other selection markers are available and can be used, e.g., neomycin, puromycin, bleomycin, hygromycin, etc. In other embodiments, kanamycin is used. In yet other embodiments, the dhfr gene is used as a selectable marker, which can be selected for by methotrexate, especially by increasing the concentration of methotrexate cells can be selected for increased copy numbers of the dhfr gene. The dhfr gene may also be used to complement DHFR-deficiency, e.g., in CHO cells that have a DHFR⁻ phenotype, in culture medium with folate and lacking glycine, hypoxanthine and thymidine. Similarly, the glutamine synthetase (GS) gene can be used, for which selection is possible in cells having insufficient GS (e.g., NS-0 cells) by culturing in media without glutamine, or alternatively in cells having sufficient GS (e.g., CHO cells) by adding an inhibitor of GS, methionine sulphoximine (MSX). Other selectable marker genes that could be used, and their selection agents, are for instance described in Table 1 of U.S. Pat. No. 5,561,053, incorporated by reference herein; see also Kaufman, Methods in Enzymology, 185:537-566 (1990), for a review of these. If the selectable marker polypeptide is DHFR, the host cell in advantageous embodiments is cultured in a culture medium that contains folate and which culture medium is essentially devoid of hypoxanthine and thymidine, and preferably also of glycine.

When two multicistronic transcription units are to be selected for of the invention in a single host cell, each one preferably contains the coding sequence for a different selectable marker, to allow selection for both multicistronic transcription units. Of course, both multicistronic transcription units may be present on a single nucleic acid molecule or alternatively each one may be present on a separate nucleic acid molecule.

The term "selection" is typically defined as the process of using a selection marker/selectable marker and a selection agent to identify host cells with specific genetic properties (e.g., that the host cell contains a transgene integrated into its genome). It is clear to a person skilled in the art that numerous combinations of selection markers are possible. One antibiotic that is particularly advantageous is ZEOCIN™, because the ZEOCIN™-resistance protein (ZEOCIN™-R) acts by binding the drug and rendering it harmless. Therefore it is easy to titrate the amount of drug that kills cells with low levels of ZEOCIN™-R expression, while allowing the high-expressors to survive. All other antibiotic-resistance proteins in common use are enzymes, and thus act catalytically (not 1:1 with the drug). Hence, the antibiotic ZEOCIN™ is a preferred selection marker. Another preferred selection marker is a 5,6,7,8-tetrahydrofolate synthesizing enzyme (DHFR). However, the invention also works with other selection markers.

A selectable marker polypeptide of the invention is the protein that is encoded by the nucleic acid of the invention, which polypeptide can be functionally used for selection, for instance because it provides resistance to a selection agent such as an antibiotic. Hence, when an antibiotic is used as a selection agent, the DNA encodes a polypeptide that confers resistance to the selection agent, which polypeptide is the selectable marker polypeptide. DNA sequences coding for such selectable marker polypeptides are known, and several examples of wild-type sequences of DNA encoding selectable marker proteins are provided herein (e.g., FIGS. 26-32 of the incorporated herein US 2006/0172382). It will be clear that mutants or derivatives of selectable markers can also be suitably used of the invention, and are therefore included within the scope of the term 'selectable marker polypeptide', as long as the selectable marker protein is still functional.

For convenience and as generally accepted by the skilled person, in many publications as well as herein, often the gene and protein encoding the resistance to a selection agent is referred to as the 'selectable agent (resistance) gene' or 'selection agent (resistance) protein', respectively, although the official names may be different, e.g., the gene coding for the protein conferring resistance to neomycin (as well as to G418 and kanamycin) is often referred to as neomycin (resistance) (or neo$^r$) gene, while the official name is aminoglycoside 3'-phosphotransferase gene.

For the invention, it is beneficial to have low levels of expression of the selectable marker polypeptide, so that stringent selection is possible. This may be brought about by using a selectable marker coding sequence with a non-ATG start codon. Upon selection, only cells that have nevertheless sufficient levels of selectable marker polypeptide will be selected, meaning that such cells must have sufficient transcription of the multicistronic transcription unit and sufficient translation of the selectable marker polypeptide, which provides a selection for cells where the multicistronic transcription unit has been integrated or otherwise present in the host cells at a place where expression levels from this transcription unit are high.

DNA molecules of the invention have the coding sequence for the selectable marker polypeptide downstream of the coding sequence for the polypeptide of interest. Hence, the multicistronic transcription unit comprises in the 5' to 3' direction (both in the transcribed strand of the DNA and in the resulting transcribed RNA) the sequence encoding the polypeptide of interest and the coding sequence for the selectable marker polypeptide. The IRES is upstream of the coding sequence for the selectable marker polypeptide.

Of the invention, the coding region of the gene of interest is preferably translated from the cap-dependent ORF, and the polypeptide of interest is produced in abundance. The selectable marker polypeptide is translated from an IRES. To decrease translation of the selectable marker cistron, of the invention the nucleic acid sequence coding for the selectable marker polypeptide comprises a mutation in the start codon that decreases the translation initiation efficiency of the selectable marker polypeptide in a eukaryotic host cell. In certain embodiments, a GTG start codon or more preferably a TTG start codon is engineered into the selectable marker polypeptide. The translation efficiency is lower than that of the corresponding wild-type sequence in the same cell, i.e., the mutation results in less polypeptide per cell per time unit, and hence less selectable marker polypeptide.

A translation start sequence is often referred to in the field as 'Kozak sequence', and an optimal Kozak sequence is RCC<u>ATG</u>G, the start codon underlined, R being a purine, i.e., A or G (see, Kozak M, 1986, 1987, 1989, 1990, 1997, 2002). Hence, besides the start codon itself, the context thereof, in particular nucleotides −3 to −1 and +4, are relevant, and an optimal translation start sequence comprises an optimal start codon (i.e., ATG) in an optimal context (i.e., the ATG directly preceded by RCC and directly followed by G). Translation by the ribosomes is most efficient when an optimal Kozak sequence is present (see, Kozak M, 1986, 1987, 1989, 1990, 1997, 2002). However, in a small percentage of events, non-optimal translation initiation sequences are recognized and used by the ribosome to start translation. The invention makes use of this principle, and allows for decreasing and even fine-tuning of the amount of translation and hence expression of the selectable marker polypeptide, which can therefore be used to increase the stringency of the selection system.

The ATG start codon of the selectable marker polypeptide in the invention is mutated into another codon, which has been reported to provide some translation initiation, for instance to GTG, TTG, CTG, ATT, or ACG (collectively referred to herein as 'non-ATG start codons'). In certain embodiments, the ATG start codon is mutated into a GTG start codon. This provides still lower expression levels (lower translation) than with the ATG start codon intact but in a non-optimal context. More In certain embodiments, the ATG start codon is mutated to a TTG start codon, which provides even lower expression levels of the selectable marker polypeptide than with the GTG start codon (Kozak M, 1986, 1987, 1989, 1990, 1997, 2002; see also examples 9-13 in US 2006/0172382, incorporated by reference herein). The use of non-ATG start codons in the coding sequence for a selectable marker polypeptide in a multicistronic transcription unit according to the invention was not disclosed nor suggested in the prior art and, preferably in combination with chromatin control elements, leads to very high levels of expression of the polypeptide of interest, as also shown in the incorporated herein US 2006/0172382.

For the use of a non-ATG start codon of the invention, it is strongly preferred to provide an optimal context for such a start codon, i.e., the non-ATG start codons are preferably directly preceded by nucleotides RCC in positions −3 to −1 and directly followed by a G nucleotide (position +4). However, it has been reported that using the sequence TTT<u>GTG</u>G (start codon underlined), some initiation is observed at least in vitro, so although strongly preferred it may not be absolutely required to provide an optimal context for the non-ATG start codons.

ATG sequences within the coding sequence for a polypeptide, but excluding the ATG start codon, are referred to as 'internal ATGs', and if these are in frame with the ORF and therefore code for methionine, the resulting methionine in the polypeptide is referred to as an 'internal methionine'. In the invention of US 2006/0172382 the coding region (following the start codon, not necessarily including the start codon)

coding for the selectable marker polypeptide is devoid of any ATG sequence in the coding strand of the DNA, up to (but not including) the start codon of the polypeptide of interest. US 2006/0172382 discloses how to bring this about and how to test the resulting selectable marker polypeptides for functionality. For the invention, where the selectable marker polypeptide coding sequence is downstream of an IRES and downstream of the coding sequence for the polypeptide of interest, internal ATGs in the sequence encoding the selectable marker polypeptide can remain intact.

The translation start sequence of the polypeptide of interest may comprise an optimal translation start sequence, i.e., having the consensus sequence RCC<u>ATG</u>G (start codon underlined). This will result in a very efficient translation of the polypeptide of interest.

By providing the coding sequence of the marker with different mutations leading to several levels of decreased translation efficiency, the stringency of selection can be increased. Fine-tuning of the selection system is thus possible using the multicistronic transcription units of the invention: for instance using a GTG start codon for the selection marker polypeptide, only few ribosomes will translate from this start codon, resulting in low levels of selectable marker protein, and hence a high stringency of selection; using a TTG start codon even further increases the stringency of selection because even less ribosomes will translate the selectable marker polypeptide from this start codon.

It is demonstrated in the incorporated herein US 2006/0172382 that the multicistronic expression units disclosed therein can be used in a very robust selection system, leading to a very large percentage of clones that express the polypeptide of interest at high levels, as desired. In addition, the expression levels obtained for the polypeptide of interest appear to be significantly higher than those obtained when an even larger number of colonies are screened using selection systems hitherto known.

In addition to a decreased translation initiation efficiency, it could be beneficial to also provide for decreased translation elongation efficiency of the selectable marker polypeptide, e.g., by mutating the coding sequence thereof so that it comprises several non-preferred codons of the host cell, in order to further decrease the translation levels of the marker polypeptide and allow still more stringent selection conditions, if desired. In certain embodiments, besides the mutation(s) that decrease the translation efficiency of the invention, the selectable marker polypeptide further comprises a mutation that reduces the activity of the selectable marker polypeptide compared to its wild-type counterpart. This may be used to increase the stringency of selection even further. As non-limiting examples, proline at position 9 in the ZEO-CIN™ resistance polypeptide may be mutated, e.g., to Thr or Phe (see, e.g., Example 14 of the incorporated US 2006/0172382), and for the neomycin resistance polypeptide, amino acid residue 182 or 261 or both may further be mutated (see, e.g., WO 01/32901, also incorporated herein by this reference).

In some embodiments of the invention, a so-called spacer sequence is placed downstream of the sequence encoding the start codon of the selectable marker polypeptide, which spacer sequence preferably is a sequence in frame with the start codon and encoding a few amino acids, and that does not contain a secondary structure (Kozak, 1990). Such a spacer sequence can be used to further decrease the translation initiation frequency if a secondary structure is present in the RNA (Kozak, 1990) of the selectable marker polypeptide (e.g., for ZEOCIN™, possibly for blasticidin), and hence increase the stringency of the selection system of the invention (see, e.g., Example 14 of the incorporated US 2006/0172382).

It will be clear that any DNA molecules as described but having mutations in the sequence downstream of the first ATG (start codon) coding for the selectable marker protein can also be used and are thus also encompassed in the invention, as long as the respective encoded selectable marker protein still has activity. For instance, any silent mutations that do not alter the encoded protein because of the redundancy of the genetic code are also encompassed. Further mutations that lead to conservative amino acid mutations or to other mutations are also encompassed, as long as the encoded protein still has activity, which may or may not be lower than that of the wild-type protein as encoded by the indicated sequences. In particular, it is preferred that the encoded protein have at least 70%, preferably at least 80%, more preferably at least 90%, still more preferably at least 95% sequence identity to the proteins encoded by the respective indicated sequences (e.g., as provided in SEQ ID NOs. 68-80 of the accompanying Sequence Listing of the present application incorporated herein). Testing for activity of the selectable marker proteins can be done by routine methods.

In certain aspects of the invention, it is preferred to provide an expression cassette comprising the DNA molecule of the invention, having the multicistronic transcription unit. Such an expression cassette is useful to express sequences of interest, for instance, in host cells. An 'expression cassette' as used herein is a nucleic acid sequence comprising at least a promoter functionally linked to a sequence of which expression is desired. In certain embodiments, an expression cassette further contains transcription termination and polyadenylation sequences. Other regulatory sequences such as enhancers may also be included. Hence, the invention provides an expression cassette comprising in the following order: 5'-promoter—multicistronic transcription unit of the invention, coding for a polypeptide of interest and downstream thereof a selectable marker polypeptide—transcription termination sequence—3'. The promoter must be capable of functioning in a eukaryotic host cell, i.e., it must be capable of driving transcription of the multicistronic transcription unit. The promoter is thus operably linked to the multicistronic transcription unit. The expression cassette may optionally further contain other elements known in the art, e.g., splice sites to comprise introns, and the like. In some embodiments, an intron is present behind the promoter and before the sequence encoding the polypeptide of interest. An IRES is operably linked to the cistron that contains the selectable marker polypeptide coding sequence. In further embodiments, a sequence coding for a second selectable marker is present in the multicistronic transcription unit (i.e., this is at least a tricistronic transcription unit in these embodiments). In certain embodiments thereof, the sequence encoding a second selectable marker polypeptide: a) has a translation initiation sequence separate from that of the polypeptide of interest, b) is positioned upstream of the sequence encoding a polypeptide of interest, c) has no ATG sequence in the coding strand following the start codon of the second selectable marker polypeptide up to the start codon of the polypeptide of interest, and d) has a non-optimal translation start sequence, e.g., a GTG start codon or a TTG start codon. For such embodiments, a preferred selectable marker polypeptide is a 5,6,7,8-tetrahydrofolate synthesizing enzyme (dihydrofolate reductase, DHFR). This allows for continuous selection of high levels of expression of the polypeptide of interest, as exemplified in Examples 2 and 4.

To obtain expression of nucleic acid sequences encoding protein, it is well known to those skilled in the art that sequences capable of driving such expression, can be functionally linked to the nucleic acid sequences encoding the protein, resulting in recombinant nucleic acid molecules encoding a protein in expressible format. In the invention, the expression cassette comprises a multicistronic transcription unit. In general, the promoter sequence is placed upstream of the sequences that should be expressed. Much used expression vectors are available in the art, e.g., the pcDNA and pEF vector series of Invitrogen, pMSCV and pTK-Hyg from BD Sciences, pCMV-Script from Stratagene, etc., which can be used to obtain suitable promoters and/or transcription terminator sequences, polyA sequences, and the like.

Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. The person skilled in the art is aware that various promoters can be used to obtain expression of a gene in host cells. Promoters can be constitutive or regulated, and can be obtained from various sources, including viruses, prokaryotic, or eukaryotic sources, or artificially designed. Expression of nucleic acids of interest may be from the natural promoter or derivative thereof or from an entirely heterologous promoter (Kaufman, 2000). According to the invention, strong promoters that give high transcription levels in the eukaryotic cells of choice are preferred. Suitable promoters are well known and available to the skilled person, and several are described in the incorporated US 2006/0172382 (e.g., paragraphs [0110]-[0111]), including the CMV immediate early (IE) promoter (referred to herein as the CMV promoter) (obtainable for instance from pcDNA, Invitrogen, and many others).

In certain embodiments, a DNA molecule of the invention is part of a vector, e.g., a plasmid. Such vectors can easily be manipulated by methods well known to the person skilled in the art, and can for instance be designed for being capable of replication in prokaryotic and/or eukaryotic cells. In addition, many vectors can directly or in the form of isolated desired fragment therefrom be used for transformation of eukaryotic cells and will integrate in whole or in part into the genome of such cells, resulting in stable host cells comprising the desired nucleic acid in their genome.

Conventional expression systems are DNA molecules in the form of a recombinant plasmid or a recombinant viral genome. The plasmid or the viral genome is introduced into (eukaryotic host) cells and preferably integrated into their genomes by methods known in the art, and several aspects hereof have been described in the incorporated US 2006/0172382 (e.g., paragraphs [0112]-[0114]).

It is widely appreciated that chromatin structure and other epigenetic control mechanisms may influence the expression of transgenes in eukaryotic cells (e.g., Whitelaw et al., 2001). The multicistronic expression units of the invention form part of a selection system with a rather rigourous selection regime. This generally requires high transcription levels in the host cells of choice. To increase the chance of finding clones of host cells that survive the rigorous selection regime, and possibly to increase the stability of expression in obtained clones, it will generally be preferable to increase the predictability of transcription. Therefore, in certain embodiments, an expression cassette of the invention further comprises at least one chromatin control element. A 'chromatin control element' as used herein is a collective term for DNA sequences that may somehow have an effect on the chromatin structure and therewith on the expression level and/or stability of expression of transgenes in their vicinity (they function 'in cis', and hence are placed preferably within 5 kb, more preferably within 2 kb, still more preferably within 1 kb from the transgene) within eukaryotic cells. Such elements have sometimes been used to increase the number of clones having desired levels of transgene expression. Several types of such elements that can be used in accordance with the invention have been described in the incorporated US 2006/0172382 (e.g., paragraphs [0115]-[0117]), and for the purpose of the invention chromatin control elements are chosen from the group consisting of matrix or scaffold attachment regions (MARs/SARs), insulators such as the beta-globin insulator element (5' HS4 of the chicken beta-globin locus), scs, scs', and the like, a ubiquitous chromatin opening element (UCOE), and anti-repressor sequences (also referred to as 'STAR' sequences).

Preferably, the chromatin control element is an anti-repressor sequence, preferably chosen from the group consisting of: a) any one SEQ ID NO: 1 through SEQ ID NO: 66; b) fragments of any one of SEQ ID NO: 1 through SEQ ID NO: 66, wherein the fragments have anti-repressor activity ('functional fragments'); c) sequences that are at least 70% identical in nucleotide sequence to a) or b) wherein the sequences have anti-repressor activity ('functional derivatives'); and d) the complement to any one of a) to c). In certain embodiments, the chromatin control element is chosen from the group consisting of STAR67 (SEQ ID NO: 66), STAR7 (SEQ ID NO: 7), STAR9 (SEQ ID NO: 9), STAR17 (SEQ ID NO: 17), STAR27 (SEQ ID NO: 27), STAR29 (SEQ ID NO: 29), STAR43 (SEQ ID NO: 43), STAR44 (SEQ ID NO: 44), STAR45 (SEQ ID NO: 45), STAR47 (SEQ ID NO: 47), STAR61 (SEQ ID NO: 61), or a functional fragment or derivative of the STAR sequences. In a preferred embodiment, the STAR sequence is STAR 67 (SEQ ID NO: 66) or a functional fragment or derivative thereof. In certain certain embodiments, STAR 67 or a functional fragment or derivative thereof is positioned upstream of a promoter driving expression of the multicistronic transcription unit. In certain other embodiments, the expression cassettes of the invention are flanked on both sides by at least one anti-repressor sequence, e.g., by one of SEQ ID NO: 1 through SEQ ID NO: 65 on both sides, preferably each with the 3' end of these sequences facing the transcription unit. In certain embodiments, expression cassettes are provided of the invention, comprising in 5' to 3' order: anti-repressor sequence A—anti-repressor sequence B—[promoter—multicistronic transcription unit of the invention (encoding the polypeptide of interest and downstream thereof the functional selectable marker protein)—transcription termination sequence]—anti-repressor sequence C, wherein A, B and C may be the same or different.

Sequences having anti-repressor activity (anti-repressor sequences) and characteristics thereof, as well as functional fragments or derivatives thereof, and structural and functional definitions thereof, and methods for obtaining and using them, which sequences are useful for the invention, have been described in the incorporated US 2006/0172382 (e.g., paragraphs [0116]-[0126]).

For the production of multimeric proteins, two or more expression cassettes can be used. In certain embodiments, both expression cassettes are multicistronic expression cassettes of the invention, each coding for a different selectable marker protein, so that selection for both expression cassettes is possible. This embodiment has given good results, e.g., for the expression of the heavy and light chain of antibodies. It will be clear that both expression cassettes may be placed on one nucleic acid molecule or both may be present on a separate nucleic acid molecule, before they are introduced into host cells. An advantage of placing them on one nucleic acid molecule is that the two expression cassettes are present in a single predetermined ratio (e.g., 1:1) when introduced into host cells. On the other hand, when present on two different nucleic acid molecules, this allows the possibility to vary the molar ratio of the two expression cassettes when introducing them into host cells, which may be an advantage if the preferred molar ratio is different from 1:1 or when it is unknown beforehand what is the preferred molar ratio, so that variation thereof and empirically finding the optimum can easily be performed by the skilled person. In certain embodiments, at least one of the expression cassettes, but preferably each of them, comprises a chromatin control element, more preferably an anti-repressor sequence.

In another embodiment, the different subunits or parts of a multimeric protein are present on a single expression cassette.

Useful configurations of anti-repressors combined with expression cassettes have been described in the incorporated US 2006/0172382 (e.g., paragraphs [0129]-[0131]).

In certain embodiments, transcription units or expression cassettes of the invention are provided, further comprising a transcription pause (TRAP) sequence, essentially as described in paragraph [0132] of the incorporated US 2006/0172382. One non-limiting example of a TRAP sequence is given in SEQ ID NO: 81. Examples of other TRAP sequences, methods to find these, and uses thereof have been described in US 2006/0010506.

DNA molecules comprising multicistronic transcription units and/or expression cassettes according to the invention can be used for improving expression of nucleic acid, preferably in host cells. The terms "cell"/"host cell" and "cell line"/"host cell line" are respectively typically defined as a cell and homogeneous populations thereof that can be maintained in cell culture by methods known in the art, and that have the ability to express heterologous or homologous proteins.

Several exemplary host cells that can be used have been described in the incorporated US 2006/0172382 (e.g., paragraphs [0133]-[0136]), and such cells include for instance mammalian cells, including but not limited to CHO cells, e.g., CHO-K1, CHO-S, CHO-DG44, CHO-DUKXB11, including CHO cells having a DHFR⁻ phenotype, as well as myeloma cells (e.g., Sp2/0, NS0), HEK 293 cells, and PER.C6 cells.

Such eukaryotic host cells can express desired polypeptides, and are often used for that purpose. They can be obtained by introduction of a DNA molecule of the invention, preferably in the form of an expression cassette, into the cells. In certain embodiments, the expression cassette is integrated in the genome of the host cells, which can be in different positions in various host cells, and selection will provide for a clone where the transgene is integrated in a suitable position, leading to a host cell clone with desired properties in terms of expression levels, stability, growth characteristics, and the like. Alternatively the multicistronic transcription unit may be targeted or randomly selected for integration into a chromosomal region that is transcriptionally active, e.g., behind a promoter present in the genome. Selection for cells containing the DNA of the invention can be performed by selecting for the selectable marker polypeptide, using routine methods known by the person skilled in the art. When such a multicistronic transcription unit is integrated behind a promoter in the genome, an expression cassette of the invention can be generated in situ, i.e., within the genome of the host cells.

Preferably the host cells are from a stable clone that can be selected and propagated according to standard procedures known to the person skilled in the art. A culture of such a clone is capable of producing polypeptide of interest, if the cells comprise the multicistronic transcription unit of the invention.

Introduction of nucleic acid that is to be expressed in a cell, can be done by one of several methods, which as such are known to the person skilled in the art, also dependent on the format of the nucleic acid to be introduced. The methods include but are not limited to transfection, infection, injection, transformation, and the like. Suitable host cells that express the polypeptide of interest can be obtained by selection.

In certain embodiments, the DNA molecule comprising the multicistronic transcription unit of the invention, preferably in the form of an expression cassette, is integrated into the genome of the eukaryotic host cell of the invention. This will provide for stable inheritance of the multicistronic transcription unit.

Selection for the presence of the selectable marker polypeptide, and hence for expression, can be performed during the initial obtaining of the cells. In certain embodiments, selection agent is present in the culture medium at least part of the time during the culturing, either in sufficient concentrations to select for cells expressing the selectable marker polypeptide or in lower concentrations. In certain embodiments, selection agent is no longer present in the culture medium during the production phase when the polypeptide is expressed.

A "polypeptide of interest" can be any peptide or protein, and may be a monomeric protein or a (part of a) multimeric protein. A multimeric protein comprises at least two polypeptide chains. Non-limiting examples of a protein of interest of the invention are enzymes, hormones, immunoglobulin chains, therapeutic proteins like anti-cancer proteins, blood coagulation proteins such as Factor VIII, multi-functional proteins, such as erythropoietin, diagnostic proteins, or proteins or fragments thereof useful for vaccination purposes, all known to the person skilled in the art.

In certain embodiments, an expression cassette of the invention encodes an immunoglobulin heavy or light chain or an antigen binding part, derivative and/or analogue thereof. In certain embodiments, a protein expression unit of the invention is provided, wherein the protein of interest is an immunoglobulin heavy chain. In yet other embodiments, a protein expression unit of the invention is provided, wherein the protein of interest is an immunoglobulin light chain. When these two protein expression units are present within the same (host) cell a multimeric protein and more specifically an immunoglobulin, is assembled. Hence, in certain embodiments, the protein of interest is an immunoglobulin, such as an antibody, which is a multimeric protein. In certain embodiments, such an antibody is a human or humanized antibody. In certain embodiments thereof, it is an IgG, IgA, or IgM antibody. An immunoglobulin may be encoded by the heavy and light chains on different expression cassettes, or on a single expression cassette. In certain embodiments, the heavy and light chain are each present on a separate expression cassette, each having its own promoter (which may be the same or different for the two expression cassettes), each comprising a multicistronic transcription unit of the invention, the heavy and light chain being the polypeptide of interest, and preferably each coding for a different selectable marker protein, so that selection for both heavy and light chain expression cassette can be performed when the expression cassettes are introduced and/or present in a eukaryotic host cell.

The polypeptide of interest may be from any source, and in certain embodiments is a mammalian (e.g., human) protein or an artificial protein (e.g., a fusion protein or mutated protein).

The configurations of the expression cassettes of the invention may also be used when the ultimate goal is not the production of a polypeptide of interest, but the RNA itself, for instance for producing increased quantities of RNA from an expression cassette, which may be used for purposes of regulating other genes (e.g., RNAi, antisense RNA), gene therapy, in vitro protein production, etc.

In certain aspects, provided are methods for generating a host cell expressing a polypeptide of interest, the method comprising introducing into a plurality of precursor cells a DNA molecule or an expression cassette of the invention, culturing the generated cells under selection conditions and selecting at least one host cell producing the polypeptide of interest. Advantages of this novel method are similar to those described for the alternative method disclosed in the incorporated US 2006/0172382 (e.g., paragraphs [0145]-[0147]).

While clones having relatively low copy numbers of the multicistronic transcription units and high expression levels can be obtained, the selection system of the invention nevertheless can be combined with amplification methods to even further improve expression levels. This can for instance be accomplished by amplification of a co-integrated dhfr gene using methotrexate, for instance by placing dhjfr on the same nucleic acid molecule as the multicistronic transcription unit of the invention, or by cotransfection when dhfr is on a separate DNA molecule. The dhfr gene can also be part of a multicistronic expression unit.

Also provided are methods for producing one or more polypeptides of interest, the method comprising culturing host cells of the invention.

Culturing a cell is done to enable it to metabolize, and/or grow and/or divide and/or produce recombinant proteins of interest. This can be accomplished by methods well known to persons skilled in the art, and includes but is not limited to providing nutrients for the cell. The methods comprise growth adhering to surfaces, growth in suspension, or combinations thereof. Culturing can be done for instance in dishes, roller bottles or in bioreactors, using batch, fed-batch, continuous systems such as perfusion systems, and the like. In order to achieve large scale (continuous) production of recombinant proteins through cell culture it is preferred in the art to have cells capable of growing in suspension, and it is preferred to have cells capable of being cultured in the absence of animal- or human-derived serum or animal- or human-derived serum components.

The conditions for growing or multiplying cells (see, e.g., Tissue Culture, Academic Press, Kruse and Paterson, editors (1973)) and the conditions for expression of the recombinant product are known to the person skilled in the art. In general, principles, protocols, and practical techniques for maximizing the productivity of mammalian cell cultures can be found in Mammalian Cell Biotechnology: a Practical Approach (M. Butler, ed., IRL Press, 1991).

In certain embodiments, the expressed protein is collected (isolated), either from the cells or from the culture medium or from both. It may then be further purified using known methods, e.g., filtration, column chromatography, etc., by methods generally known to the person skilled in the art.

The selection method works in the absence of chromatin control elements, but improved results are obtained when the multicistronic expression units are provided with such elements. The selection method works particularly well when an expression cassette of the invention, comprising at least one anti-repressor sequence is used. Depending on the selection agent and conditions, the selection can in certain cases be made so stringent, that only very few or even no host cells survive the selection, unless anti-repressor sequences are present. Hence, the combination of the novel selection method and anti-repressor sequences provides a very attractive method to obtain only limited numbers of colonies with a greatly improved chance of high expression of the polypeptide of interest therein, while at the same time the obtained clones comprising the expression cassettes with anti-repressor sequences provide for stable expression of the polypeptide of interest, i.e., they are less prone to silencing or other mechanisms of lowering expression than conventional expression cassettes.

In certain aspects, provided is a multicistronic transcription unit having an alternative configuration compared to the configuration disclosed in US 2006/0172382: in the alternative configuration of the invention, the sequence coding for the polypeptide of interest is upstream of the sequence coding for the selectable marker polypeptide, and the selectable marker polypeptide is operably linked to a cap-independent translation initiation sequence, preferably an internal ribosome entry site (IRES). Such multicistronic transcription units as such were known (e.g., Rees et al., 1996, US 2005/0191723), but had not been combined with a non-ATG start codon. According to the alternative of the invention, the start codon of the selectable marker polypeptide is changed into a non-ATG start codon, to further decrease the translation initiation rate for the selectable marker. This therefore leads to a desired decreased level of expression of the selectable marker polypeptide, and can result in highly effective selection host cells expressing high levels of the polypeptide of interest, as with the embodiments disclosed in US 2006/0172382. One potential advantage of this alternative aspect of the invention, compared to the embodiments outlined in US 2006/0172382, is that the coding sequence of the selectable marker polypeptide needs no further modification of internal ATG sequences, because any internal ATG sequences therein can remain intact since they are no longer relevant for translation of further downstream polypeptides. This may be especially advantageous if the coding sequence for the selectable marker polypeptide contains several internal ATG sequences, because the task of changing these and testing the resulting construct for functionality does not have to be performed for the invention: only mutation of the ATG start codon suffices in this case. It is shown herein that this alternative provided by the invention also leads to very good results.

The coding sequence for the selectable marker polypeptide in the DNA molecules of the invention is under translational control of the IRES, whereas the coding sequence for the protein of interest is preferably translated in a cap-dependent manner. The coding sequence for the polypeptide of interest comprises a stop codon, so that translation of the first cistron ends upstream of the IRES, which IRES is operably linked to the second cistron.

As will be readily apparent to the skilled person after reading the present disclosure, most parts of these multicistronic expression units can be advantageously varied along the same lines as for the multicistronic expression units having an opposite order of the coding sequences for the polypeptide of interest and the selectable marker polypeptide (i.e., the multicistronic transcription units of the incorporated US 2006/0172382). For instance, the preferred start codons for the selectable marker polypeptide, the incorporation into expression cassettes, the host cells, the promoters, the presence of chromatin control elements, etc. can be varied and used in certain embodiments as described supra. Also the use of these multicistronic expression units and expression cassettes is as described supra. Therefore, this aspect is really an alternative to the means and methods described in incorporated US 2006/0172382, with the main difference being that the order of the polypeptides in the multicistronic expression units is reversed, and that an IRES is now required for the translation of the selectable marker polypeptide.

As used herein, an "internal ribosome entry site" or "IRES" refers to an element that promotes direct internal ribosome entry to the initiation codon, such as normally an ATG, but in this invention preferably GTG or TTG, of a cistron (a protein encoding region), thereby leading to the cap-independent translation of the gene. See, e.g., Jackson R J, Howell M T, Kaminski A (1990) Trends Biochem Sci 15 (12): 477-83) and Jackson R J and Kaminski, A. (1995) RNA 1 (10): 985-1000. The invention encompasses the use of any cap-independent translation initiation sequence, in particular any IRES element that is able to promote direct internal ribosome entry to the initiation codon of a cistron. "Under translational control of an IRES" as used herein means that translation is associated with the IRES and proceeds in a cap-independent manner. As used herein, the term "IRES" encompasses functional variations of IRES sequences as long as the variation is able to promote direct internal ribosome entry to the initiation codon of a cistron. As used herein, "cistron" refers to a polynucleotide sequence, or gene, of a protein, polypeptide, or peptide of interest. "Operably linked" refers to a situation where the components described are in a relationship permitting them to function in their intended manner. Thus, for example, a promoter "operably linked" to a cistron is ligated in such a manner that expression of the cistron is achieved under conditions compatible with the promoter. Similarly, a nucleotide sequence of an IRES operably linked to a cistron is ligated in such a manner that translation of the cistron is achieved under conditions compatible with the IRES.

Internal ribosome binding site elements are known from viral and mammalian genes (Martinez-Salas, 1999), and have also been identified in screens of small synthetic oligonucleotides (Venkatesan & Dasgupta, 2001). The IRES from the encephalomyocarditis virus has been analyzed in detail (Mizuguchi et al., 2000). An IRES is an element encoded in DNA that results in a structure in the transcribed RNA at which eukaryotic ribosomes can bind and initiate translation. An IRES permits two or more proteins to be produced from a single RNA molecule (the first protein is translated by ribosomes that bind the RNA at the cap structure of its 5' terminus, (Martinez-Salas, 1999)). Translation of proteins from IRES elements is less efficient than cap-dependent translation: the amount of protein from IRES-dependent open reading frames (ORFs) ranges from less than 20% to 50% of the amount from the first ORF (Mizuguchi et al., 2000). The reduced efficiency of IRES-dependent translation provides an advantage that is exploited by this embodiment of the current invention. Furthermore, mutation of IRES elements can attenuate their activity, and lower the expression from the IRES-dependent ORFs to below 10% of the first ORF (Lopez de Quinto & Martinez-Salas, 1998, Rees et al., 1996). It is therefore clear to a person skilled in the art that changes to the IRES can be made without altering the essence of the function of the IRES (hence, providing a protein translation initiation site with a reduced translation efficiency), resulting in a modified IRES. Use of a modified IRES which is still capable of providing a small percentage of translation (compared to a 5' cap translation) is therefore also included in this invention. Non-ATG start codons are used to significantly further reduce translation initiation of the selectable marker ORF, therewith further improving the chances of obtaining a preferred host cell, i.e., a host cell expressing high levels of recombinant protein of interest.

U.S. Pat. Nos. 5,648,267 and 5,733,779 describe the use of a dominant selectable marker sequence with an impaired consensus Kozak sequence ([Py]xxATG[Py], wherein [Py] is a pyrimidine nucleotide (i.e., C or T), x is a nucleotide (i.e., G, A, T, or C), and the ATG start codon is underlined). U.S. Pat. No. 6,107,477 describes the use of a non-optimal Kozak sequence (AGATCTTTATGGACC, wherein the ATG start codon is underlined) for a selectable marker gene. None of these patents describes the use of a non-ATG start codon, nor provides any suggestion to do so. Furthermore they are silent on combinations with an IRES. Moreover, since an IRES in itself already has reduced translation initiation compared to cap-dependent translation, it could not be foreseen prior to the invention whether the combination of an IRES with a non-ATG start codon for the selectable marker could provide sufficient translation of the selectable marker polypeptide to give any selectable levels thereof. The invention shows that this is the case, and provides surprisingly efficient selection systems.

Also provided is a DNA molecule comprising a sequence coding for a selectable marker polypeptide operably linked to an IRES sequence, wherein the coding sequence coding for the selectable marker polypeptide comprises a translation start sequence selected from the group consisting of: a) a GTG start codon; b) a TTG start codon; c) a CTG start codon; d) a ATT start codon; and e) a ACG start codon.

The skilled person will understand that further modifications of the invention are possible, e.g., those given in US 2006/0195935, incorporated by reference herein, particularly Examples 20-27 thereof.

In certain embodiments, the mammalian 5,6,7,8 tetrahydrofolate synthesizing enzyme dihydrofolate reductase (DHFR) can be used as a selection marker in cells that have a DHFR$^-$ phenotype (e.g., CHO-DG44 cells), by omitting hypoxanthine and thymidine (and preferably also glycine) from the culture medium and including folate (or (dihydro) folic acid) into the culture medium (Simonsen et al., 1988). The dhfr gene can, for instance, be derived from the mouse genome or mouse cDNA and can be used of the invention, preferably by providing it with a GTG or TTG start codon (see, SEQ ID NO: 73 for the sequence of the dhfr gene). In these embodiments, by 'omitting from the culture medium' is meant that the culture medium has to be essentially devoid of the indicated component(s), meaning that there is insufficient of the indicated component present to sustain growth of the cells in the culture medium, so that a good selection is possible when the genetic information for the indicated enzyme is expressed in the cells and the indicated precursor component is present in the culture medium. For instance, the indicated component is present at a concentration of less than 0.1% of the concentration of that component that is normally used in the culture medium for a certain cell type. In certain embodiments, the indicated component is absent from the culture medium. A culture medium lacking the indicated component can be prepared according to standard methods by the skilled person or can be obtained from commercial media suppliers. A potential advantage of the use of these types of metabolic enzymes as selectable marker polypeptides is that they can be used to keep the multicistronic transcription units under continuous selection, which may result in higher expression of the polypeptide of interest.

In another aspect, the invention uses the DHFR metabolic selection marker as an additional selection marker in a multicistronic transcription unit of the invention. In such embodiments, selection of host cell clones with high expression is first established by use of for instance an antibiotic selection marker, e.g., ZEOCIN™, neomycin, etc., the coding sequences of which will have a GTG or TTG start codon of the invention. After the selection of suitable clones, the antibiotic selection is discontinued, and now continuous or intermittent selection using the metabolic enzyme selection marker can be performed by culturing the cells in the medium lacking the appropriate identified components described supra and containing the appropriate precursor components described supra. In this aspect, the metabolic selection marker is operably linked to an IRES, and can have its normal ATG content, and the start codon can be suitably chosen from GTG or TTG. The multicistronic transcription units in this aspect are at least tricistronic.

The practice of this invention will employ, unless otherwise indicated, conventional techniques of immunology, molecular biology, microbiology, cell biology, and recombinant DNA, which are within the skill of the art. See e.g., Sambrook, Fritsch and Maniatis, Molecular Cloning: A Laboratory Manual, 2$^{nd}$ edition, 1989; Current Protocols in Molecular Biology, Ausubel F M, et al., eds, 1987; the series Methods in Enzymology (Academic Press, Inc.); PCR2: A Practical Approach, MacPherson M J, Hams B D, Taylor G R, eds, 1995; Antibodies: A Laboratory Manual, Harlow and Lane, eds, 1988.

The invention is further described by the following illustrative Examples. The Examples do not limit the invention in any way. They merely serve to clarify the invention.

EXAMPLES

Example 1 describes the selection system with the multicistronic transcription unit of the invention, and it will be clear that the variations described in Examples 8-26 of the incorporated US 2006/0172382, can also be applied and tested for the multicistronic transcription units of the present application. The same holds for those of Examples 20-27 of the incorporated US 2006/0195935.

Example 1

Stringent Selection by Placing a Modified ZEOCIN™ Resistance Gene Behind an IRES Sequence Examples 8-26 of US 2006/0172382 have shown a selection system where a sequence encoding a selectable marker protein is upstream of a sequence encoding a protein of interest in a multicistonic transcription unit, and wherein the translation initiation sequence of the selectable marker is non-optimal, and wherein further internal ATGs have been removed from the selectable marker coding sequence. This system results in a high stringency selection system. For instance the Zeo selection marker wherein the translation initiation codon is changed into TTG was shown to give very high selection stringency, and very high levels of expression of the protein of interest encoded downstream.

In another possible selection system (i.e., the system of the invention) the selection marker, e.g., Zeo, is placed downstream from an IRES sequence. This creates a multicistronic mRNA from which the Zeo gene product is translated by IRES-dependent initiation. In the usual d2EGFP-IRES-Zeo construct (i.e., a construct of the prior art, e.g., WO 2006/005718), the Zeo start codon is the optimal ATG. We tested whether changing the Zeo ATG start codon into for instance TTG (referred to as IRES-TTG Zeo) results in increased selection stringencies compared to the usual IRES-ATG Zeo.

Results

The used constructs are schematically shown in FIG. 1. The control construct consisted of a CMV promoter, the d2EGFP gene, an IRES sequence (the sequence of the used IRES (Rees et al., 1996) in this example was: GCCCCTCTC-CCTCCCCCCCCCCCTAACGTTACTGGC-CGAAGCCGCTTGGAATAAGGCC GGTGT-GCGTTTGTCTATATGTGATTTTCCACCATATTGCCGT CTTTTGGCAATGTGAG GGCCCGGAAACCTGGC-CCTGTCTTCTTGACGAGCATTC-CTAGGGGTCTTTCCCCTCTC GCCAAAGGAATG-CAAGGTCTGTTGAATGTCGTGAAGGAAGCAGTTCC TCTGGAAGC TTCTTGAAGACAAACAACGTCTG-TAGCGACCCTTTGCAGGCAGCGGAACCCCCCACC TGGCGACAGGTGCCTCTGCGGC-CAAAAGCCACGTGTATAAGATACACCTGCAAAGG CGGCACAACCCCAGTGCCACGTTGT-GAGTTGGATAGTTGTGGAAAGAGTCAAATGG CTCTCCTCAAGCGTATTCAA-CAAGGGCTGAAGGATGCCCAGAAGG-TACCCCATTGT ATGGGATCTGATCTGGGGCCTCG-GTGCACATGCTTTACATGTGTTTAGTCGAGGTTA AAAAAACGTCTAGGCCCCCCGAAC-CACGGGGACGTGGTTTTCCTTTGAAAAACACG ATGATAAGCTTGCCACAACCCCGGGATA; SEQ ID NO: 82), and a TTG Zeo selection marker, i.e., the ZEOCIN™ resistance gene with a TTG start codon ('d2EGFP-IRES-TTG Zeo'). The other construct was the same, but with a combination of STAR 7 and STAR 67 placed upstream of the expression cassette and STAR 7 downstream of the cassette ('STAR7/67 d2EGFP-IRES-TTG Zeo STAR7'). Both constructs were transfected to CHO-K1 cells and selection was performed with 100 µg/ml ZEOCIN™ in the culture medium. Four colonies emerged after transfection with the control construct and six with the STAR containing construct. These independent colonies were isolated propagated before analysis of d2EGFP expression levels. As shown in FIG. 1, incorporation of STAR elements in the construct resulted in the formation of colonies with high d2EGFP expression levels. Of the control colonies without STAR elements ('d2EGFP-IRES-TTG Zeo') only one colony displayed some d2EGFP expression. The expression levels are also much higher than those obtained with other control constructs, containing the IRES with a normal Zeo with standard ATG start codon, either with or without STAR elements ('d2EGFP-IRES-ATG Zeo' and 'STAR 7/67 d2EGFP-IRES-ATG Zeo STAR7'; also in these ATG Zeo constructs there was an enhancing effect of the STAR elements, but these are modest as compared to the novel TTG Zeo variant).

These results show that placing a Zeo selection marker with a TTG start codon downstream of an IRES sequence, in combination with STAR elements, operates well and establishes a stringent selection system.

From these data and Examples 8-26 of US 2006/0172382 and 20-27 of US 2006/0195935, it will be clear that the marker can be varied along the same lines of Examples 8-26 of US 2006/0172382 and 20-27 of US 2006/0195935. For instance, instead of a TTG start codon, a GTG start codon can be used, and the marker can be changed from Zeo into a different marker, e.g., Neo, Blas, DHFR, puro, etc., all with either GTG or TTG as start codon. The STAR elements can be varied by using different STAR sequences or different placement thereof, or by substituting them for other chromatin control elements, e.g., MAR sequences. This leads to improvements over the prior art selection systems having an IRES with a marker with a normal ATG start codon.

As a non-limiting example, instead of the modified Zeo resistance gene (TTG Zeo) a modified Neomycin resistance gene is placed downstream of an IRES sequence. The modification consists of a replacement of the ATG translation initiation codon of the Neo coding sequence by a TTG translation initiation codon, creating TTG Neo. The CMV-d2EGF-IRES-TTG Neo construct, either surrounded by STAR elements or not, is transfected to CHO-K1 cells. Colonies are picked, cells are propagated and d2EGFP values are measured. This ('IRES-TTG Neo') leads to improvement over the known selection system having Neo with an ATG start codon downstream of an IRES ('IRES-ATG Neo'). The improvement is especially apparent when the TTG Neo construct comprises STAR elements.

Example 2

Stability of Expression by Placing a Modified dhfr Gene Behind an IRES Sequence

Modification of the translation initiation codon of the ZEOCIN™ selection marker to a translation initiation codon that is used much less frequently than the usual ATG codon, results in a high stringency selection system. In the described selection system of US 2006/0172382, the TTG Zeo is placed upstream of the gene of interest. In another possible selection system the Zeo selection marker was placed downstream of an IRES sequence (present application, see example 1). This creates a bicistronic mRNA from which the Zeo gene product is translated from translation initiation codons in the IRES sequence.

Figure 2:
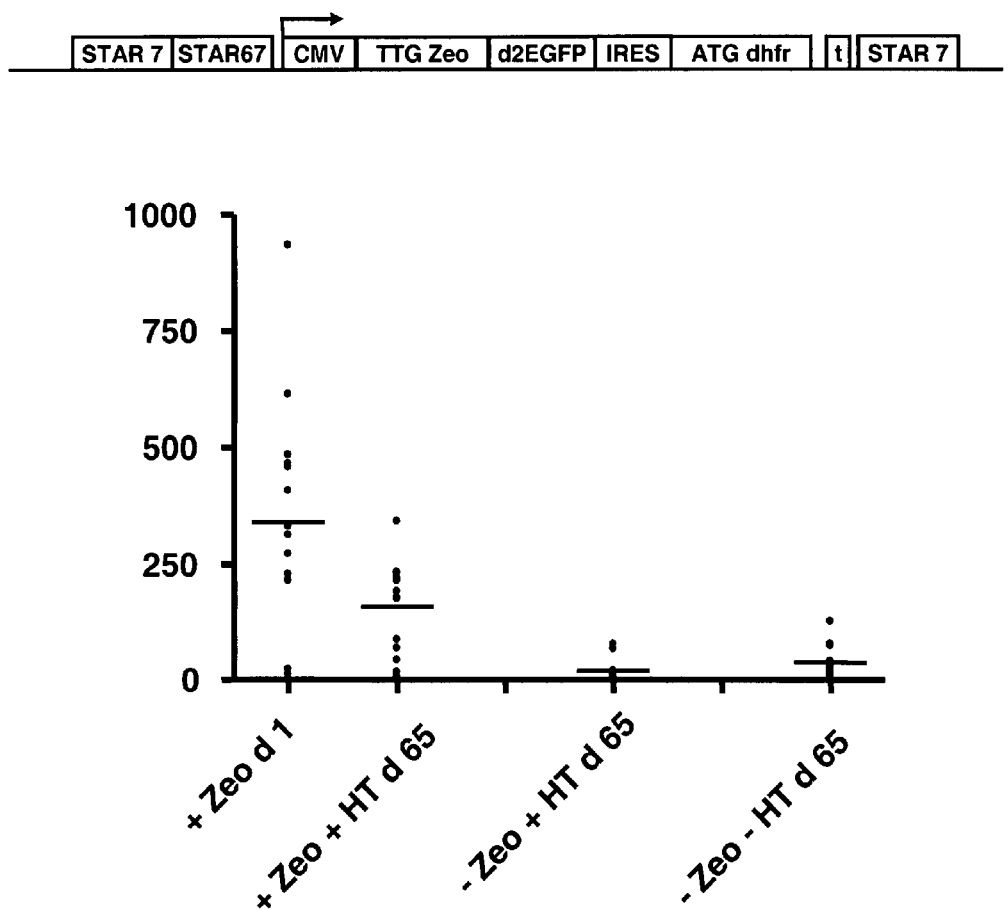
FIG. 2. Results with tricistronic expression cassettes with DHFR as maintenance marker. The expression construct contains a ZEOCIN™ selectable marker gene with a TTG start codon and lacking internal ATG sequences upstream of the sequence encoding the polypeptide of interest (exemplified here by d2EGFP), which is further operably linked via an IRES to a downstream metabolic selection marker dhfr gene (with an ATG start codon). Dots indicate individual data points (GFP fluorescence signal in $Zeo^R$ colonies on vertical axis), lines indicate the average expression levels. The used construct is shown above the graph, conditions are indicated on the horizontal axis (d: day). See Example 2 for details.

In this experiment, embodiments of these two systems were combined. We placed a TTG selection marker upstream of the reporter gene and coupled a GTG or TTG modified metabolic marker with an IRES to the reporter gene. Different selection marker genes can be used, such as the ZEOCIN™ and neomycin resistance genes, as well as the dhfr gene. Here we placed a modified ZEOCIN™ resistance gene, TTG Zeo (see, US 2006/0172382), upstream of a gene of interest and the DHFR selection gene downstream of the gene of interest, coupled by an IRES (FIG. 2). The objective of this expression cassette was to select a mammalian cell clone producing high level of protein, first by selection on ZEOCIN™. The TTG Zeo-gene of interest configuration most effectively achieves this objective. After this initial selection phase, the characteristics of the DHFR-protein are employed to achieve maintenance of the high expression levels in the absence of the ZEOCIN™ antibiotic.

Active selection pressure appears beneficial to keep the protein expression levels in a TTG Zeo selected colony at the same high level over a prolonged period of time. This can for instance be accomplished by keeping a minimal amount of ZEOCIN™ in the culture medium, but this is not favoured in industrial settings for economic and potentially for regulatory purposes (ZEOCIN™ is both toxic and expensive).

Another approach is to couple the gene of interest to a selection marker that is an enzyme that metabolizes one or more essential steps in a metabolic pathway. With essential is meant that the cell is not able to synthesize specific essential metabolic building blocks itself, implying that these building blocks have to be present in the culture medium in order to allow the cell to survive. Well-known examples are the essential amino acids that cannot be synthesized by a mammalian cell and that need to be present in the culture medium to allow the cell to survive. Another example is related to the 5,6,7,8-tetrahydrofolate synthesizing dhfr gene. The corresponding DHFR protein is an enzyme in the folate pathway. The DHFR protein specifically converts folate into 5,6,7,8-tetrahydrofolate, a methyl group shuttle required for the de novo synthesis of purines (hypoxanthine), thymidylic acid (thymidine), and the amino acid Glycine. To operate, the non-toxic substance folate has to be present in the culture medium (Urlaub et al., 1980). Furthermore, the medium has to lack hypoxanthine and thymidine, since when these are available for the cell, the need for the DHFR enzyme is bypassed. CHO-DG44 cells lack the dhfr gene and these cells therefore need glycine, hypoxanthine and thymidine in the culture medium to survive. If, however, the end-products glycine, hypoxanthine and thymidine are absent from the culture medium and folate is present, and the dhfr gene is provided because it is present on an expression cassette in the cell, the cell can convert folate into 5,6,7,8-tetrahydrofolate, and can thus survive in this culture medium. This principle has been used for many years as selection methodology to create stably transfected mammalian cell lines.

Here, we use this principle, not to select the stable clones initially (this is done with ZEOCIN™), but to keep the cells under metabolic selection pressure. The advantage is that initial very high protein expression can be achieved through the TTG Zeo selection system, and that these high expression levels can be maintained, without the need to keep ZEOCIN™ in the culture medium. Instead, ZEOCIN™ can be omitted from the medium and the absence of glycine, hypoxantine and thymidine (GHT) or just hypoxantine and thymidine (HT) from the culture medium is sufficient to keep the selection pressure high enough to warrant high protein expression levels. Such a configuration requires the presence of two selection markers, both the ZEOCIN™ resistance gene and the dhfr gene need to be present on the expression cassette. As outlined above this is efficiently achieved when both genes are present with the gene of interest in such a configuration that a tricistronic mRNA is transcribed faun a single promoter. When the modified ZEOCIN™ resistance gene (TTG Zeo) is employed upstream of the d2EGFP gene, the dhfr gene is downstream coupled to the d2EGFP gene, for instance, through an IRES sequence (FIG. 2).

Results

We made constructs in which the TTG Zeo selection marker was placed upstream of the d2EGFP reporter gene and the DHFR selection marker downstream of the d2EGFP gene, coupled through an IRES sequence (FIG. 2). These constructs were flanked with STARs 7/67/7. Three versions of these constructs were made: ATG DHFR, GTG DHFR or TTG DHFR, each name indicating the start codon used for the dhfr gene. The constructs were transfected to CHO-DG44 cells. DNA was transfected using Lipofectamine 2000 (Invitrogen) and cells were grown in the presence of 400 µg/ml ZEOCIN™ in IMDM medium (Gibco)+10% FBS (Gibco)+HT-supplement.

The average d2EGFP value in 14 TTG Zeo IRES ATG DHFR clones was 341 (day 1), when measured in the presence of 400 µg/ml ZEOCIN™ (FIG. 2). After these measurements the cells were split and further cultured under three conditions:
(1) with 400 µg/ml ZEOCIN™ and with hypoxanthine and thymidine (HT-supplement) in the medium,
(2) without ZEOCIN™, but with HT-supplement in the medium,
(3) without ZEOCIN™ and without HT-supplement.

In summary, in condition 1, the cells are under ZEOCIN™ selection pressure only, in condition 2 the cells are NOT under any selection pressure and in condition 3 the cells remain under DHFR selection pressure. The latter condition 3 requires continuous expression of the dhfr gene to allow expression of the DHFR protein and cell survival as a result.

After 65 days, we again measured the d2EGFP values. The average d2EGFP value in the TTG Zeo IRES <u>ATG</u> DHFR clones under ZEOCIN™ selection was now 159 (FIG. 2). The average d2EGFP value in the TTG Zeo IRES ATG DHFR clones without ZEOCIN™ and with HT supplement was 20 (FIG. 2). The average d2EGFP value in the TTG Zeo IRES ATG DHFR clones without ZEOCIN™ selection and without HT supplement was 37 (FIG. 2). Overall we thus observed a drop in d2EGFP values, but the most severe in the absence of ZEOCIN™, irrespective whether HT supplement was present or not.

Figure 3:
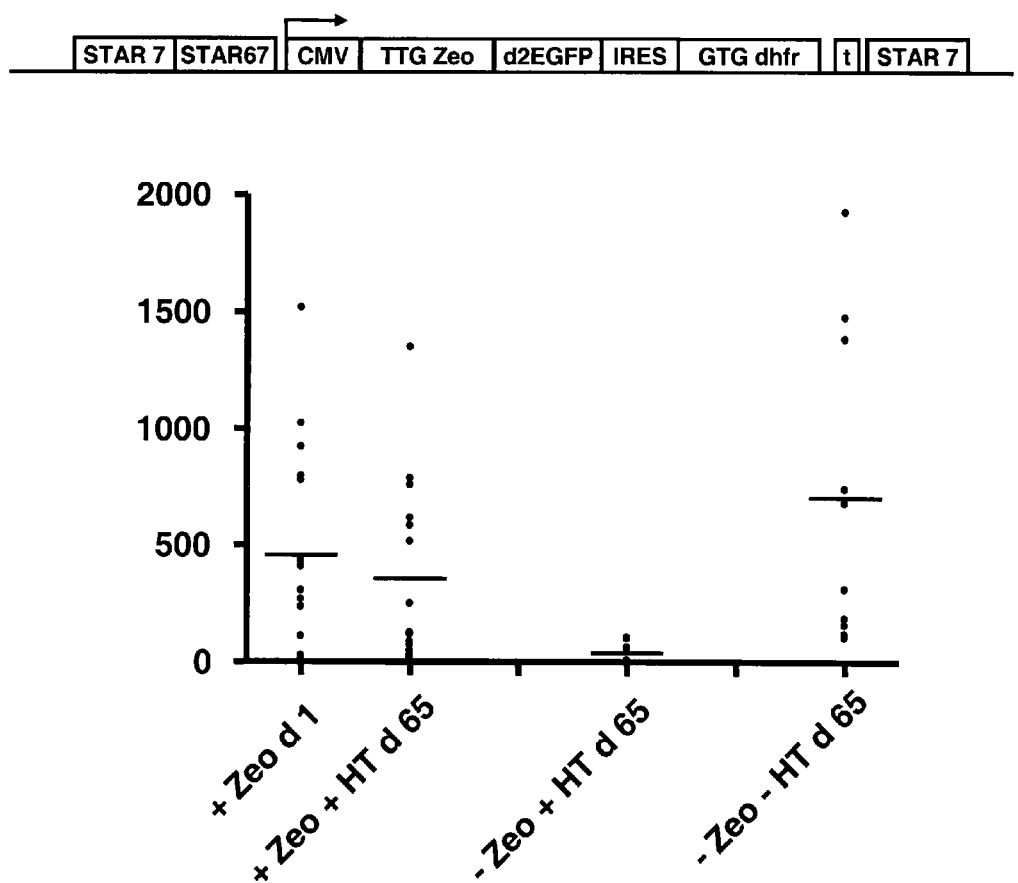
FIG. 3. As FIG. 2, but with dhfr gene having GTG start codon.

We followed the same protocol with the TTG Zeo IRES <u>GTG</u> DHFR construct. The average d2EGFP value in 15 TTG Zeo IRES GTG DHFR clones was 455 (day 1), when measured in the presence of 400 µg/ml ZEOCIN™ (FIG. 3). After these measurements the cells were split and further cultured under the above described three conditions. After 65 days we again measured the d2EGFP values. The average d2EGFP value in the TTG Zeo IRES GTG DHFR clones under ZEOCIN™ selection was now 356 (FIG. 3). The average d2EGFP value in the TTG Zeo IRES GTG DHFR clones without ZEOCIN™ selection and with HT supplement was 39 (FIG. 3). The average d2EGFP value in the TTG Zeo IRES GTG DHFR clones without ZEOCIN™ selection and without HT supplement was 705 (FIG. 3).

In this case, we observed a drop in d2EGFP values only in the absence of ZEOCIN™ and in the presence of HT supplement (condition 2). In the absence of ZEOCIN™, but in the absence of also HT supplement the d2EGFP values became actually significantly higher (condition 3). This may indicate that the expression levels of the DHFR protein, due to the impaired translation frequency of the GTG DHFR mRNA is low enough to provide very high selection stringency. This selection pressure, in the absence of any toxic agents, is high enough to maintain high protein expression levels over time, and apparently even improves these expression levels over time.

Figure 4:
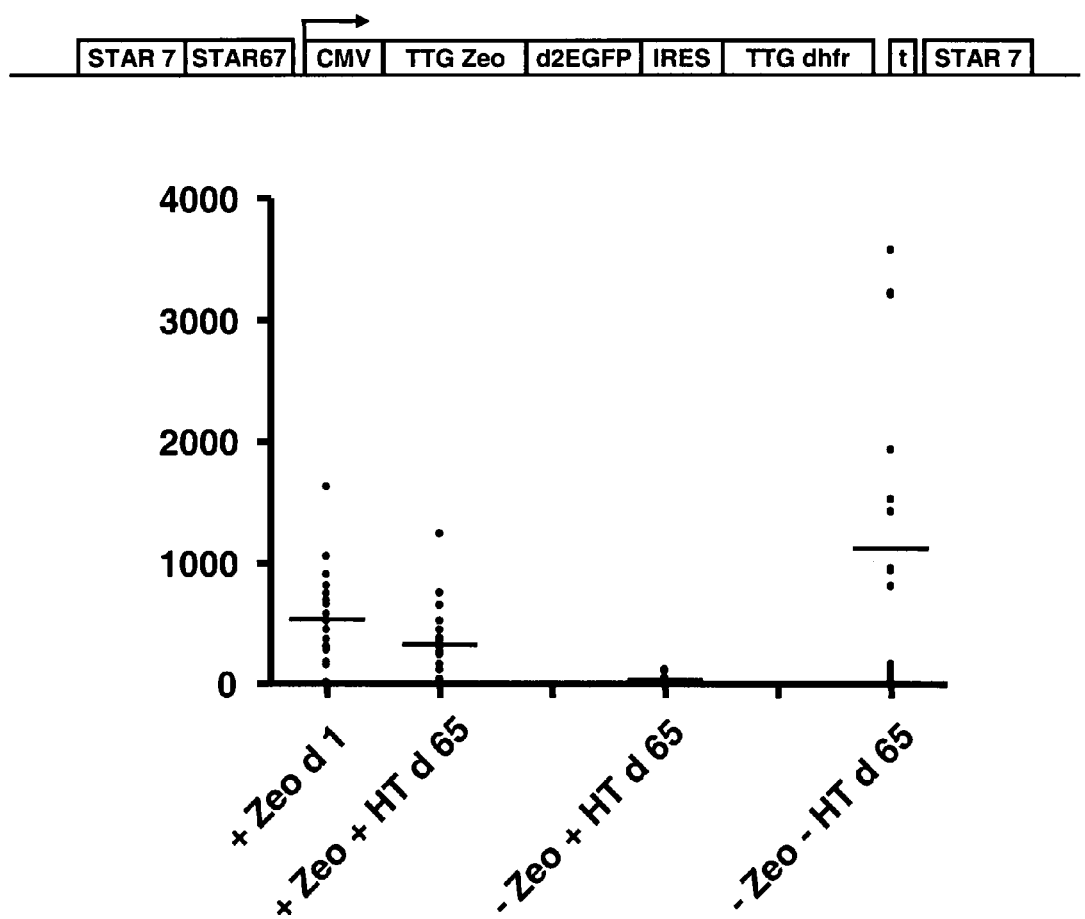
FIG. 4. As FIG. 2, but with dhfr gene having TTG start codon.

We did the same for the TTG Zeo IRES <u>TTG</u> DHFR construct. The average d2EGFP value in 18 TTG Zeo IRES TTG DHFR clones was 531 (day 1), when measured in the presence of 400 µg/ml ZEOCIN™ (FIG. 4). After these measurements the cells were split and further cultured under the above described three conditions. After 65 days we again measured the d2EGFP values. The average d2EGFP value in the TTG Zeo IRES TTG DHFR clones under ZEOCIN™ selection was now 324 (FIG. 4). The average d2EGFP value in the TTG Zeo IRES TTG DHFR clones without ZEOCIN™ selection and in the presence of HT supplement was 33 (FIG. 4). The average d2EGFP value in the TTG Zeo IRES TTG DHFR clones without ZEOCIN™ selection and without HT supplement was 1124 (FIG. 4).

Again, we observed a drop in d2EGFP values only in the absence of ZEOCIN™ and in the presence of HT supplement (condition 2). In the absence of ZEOCIN™, but in the absence of HT supplement the d2EGFP values became even higher than with the TTG Zeo IRES GTG DHFR construct (condition 3). Since the TTG variant is more stringent than the GTG variant, it is expected that even less DHFR protein will be translated with the TTG DHFR than with the GTG DHFR variant. The increased selection pressure, in the absence of any toxic agents, with the TTG DHFR variant is high enough to maintain high protein expression levels over time, and apparently also even further improves protein expression levels over time.

The data show that coupling a non-ATG start codon-variant of the dhfr gene through an IRES to the d2EGFP gene allows a high degree of stability of high d2EGFP expression in CHO-DG44 cells. This occurs in culture medium without ZEOCIN™ and without essential metabolic end products. Prior selection on ZEOCIN™ through the modified TTG Zeo selection marker allows the efficient establishment of colonies with high d2EGFP expression levels. Now just a simple change of culture medium (removing ZEOCIN™ and HT) is required to maintain the high d2EGFP expression levels, and even improve these expression levels.

Example 3

Increased Expression by Placing a Modified dhfr Gene Behind an IRES Sequence is not the Result of Gene Amplification Use of the dhfr gene as a selection marker in the prior art often relied on amplification of the dhfr gene. A toxic agent, methotrexate was used in such systems to amplify the dhfr gene, and concomitantly therewith the desired transgene, of which up to many thousands of copies could be found integrated into the genome of CHO cells after such amplification. Although these high copy numbers lead to high expression levels, they are also considered disadvantageous because so many copies can lead to increased genomic instability, and further removing methotrexate from the culture medium leads to rapid removal of many of the amplified loci.

In Example 2, no methotrexate was used to inhibit the DHFR enzyme activity. Only the hypoxanthine and thymidine precursor were removed from the culture medium, and this was sufficient to achieve both stability of protein expression, and even increased expression levels. We therefore determined whether the employment of the DHFR enzyme in our setting resulted in gene amplification.

Results

We isolated DNA from the clones that were described in Example 2, on the same day (65) that the d2EGFP values were measured. With this DNA we determined the d2EGFP copy numbers.

Figure 5:
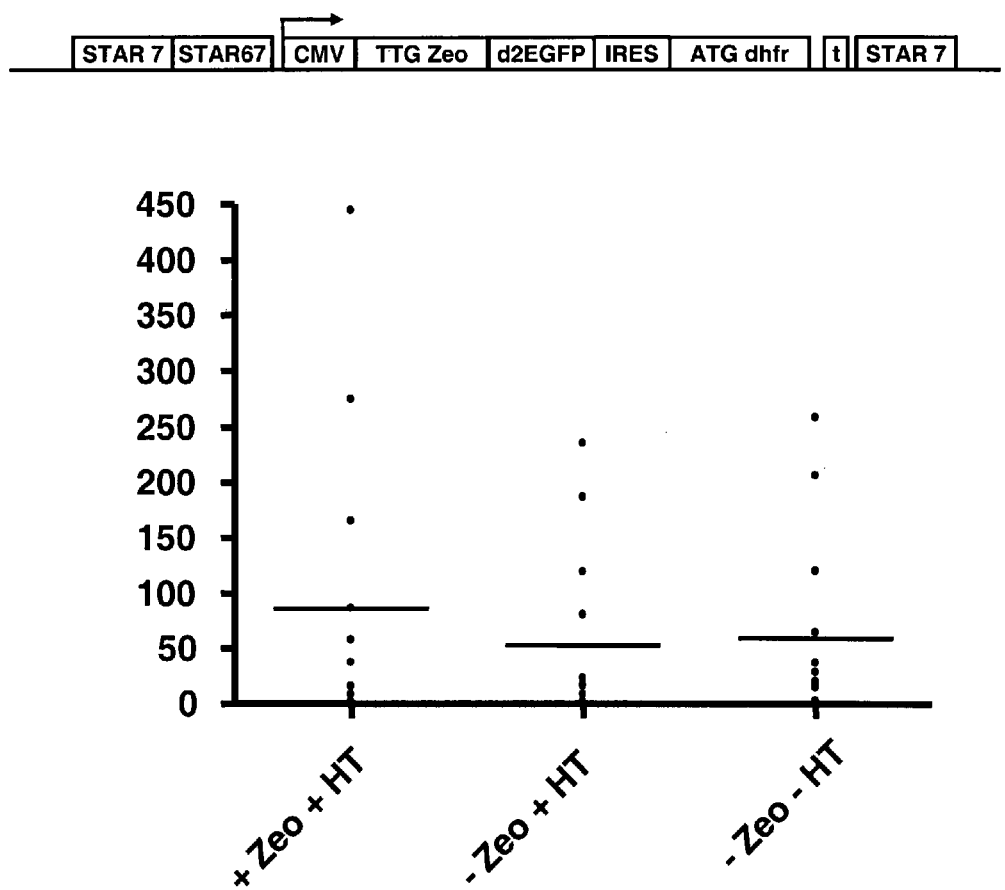
FIG. 5. Copy numbers in clones with the DHFR enzyme (ATG start codon), under different conditions. See Example 3 for details.

The average d2EGFP copy number in the TTG Zeo IRES <u>ATG</u> DHFR clones under ZEOCIN™ selection was 86 (condition 1) (FIG. 5). The average d2EGFP copy number in the TTG Zeo IRES ATG DHFR clones without ZEOCIN™ selection and in the presence of HT supplement was 53 (condition 2) (FIG. 5). The average d2EGFP copy number in the TTG Zeo IRES ATG DHFR clones without ZEOCIN™ selection and without HT supplement was 59 (condition 3) (FIG. 5).

Figure 6:
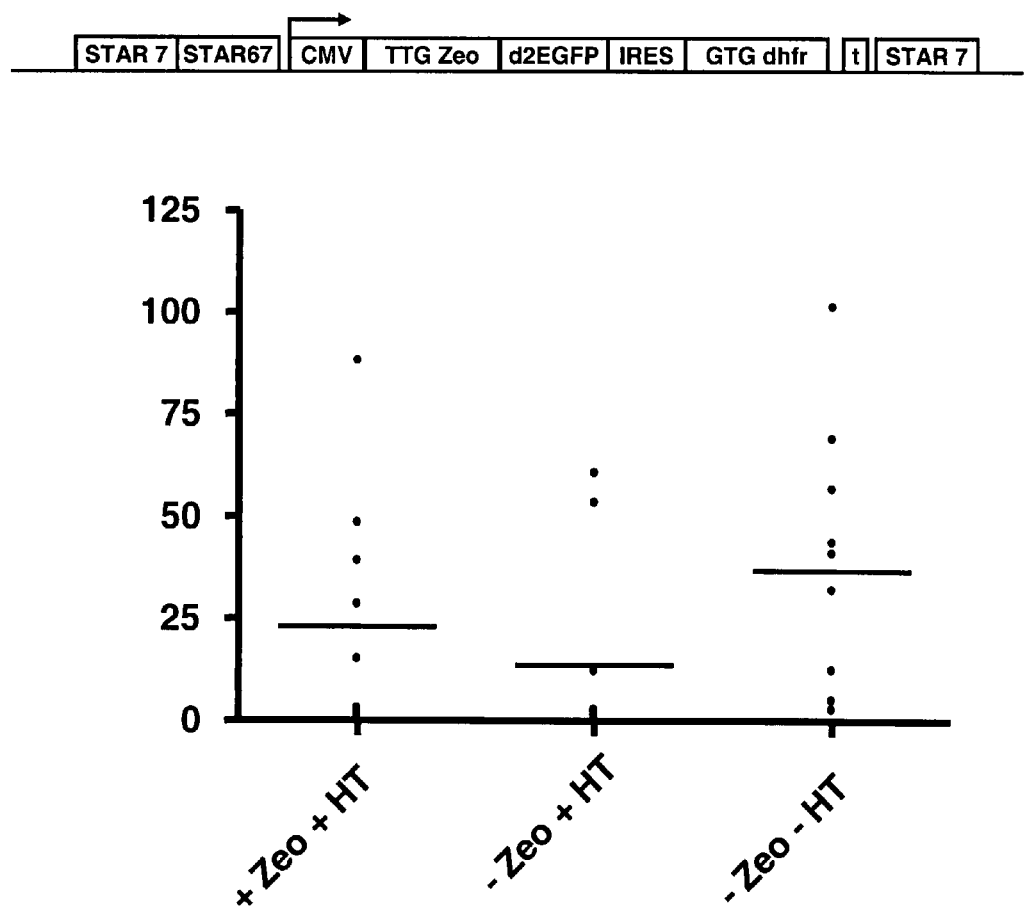
FIG. 6. As FIG. 5, but with dhfr gene having GTG start codon.

The average d2EGFP copy number in the TTG Zeo IRES <u>GTG</u> DHFR clones under ZEOCIN™ selection was 23 (condition 1) (FIG. 6). The average d2EGFP copy number in the TTG Zeo IRES GTG DHFR clones without ZEOCIN™ selection and in the presence of HT supplement was 14 (condition 2) (FIG. 6). The average d2EGFP copy number in the TTG Zeo IRES GTG DHFR clones without ZEOCIN™ selection and without HT supplement was 37 (condition 3) (FIG. 6).

Figure 7:
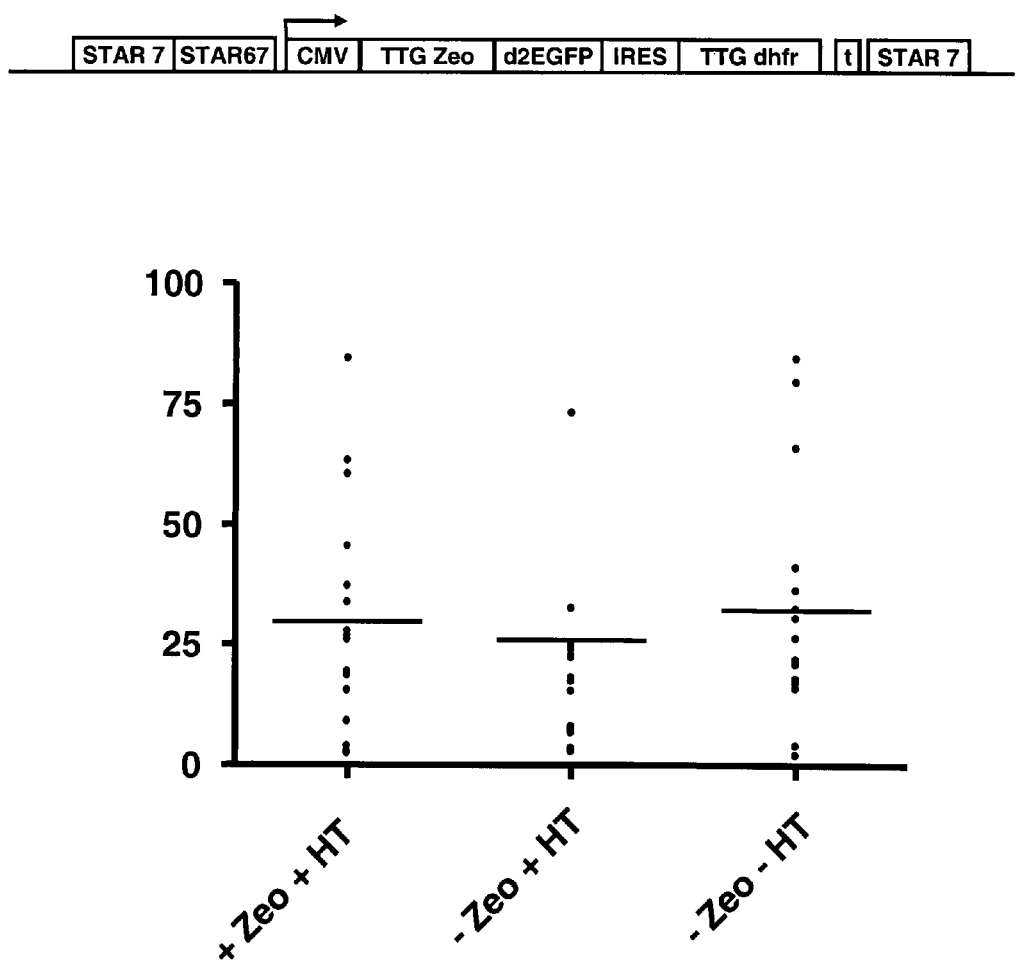
FIG. 7. As FIG. 5, but with dhfr gene having TTG start codon.

The average d2EGFP copy number in the TTG Zeo IRES <u>TTG</u> DHFR clones under ZEOCIN™ selection was 33 (condition 1) (FIG. 7). The average d2EGFP copy number in the TTG Zeo IRES TTG DHFR clones without ZEOCIN™ selection and in the presence of HT supplement was 26 (condition 2) (FIG. 7). The average d2EGFP copy number in the TTG Zeo IRES TTG DHFR clones without ZEOCIN™ selection and without HT supplement was 32 (condition 3) (FIG. 7).

In neither case we observed a strong increase of the d2EGFP copy numbers after removal of HT supplement, which resulted in the increased d2EGFP values in case of the GTG DHFR and TTG DHFR variant. The fact that with both constructs the d2EGFP values remained stable over time and even increased significantly must be due to the action of the DHFR protein. Still, no increased d2EGFP copy numbers were observed in the TTG Zeo TTG DHFR clones at all, and only a modest increase in the TTG Zeo GTG DHFR clones. Interestingly, the overall d2EGFP copy numbers in the lowest producers, the TTG Zeo ATG DHFR clones were higher than in the other two variants, while these clones did not maintain the initial high d2EGFP fluorescence values (see, Example 2). We conclude from these data that the commonly known gene amplification, observed when using the DHFR protein in combination with the addition of methotrexate, is not responsible for keeping the d2EGFP expression levels stable over time and for the observed increase in these expression levels. Instead, it appears that per d2EGFP gene copy more d2EGFP protein is expressed with the GTG and TTG DHFR variants.

We have further analysed the d2EGFP mRNA levels for the different clones and under the different conditions as above, and found that these mRNA levels broadly followed the trend of the d2EGFP fluorescence values. We therefore conclude that the increases in the d2EGFP fluorescence values are due to increased mRNA levels, and not to altered translation efficiencies.

Example 4

Figure 8:
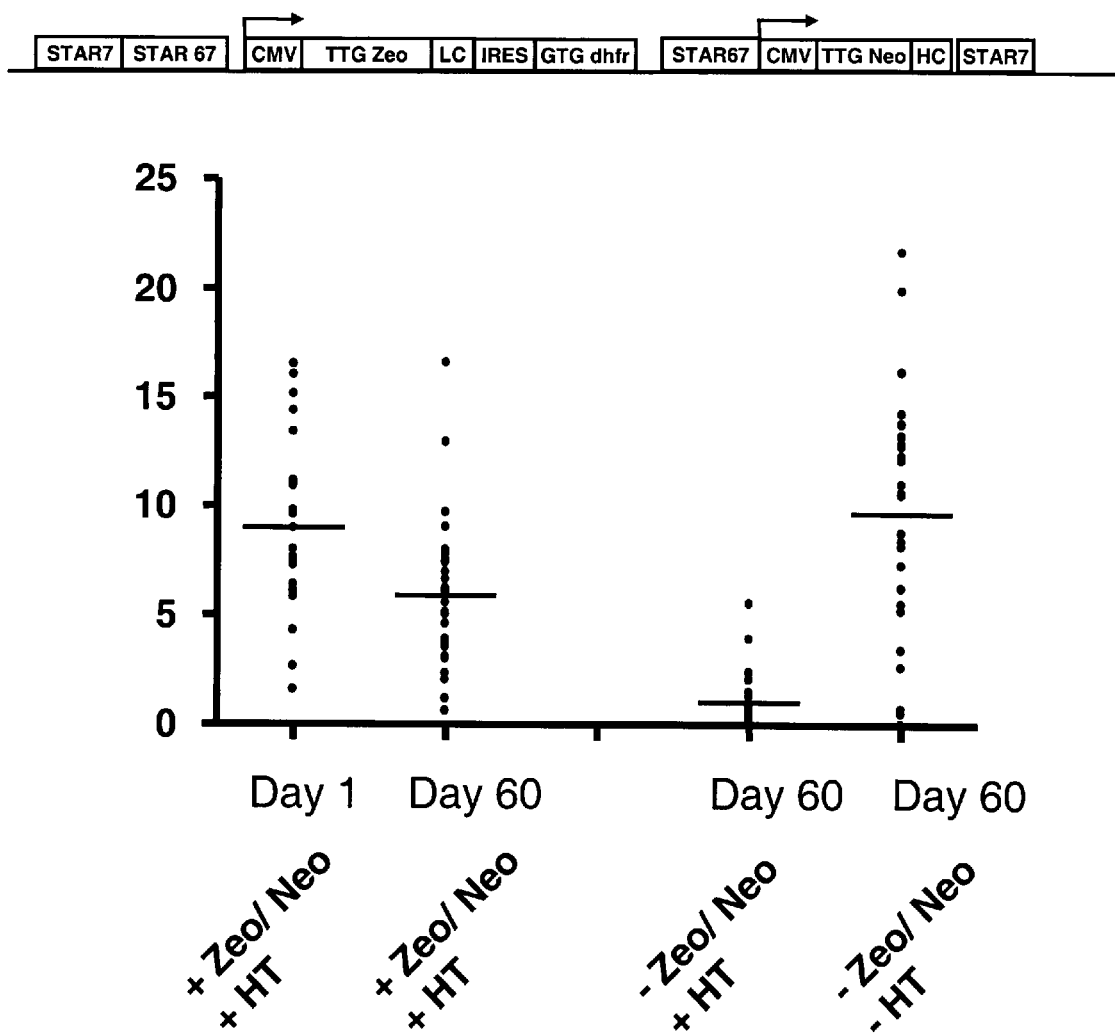
FIG. 8. Results with tricistronic expression cassettes with DHFR as maintenance marker for expression of monoclonal antibody. The upstream tricistronic transcription unit contains a ZEOCIN™ selectable marker gene with a TTG start codon and lacking internal ATG sequences (TTG Zeo) upstream of the sequence encoding an anti-EpCAM antibody light chain (LC), which is further operably linked via an IRES to a downstream dhfr gene with a GTG start codon). A bicistronic transcription unit with a neomycin selectable marker gene with a TTG start codon and lacking internal ATG sequences (TTG Neo) upstream of the sequence encoding the anti-EpCAM antibody heavy chain (HC) is further present on the expression construct. STAR 7 flanks the entire construct, and STAR 67 is placed upstream of both CMV promoters. Dots indicate individual data points (expression of anti-EpCAM antibody in pg/cell/day on vertical axis), lines indicate the average expression levels. The used construct is shown above the graph, conditions are indicated on the horizontal axis (+Zeo/Neo: selection for ZEOCIN™ and neomycin (antibiotics) resistance; −Zeo/Neo: no selection for resistance to antibiotics; +HT: no selection for DHFR expression; −HT: selection for DHFR expression). See Example 4 for details.
Figure 9:
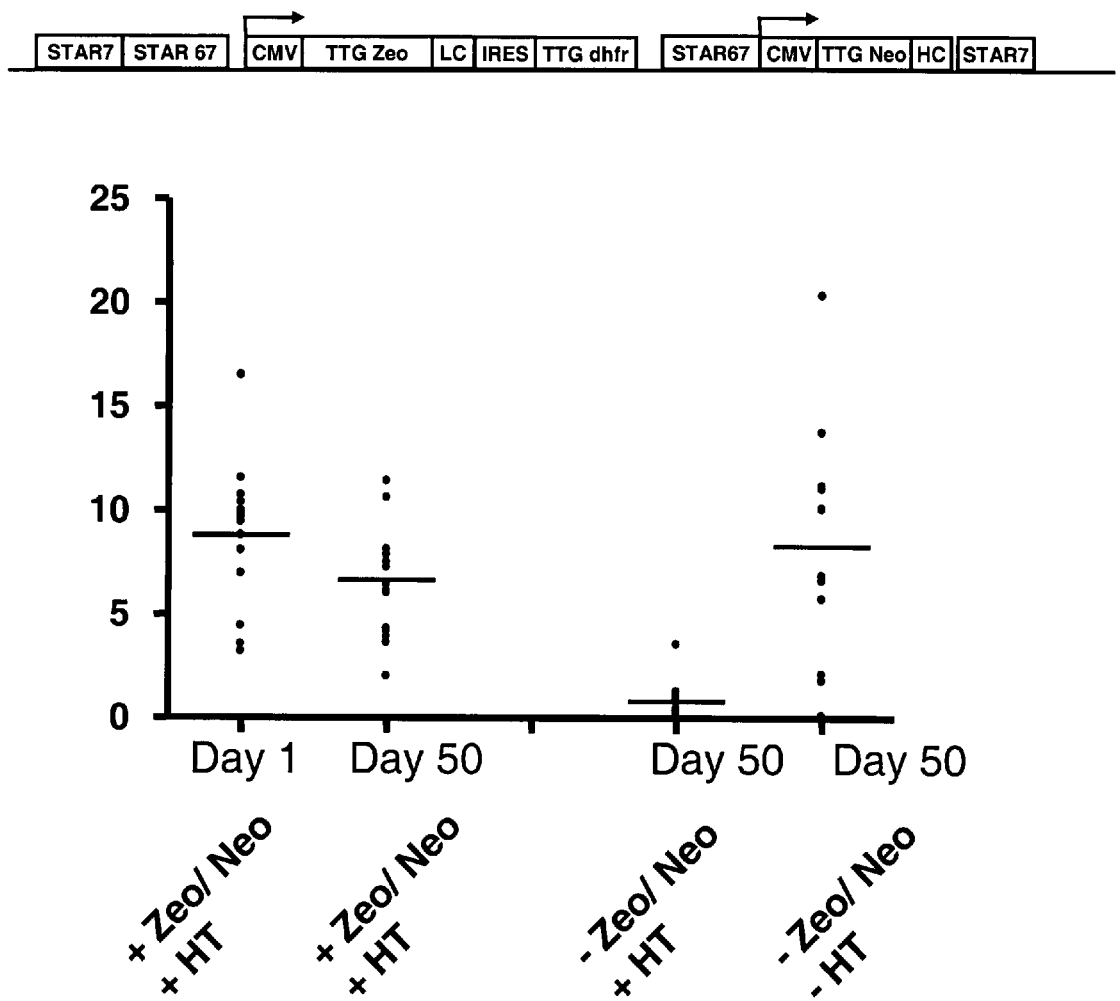
FIG. 9. As FIG. 8, but with a dhfr gene having a TTG start codon.
Figure 10:
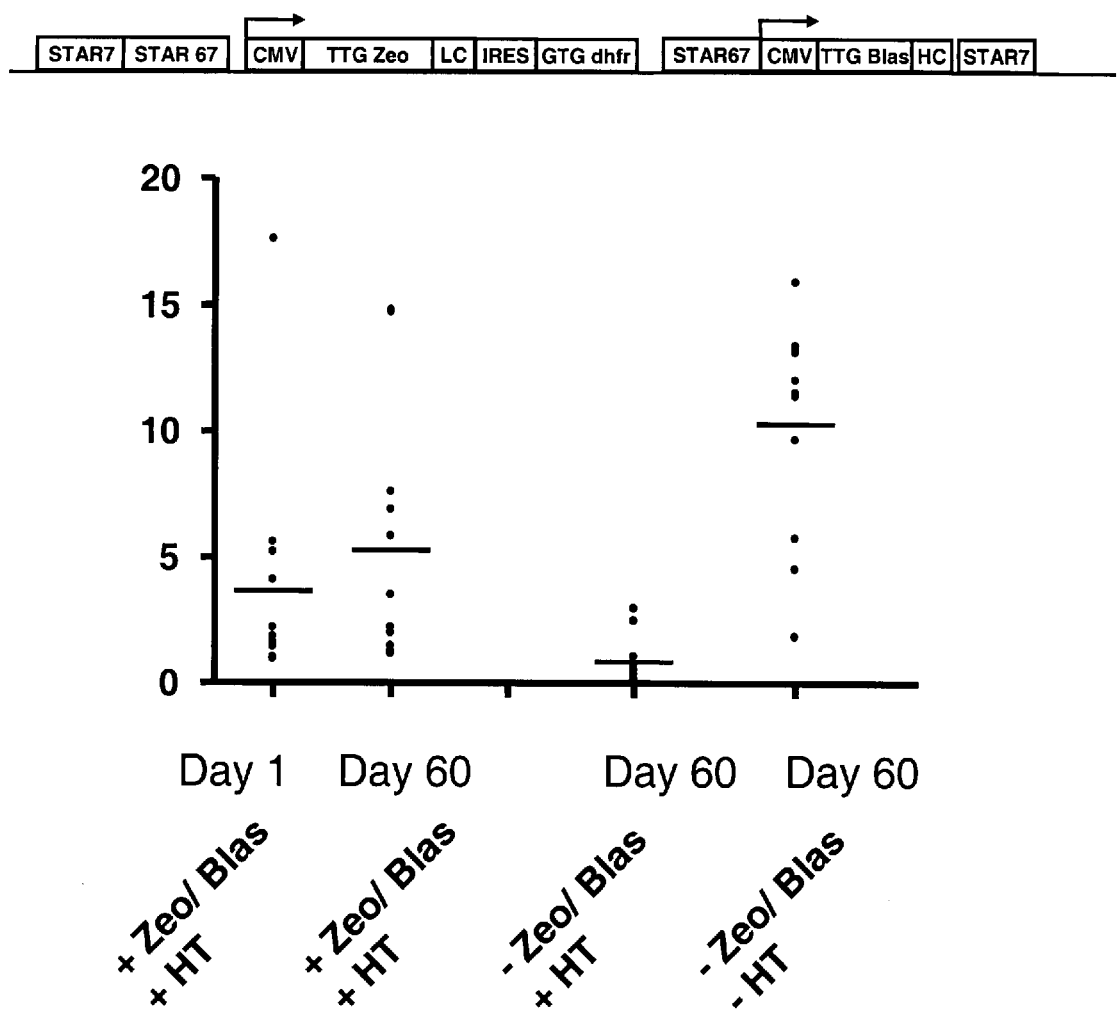
FIG. 10. As FIG. 8, but with blasticidin (Blas) selectable marker instead of Neo for selection of HC expression.
Figure 11:
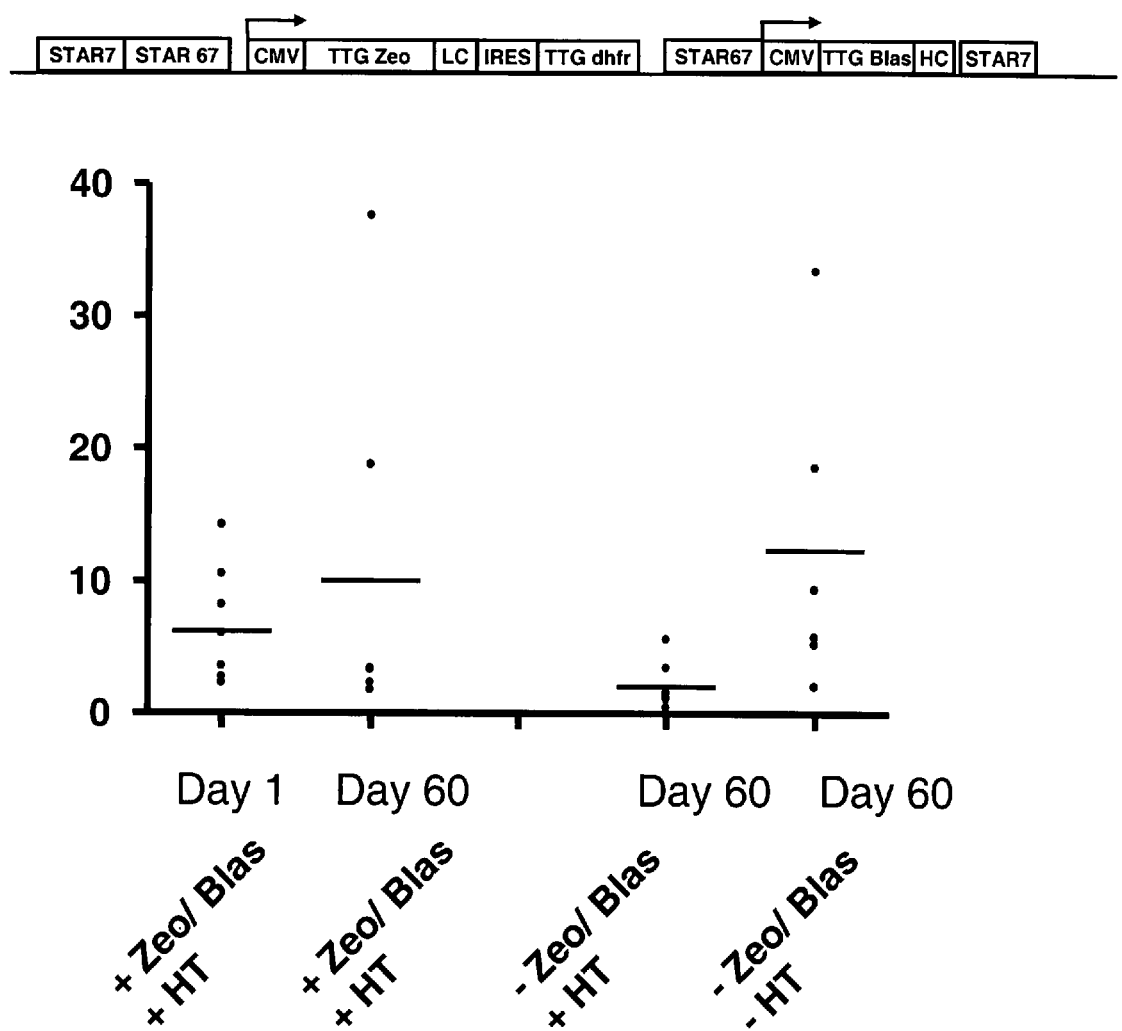
FIG. 11. As FIG. 10, but with dhfr gene having a TTG start codon.

Improved Stability of Monoclonal Antibody Expression by Placing a Modified DHFR Gene Downstream of an IRES Sequence In Example 2, the d2EFGP gene was used as a reporter gene. In this example, the above-explained configurations are used for expression of a monoclonal antibody (anti-EpCAM, see, e.g., Examples 5 and 13 of the incorporated US 2006/017238). In contrast with d2EGFP, an antibody is secreted in the culture medium, and moreover contains two polypeptide chains that are encoded by two genes (heavy and light chain). In the used configuration, these two genes are present on one plasmid, each gene being under control of a separate promoter, and each being part of a multicistronic transcription unit with a different selectable marker gene (FIG. 8). The light chain (LC) was placed in a tricistronic transcription unit with the ZEOCIN™ containing a TTG start codon (TTG-Zeo) upstream as a selectable marker for obtaining high expressing clones, and the dhfr gene with a GTG (FIGS. 8, 10) or TTG (FIGS. 9, 11) start codon downstream of an IRES as a maintenance marker to allow continuous selection for DHFR expression. The heavy chain (HC) transcription unit was placed downstream of the LC transcription unit, and contained a bicistronic construct encoding either neomycin (with reduced CpG content and 185E>D mutation, see Example 23 of US 2006/0195935, incorporated by reference herein) or blasticidin with a TTG start codon (TTG-Neo or TTG-Blas) (FIGS. 8, 9) as a selectable marker upstream of the HC coding sequence. Each transcription unit contained STAR67 upstream of the promoter, and the combination of LC and HC transcription units was flanked by STAR7. The configurations used are shown in the top of FIGS. 8-11. The objective of these expression cassettes was to select a stable monoclonal antibody producing mammalian clone first by selection on ZEOCIN™ and Neomycin (FIGS. 8 and 9) or on ZEOCIN™ and Blasticidin (FIGS. 10 and 11). After this initial selection phase, the characteristics of the DHFR protein are employed to achieve maintenance of the high expression levels in the absence of the antibiotics used for the initial selection phase. The constructs were transfected to CHO-DG44 cells, using Lipofectamine 2000 (Invitrogen). Antibiotic selection agents were used in the following concentrations: ZEOCIN™ (Zeo) at 400 µg/ml, neomycin (Neo) at 500 µg/ml and blasticidin (Blas) at 2 µg/ml.

Two weeks after the transfections the emerging, individual clones were isolated and further cultured for two weeks before culture medium was sampled and antibody expression levels were determined using an ELISA. After these initial measurements (day 1), the cultures were split and cultured further under three conditions: 1) with both antibiotics used for initial selection and with hypoxanthine and thymidine (HT supplement) in the medium (i.e., selection by the antibiotics); 2) without both antibiotics used for initial selection and with HT supplement in the medium (i.e., no selection at all); and 3) without antibiotics used for initial selection and without HT supplement in the medium (i.e., maintenance selection for DHFR expression).

As a first construct, the TTG-Zeo marker was used upstream of the LC and the TTG-Neo marker upstream of the HC. As a maintenance marker, the dhfr gene with a GTG start codon (GTG-DHFR) was coupled to the LC via an IRES (construct STAR7-STAR67-CMV-TTG Zeo LC EpCAM IRES GTG DHFR-STAR67--CMV-TTG Neo HC EpCAM-STAR7). See FIG. 8 for a schematic representation and the results. The average antibody expression of 24 clones at day 1 was 9.0 pg/cell/day. After 60 days under condition 1 (with selection by ZEOCIN™ and neomycin), the average antibody expression level was 6.4 pg/cell/day. After 60 days under condition 2 (no selection), the average antibody expression level was 1.1 pg/cell/day. In contrast, after 60 days under condition 3 (selection for DHFR expression by absence of HT supplement), the average antibody expression level was 10.0 pg/cell/day.

In conclusion, a severe drop in antibody expression levels was observed only in the absence of antibiotic selection and in the presence of HT supplement (absence of selection for DHFR expression). In the absence of antibiotic selection and absence of HT supplement (conditions selecting for expression of DHFR), the antibody expression levels actually increased. This indicates that the expression levels of DHFR with a GTG start codon are sufficiently low to provide high selection stringency. This selection pressure, in the absence of any antibiotics, is sufficiently high not only to maintain high protein expression levels over time. Moreover, it demonstrates that the selection system of the invention works well with a complex protein that is secreted, is encoded by two different genes, and furthermore belongs to a class (antibodies) of wide interest in biotechnology, e.g., as biopharmaceutical products.

A similar experiment was performed wherein the start codon of DHFR was TTG (construct STAR7-STAR67-CMV-TTG Zeo LC EpCAM IRES TTG DHFR-STAR67--CMV-TTG Neo HC EpCAM-STAR7). See FIG. 9 for a schematic representation and the results. The average antibody expression of 15 clones at day 1 was 8.8 pg/cell/day. After 50 days under condition 1 (with selection by ZEOCIN™ and neomycin), the average antibody expression level was 6.7 pg/cell/day. After 50 days under condition 2 (no selection), the average antibody expression level was 0.7 pg/cell/day. In contrast, after 50 days under condition 3 (selection for DHFR expression by absence of HT supplement), the average antibody expression level was 8.3 pg/cell/day. These results are consistent with those where the GTG-DHFR were used, and demonstrate that the selection system of the invention also works for antibody expression using a dhfr gene with a TTG start codon, indicating the applicability of the system for more than one non-ATG start codon.

A similar experiment was performed wherein the HC is coupled to the blasticidin selection gene. First, a dhfr gene was used with a GTG start codon (construct STAR7-STAR67-CMV-TTG Zeo LC EpCAM IRES GTG DHFR-STAR67--CMV-TTG Blas HC EpCAM-STAR7). See FIG. 10 for a schematic representation and the results. The average antibody expression of 12 clones at day 1 was 3.7 pg/cell/day. After 60 days under condition 1 (with selection by ZEOCIN™ and blasticidin), the average antibody expression level was 5.3 pg/cell/day. After 60 days under condition 2 (no selection), the average antibody expression level was 0.8 pg/cell/day. In contrast, after 60 days under condition 3 (selection for DHFR expression by absence of HT supplement), the average antibody expression level was 10.3 pg/cell/day. These results again demonstrate a drop in expression upon removal of all selection but high expression upon maintenance selection using a dhfr gene with a GTG start codon, consistent with previous results where neomycin was used as a selectable marker for the HC. This demonstrates that the selection system also works for antibody expression using blasticidin instead of neomycin for selection of one of the antibody chains, indicating the applicability of the system for multimeric protein expression using different selectable marker proteins.

It was again demonstrated that this selection system also worked when a Dhfr gene with a TTG start codon was used (construct STAR7-STAR67-CMV-TTG Zeo LC EpCAM IRES TTG DHFR-STAR67--CMV-TTG Blas HC EpCAM-STAR7). See FIG. 11 for a schematic representation and the results. The average antibody expression of 8 clones at day 1 was 6.2 pg/cell/day. After 60 days under condition 1 (with selection by ZEOCIN™ and blasticidin), the average antibody expression level was 10.0 pg/cell/day. After 60 days under condition 2 (no selection), the average antibody expression level was 2.0 pg/cell/day. In contrast, after 60 days under condition 3 (selection for DHFR expression by absence of HT supplement), the average antibody expression level was 12.4 pg/cell/day. Thus again, the drop in expression levels upon complete loss of selection pressure was prevented when using the maintenance selection for DHFR expression by a simple culture medium switch, without addition of any antibiotics.

Thus, the results in this example demonstrate that: high antibody expression levels could be obtained by placing each of the light and heavy chain coding sequences in separate multicistronic transcription units, each of the light and heavy chain coding sequences behind a coding sequence for a selectable marker protein (here proteins conferring resistance to antibiotics) having a non-ATG start codon, which selectable marker protein coding sequence further was devoid of ATG sequences. Expression levels of many clones decreased when all selection pressure was removed, but this effect was avoided by coupling a DHFR coding sequence having a non-ATG start codon to one of the antibody chains (here the light chain) via an IRES and selecting for expression of DHFR in DHFR-deficient cells (here CHO-DG44) by omission of HT from the culture medium.

REFERENCES

The Contents of which are Incorporated Herein by this Reference

Kaufman, R J. (2000) Overview of vector design for mammalian gene expression *Mol Biotechnol* 16, 151-160.

Kozak M. (1986) Point mutations define a sequence flanking the AUG initiator codon that modulates translation by eukaryotic ribosomes. Cell 44: 283-292.

Kozak M. (1987) An analysis of 5'-noncoding sequences from 699 vertebrate messenger RNAs. Nucleic Acids Res. 15: 8125-8148.

Kozak M. (1989) Context effects and inefficient initiation at non-AUG codons in eucaryotic cell-free translation systems. Mol Cell Biol. 9: 5073-5080.

Kozak M. (1990) Downstream secondary structure facilitates recognition of initiator codons by eukaryotic ribosomes. Proc Natl Acad Sci USA 87:8301-8305.

Kozak M. (1997) Recognition of AUG and alternative initiator codons is augmented by G in position +4 but is not generally affected by the nucleotides in positions+5 and +6. EMBO J. 16: 2482-2492.

Kozak M. (2002) Pushing the limits of the scanning mechanism for initiation of translation. Gene 299: 1-34.

Lopez de Quinto, S, and Martinez-Salas, E. (1998) Parameters influencing translational efficiency in aphthovirus IRES-based bicistronic expression vectors *Gene* 217, 51-6.

Martinez-Salas, E. (1999) Internal ribosome entry site biology and its use in expression vectors *Curr Opin Biotechnol* 10, 458-64.

McBurney, M W, Mai, T, Yang, X, and Jardine, K. (2002) Evidence for repeat-induced gene silencing in cultured Mammalian cells: inactivation of tandem repeats of transfected genes *Exp Cell Res* 274, 1-8.

Mizuguchi, H, Xu, Z, Ishii-Watabe, A, Uchida, E, and Hayakawa, T. (2000) IRES-dependent second gene expression is significantly lower than cap-dependent first gene expression in a bicistronic vector *Mol Ther* 1, 376-82.

Rees, S, Coote, J, Stables, J, Goodson, S, Harris, S, and Lee, M G. (1996) Bicistronic vector for the creation of stable mammalian cell lines that predisposes all antibiotic-resistant cells to express recombinant protein *Biotechniques* 20, 102-104, 106, 108-110.

Urlaub, G. & Chasin, L. A. Isolation of Chinese hamster cell mutants deficient in dihydrofolate reductase activity. *Proc Natl Acad Sci USA* 77, 4216-20 (1980)

Venkatesan, A, and Dasgupta, A. (2001) Novel fluorescence-based screen to identify small synthetic internal ribosome entry site elements *Mol Cell Biol* 21, 2826-37.

Whitelaw, E, Sutherland, H, Kearns, M, Morgan, H, Weaving, L, and Garrick, D. (2001) Epigenetic effects on transgene expression *Methods Mol Biol* 158, 351-68.

What is claimed is:

1. A DNA molecule comprising a multicistronic transcription unit, wherein the multicistronic transcription unit comprises, from 5' to 3':
   a first anti-repressor (STAR) element that is STAR7 (SEQ ID NO:7),
   an anti-repressor (STAR) element that is STAR67 (SEQ ID NO:66),
   a polynucleotide encoding a first selectable marker polypeptide, wherein the polynucleotide encoding the first selectable marker polypeptide comprises a translation initiation sequence separate from that of a polynucleotide encoding a polypeptide of interest, does not comprise an ATG codon in the coding strand between the start codon of the first selectable marker polypeptide and the start codon of the polypeptide of interest, and comprises a GTG start codon or a TTG start codon,
   the polynucleotide encoding the polypeptide of interest, wherein the polynucleotide encoding the polypeptide of interest has a translation initiation sequence separate from that of a polynucleotide encoding a second selectable marker polypeptide,
   an internal ribosome entry site (IRES),
   the polynucleotide encoding a second selectable marker polypeptide, wherein the polynucleotide encoding the second selectable marker polypeptide is under translational control of the IRES and comprises a GTG start codon, a TTG start codon, a CTG start codon, an ATT start codon or an ACG start codon,
   a transcription terminator, and
   a second anti-repressor (STAR) element that is STAR7 (SEQ ID NO:7).

2. The DNA molecule of claim 1, wherein the second selectable marker polypeptide is dihydrofolate reductase, and wherein the polynucleotide encoding the first selectable marker polypeptide encodes phleomycin D1.

3. A DNA molecule comprising a multicistronic transcription unit, wherein the multicistronic transcription unit comprises:
   a polynucleotide encoding a polypeptide of interest;
   a polynucleotide encoding a first selectable marker polypeptide;
   a polynucleotide encoding a second selectable marker polypeptide;
   an anti-repressor (STAR) element that is STAR67 (SEQ ID NO:66); and
   a transcription terminator,
   wherein the polynucleotide encoding the polypeptide of interest has a translation initiation sequence separate from that of the polynucleotide encoding the first selectable marker polypeptide,
   wherein the polynucleotide encoding the polypeptide of interest is upstream from the polynucleotide coding for the first selectable marker polypeptide in the multicistronic transcription unit,
   wherein the polynucleotide encoding the first selectable marker polypeptide is under translational control of an internal ribosome entry site (IRES) that is present downstream of the polynucleotide coding for the polypeptide of interest and upstream of the polynucleotide coding for the first selectable marker polypeptide,
   wherein the polynucleotide encoding the first selectable marker polypeptide comprises a GTG start codon, a TTG start codon, a CTG start codon, an ATT start codon or an ACG start codon, and
   wherein the polynucleotide encoding the second selectable marker polypeptide:
   comprises a translation initiation sequence separate from that of the polypeptide of interest,
   is positioned upstream of the polynucleotide encoding the polypeptide of interest, does not comprise an ATG codon in the coding strand between the start codon of the second selectable marker polypeptide and the start codon of the polypeptide of interest, and
comprises a GTG start codon or a TTG start codon,
wherein the multicistronic transcription unit further comprises an anti-repressor (STAR) element that is STAR7 (SEQ ID NO:7).

* * * * *